United States Patent
Stemniski et al.

(10) Patent No.: US 9,649,117 B2
(45) Date of Patent: May 16, 2017

(54) ORTHOPEDIC SURGICAL GUIDE

(71) Applicant: MICROPORT ORTHOPEDICS HOLDINGS INC., Tiel (NL)

(72) Inventors: Paul Stemniski, Arlington, TN (US); Richard Obert, Poway, CA (US); Sarah Lancianese, Orlando, FL (US)

(73) Assignee: Microport Orthopedics Holdings, Inc., Tiel (NL)

( * ) Notice: Subject to any disclaimer, the term of this patent is extended or adjusted under 35 U.S.C. 154(b) by 303 days.

(21) Appl. No.: 14/330,670

(22) Filed: Jul. 14, 2014

(65) Prior Publication Data
US 2014/0324053 A1    Oct. 30, 2014

Related U.S. Application Data

(63) Continuation of application No. 13/464,175, filed on May 4, 2012, now Pat. No. 8,808,297, and a
(Continued)

(51) Int. Cl.
*A61F 5/00* (2006.01)
*A61B 17/16* (2006.01)
(Continued)

(52) U.S. Cl.
CPC .......... *A61B 17/1682* (2013.01); *A61B 17/15* (2013.01); *A61B 17/1717* (2013.01);
(Continued)

(58) Field of Classification Search
None
See application file for complete search history.

(56) References Cited

U.S. PATENT DOCUMENTS

| 3,314,420 A | 4/1967 | Smith et al. |
| 3,605,123 A | 9/1971 | Hahn |

(Continued)

FOREIGN PATENT DOCUMENTS

| CN | 101111197 | 1/2008 |
| DE | 2306552 | 8/1974 |

(Continued)

OTHER PUBLICATIONS

Andersson, et al., "Macintosh Arthroplasty In Rheumatoid Arthritis," Acta. Orthrop. Scand., 1974, pp. 245-259, 45(2).
(Continued)

*Primary Examiner* — Sameh Boles
(74) *Attorney, Agent, or Firm* — Duane Morris LLP

(57) ABSTRACT

A surgical device includes an elongate body extending from a proximal end to a distal end. The distal end of the elongate body defines a notch sized and configured to receive a reamer. A coupling assembly is supported by the elongate body and includes a reamer guide body disposed at the distal end of the elongate body. The reamer guide body configured to move between a first position and a second position in which the reaming guide body extends at least partially across the notch. A locking assembly is supported by the elongate body and is configured to releasably engage the coupling assembly to maintain the reamer guide body in the second position.

13 Claims, 68 Drawing Sheets

Related U.S. Application Data continuation-in-part of application No. 13/330,091, filed on Dec. 19, 2011, now Pat. No. 8,808,303, application No. 14/330,670, which is a continuation-in-part of application No. 12/711,307, filed on Feb. 24, 2010, now Pat. No. 9,113,914.

(60) Provisional application No. 61/482,657, filed on May 5, 2011, provisional application No. 61/425,054, filed on Dec. 20, 2010, provisional application No. 61/154,845, filed on Feb. 24, 2009.

(51) Int. Cl.
*A61B 17/15* (2006.01)
*A61B 17/17* (2006.01)
*A61B 17/00* (2006.01)
*A61B 17/56* (2006.01)
*A61F 2/42* (2006.01)
*A61B 34/10* (2016.01)

(52) U.S. Cl.
CPC ...... *A61B 17/1775* (2016.11); *A61B 17/1633* (2013.01); *A61B 2017/0046* (2013.01); *A61B 2017/568* (2013.01); *A61B 2034/108* (2016.02); *A61F 2/4202* (2013.01)

(56) References Cited

U.S. PATENT DOCUMENTS

| | | |
|---|---|---|
| 3,798,679 A | 3/1974 | Ewald |
| 3,808,606 A | 5/1974 | Tronzo |
| 3,843,975 A | 10/1974 | Tronzo |
| 3,855,638 A | 12/1974 | Pilliar |
| 3,938,198 A | 2/1976 | Kahn et al. |
| 3,987,499 A | 10/1976 | Scharbach et al. |
| 4,052,753 A | 10/1977 | Dedo |
| 4,055,862 A | 11/1977 | Farling |
| 4,085,466 A | 4/1978 | Goodfellow et al. |
| 4,098,626 A | 7/1978 | Graham et al. |
| 4,203,444 A | 5/1980 | Bonnell et al. |
| 4,213,816 A | 7/1980 | Morris |
| 4,340,978 A | 7/1982 | Buechel et al. |
| 4,368,040 A | 1/1983 | Weissman |
| 4,436,684 A | 3/1984 | White |
| 4,501,266 A | 2/1985 | McDaniel |
| 4,502,161 A | 3/1985 | Wall |
| 4,586,496 A | 5/1986 | Keller |
| 4,594,380 A | 6/1986 | Chapin et al. |
| 4,601,290 A | 7/1986 | Effron et al. |
| 4,609,551 A | 9/1986 | Caplan et al. |
| 4,627,853 A | 12/1986 | Campbell et al. |
| 4,703,751 A | 11/1987 | Pohl |
| 4,704,686 A | 11/1987 | Aldinger |
| 4,715,860 A | 12/1987 | Amstutz et al. |
| 4,721,104 A | 1/1988 | Kaufman et al. |
| 4,759,350 A | 7/1988 | Dunn et al. |
| 4,769,040 A | 9/1988 | Wevers |
| 4,841,975 A | 6/1989 | Woolson |
| 4,846,835 A | 7/1989 | Grande |
| 4,865,607 A | 9/1989 | Witzel et al. |
| 4,880,429 A | 11/1989 | Stone |
| 4,936,862 A | 6/1990 | Walker et al. |
| 4,979,949 A | 12/1990 | Matsen, III et al. |
| 5,041,138 A | 8/1991 | Vacanti et al. |
| 5,059,216 A | 10/1991 | Winters |
| 5,067,964 A | 11/1991 | Richmond et al. |
| 5,122,144 A | 6/1992 | Bert et al. |
| 5,129,908 A | 7/1992 | Petersen |
| 5,133,759 A | 7/1992 | Turner |
| 5,154,717 A | 10/1992 | Matsen, III et al. |
| 5,162,430 A | 11/1992 | Rhee et al. |
| 5,171,322 A | 12/1992 | Kenny |
| 5,197,985 A | 3/1993 | Caplan et al. |
| 5,206,023 A | 4/1993 | Hunziker |
| 5,226,914 A | 7/1993 | Caplan et al. |
| 5,234,433 A | 8/1993 | Bert et al. |
| 5,250,050 A | 10/1993 | Poggie et al. |
| 5,258,032 A | 11/1993 | Bertin |
| 5,270,300 A | 12/1993 | Hunziker |
| 5,288,797 A | 2/1994 | Khalil et al. |
| 5,303,148 A | 4/1994 | Mattson et al. |
| 5,306,311 A | 4/1994 | Stone et al. |
| 5,314,482 A | 5/1994 | Goodfellow et al. |
| 5,344,459 A | 9/1994 | Swartz |
| 5,360,446 A | 11/1994 | Kennedy |
| 5,365,996 A | 11/1994 | Crook |
| 5,368,858 A | 11/1994 | Hunziker |
| 5,370,692 A | 12/1994 | Fink et al. |
| 5,380,332 A | 1/1995 | Ferrante |
| 5,387,216 A | 2/1995 | Thornhill et al. |
| 5,454,816 A | 10/1995 | Ashby |
| 5,462,550 A | 10/1995 | Dietz et al. |
| 5,468,787 A | 11/1995 | Braden et al. |
| 5,474,559 A | 12/1995 | Bertin et al. |
| 5,478,739 A | 12/1995 | Slivka et al. |
| 5,486,180 A | 1/1996 | Dietz et al. |
| 5,501,687 A | 3/1996 | Willert et al. |
| 5,503,162 A | 4/1996 | Athanasiou et al. |
| 5,523,843 A | 6/1996 | Yamane et al. |
| 5,540,696 A | 7/1996 | Booth, Jr. et al. |
| 5,542,947 A | 8/1996 | Treacy |
| 5,554,190 A | 9/1996 | Draenert |
| 5,556,432 A | 9/1996 | Kubein-Meesenburg et al. |
| 5,571,205 A | 11/1996 | James |
| 5,575,793 A | 11/1996 | Carls et al. |
| 5,578,037 A | 11/1996 | Sanders et al. |
| 5,593,450 A | 1/1997 | Scott et al. |
| 5,597,379 A | 1/1997 | Haines et al. |
| 5,601,563 A | 2/1997 | Burke et al. |
| 5,613,970 A | 3/1997 | Houston et al. |
| 5,616,146 A | 4/1997 | Murray |
| 5,630,820 A | 5/1997 | Todd |
| 5,632,745 A | 5/1997 | Schwartz |
| 5,649,929 A | 7/1997 | Callaway |
| 5,658,291 A | 8/1997 | Techiera |
| 5,671,741 A | 9/1997 | Lang et al. |
| 5,682,886 A | 11/1997 | Delp et al. |
| 5,683,466 A | 11/1997 | Vitale |
| 5,684,562 A | 11/1997 | Fujieda |
| 5,688,282 A | 11/1997 | Baronet et al. |
| 5,728,162 A | 3/1998 | Eckhoff |
| 5,735,277 A | 4/1998 | Schuster |
| 5,749,874 A | 5/1998 | Schwartz |
| 5,749,876 A | 5/1998 | Duvillier et al. |
| 5,765,561 A | 6/1998 | Chen et al. |
| 5,766,259 A | 6/1998 | Sammarco |
| 5,768,134 A | 6/1998 | Swaelens et al. |
| 5,769,899 A | 6/1998 | Schwartz et al. |
| 5,786,217 A | 7/1998 | Tubo et al. |
| 5,798,924 A | 8/1998 | Eufinger et al. |
| 5,800,438 A | 9/1998 | Tuke et al. |
| 5,824,083 A | 10/1998 | Draenert |
| 5,827,289 A | 10/1998 | Reiley et al. |
| 5,830,216 A | 11/1998 | Insall et al. |
| 5,835,619 A | 11/1998 | Morimoto et al. |
| 5,842,477 A | 12/1998 | Naughton et al. |
| 5,847,804 A | 12/1998 | Sarver et al. |
| 5,853,746 A | 12/1998 | Hunziker |
| 5,860,981 A | 1/1999 | Bertin et al. |
| 5,871,018 A | 2/1999 | Delp et al. |
| 5,871,542 A | 2/1999 | Goodfellow et al. |
| 5,871,546 A | 2/1999 | Colleran et al. |
| 5,879,390 A | 3/1999 | Kubein-Meesenburg et al. |
| 5,880,976 A | 3/1999 | DiGioia, III et al. |
| 5,885,296 A | 3/1999 | Masini |
| 5,885,297 A | 3/1999 | Matsen, III |
| 5,885,298 A | 3/1999 | Herrington et al. |
| 5,897,559 A | 4/1999 | Masini |
| 5,899,859 A | 5/1999 | Votruba et al. |
| 5,900,245 A | 5/1999 | Sawhney et al. |
| 5,906,934 A | 5/1999 | Grande et al. |
| 5,911,723 A | 6/1999 | Ashby et al. |
| 5,916,220 A | 6/1999 | Masini |

(56) References Cited

U.S. PATENT DOCUMENTS

| | | |
|---|---|---|
| 5,939,323 A | 8/1999 | Valentini et al. |
| 5,961,523 A | 10/1999 | Masini |
| 5,968,051 A | 10/1999 | Luckman et al. |
| 5,972,385 A | 10/1999 | Liu et al. |
| 5,995,738 A | 11/1999 | DiGioia, III et al. |
| 6,001,895 A | 12/1999 | Harvey et al. |
| 6,002,859 A | 12/1999 | DiGioia, III et al. |
| 6,006,126 A | 12/1999 | Cosman |
| 6,007,537 A | 12/1999 | Burkinshaw et al. |
| 6,010,509 A | 1/2000 | Delgado et al. |
| 6,013,081 A | 1/2000 | Burkinshaw et al. |
| 6,013,103 A | 1/2000 | Kaufman et al. |
| 6,046,379 A | 4/2000 | Stone et al. |
| 6,056,754 A | 5/2000 | Haines et al. |
| 6,056,756 A | 5/2000 | Eng et al. |
| 6,057,927 A | 5/2000 | Levesque et al. |
| 6,077,270 A | 6/2000 | Katz |
| 6,082,364 A | 7/2000 | Balian et al. |
| 6,090,144 A | 7/2000 | Letot et al. |
| 6,093,204 A | 7/2000 | Stone |
| 6,096,043 A | 8/2000 | Techiera et al. |
| 6,102,916 A | 8/2000 | Masini |
| 6,106,529 A | 8/2000 | Techiera |
| 6,110,209 A | 8/2000 | Stone |
| 6,120,541 A | 9/2000 | Johnson |
| 6,126,690 A | 10/2000 | Ateshian et al. |
| 6,139,578 A | 10/2000 | Lee et al. |
| 6,156,069 A | 12/2000 | Amstutz |
| 6,161,080 A | 12/2000 | Aouni-Ateshian et al. |
| 6,187,010 B1 | 2/2001 | Masini |
| 6,200,606 B1 | 3/2001 | Peterson et al. |
| 6,203,546 B1 | 3/2001 | MacMahon |
| 6,203,576 B1 | 3/2001 | Afriat et al. |
| 6,205,411 B1 | 3/2001 | DiGioia, III et al. |
| 6,206,927 B1 | 3/2001 | Fell et al. |
| 6,214,369 B1 | 4/2001 | Grande et al. |
| 6,217,894 B1 | 4/2001 | Sawhney et al. |
| 6,219,571 B1 | 4/2001 | Hargreaves et al. |
| 6,224,632 B1 | 5/2001 | Pappas et al. |
| 6,235,060 B1 | 5/2001 | Kubein-Meesenburg et al. |
| 6,251,143 B1 | 6/2001 | Schwartz et al. |
| 6,254,639 B1 | 7/2001 | Peckitt |
| 6,277,151 B1 | 8/2001 | Lee et al. |
| 6,281,195 B1 | 8/2001 | Rueger et al. |
| 6,283,980 B1 | 9/2001 | Vibe-Hansen et al. |
| 6,296,646 B1 | 10/2001 | Williamson |
| 6,299,905 B1 | 10/2001 | Peterson et al. |
| 6,322,588 B1 | 11/2001 | Ogle et al. |
| 6,327,491 B1 | 12/2001 | Franklin et al. |
| 6,328,765 B1 | 12/2001 | Hardwick et al. |
| 6,344,043 B1 | 2/2002 | Pappas |
| 6,344,059 B1 | 2/2002 | Krakovits et al. |
| 6,352,558 B1 | 3/2002 | Spector |
| 6,358,253 B1 | 3/2002 | Torrie et al. |
| 6,365,405 B1 | 4/2002 | Salzmann et al. |
| 6,371,958 B1 | 4/2002 | Overaker |
| 6,373,250 B1 | 4/2002 | Tsoref et al. |
| 6,375,658 B1 | 4/2002 | Hangody et al. |
| 6,379,367 B1 | 4/2002 | Vibe-Hansen et al. |
| 6,382,028 B1 | 5/2002 | Wooh et al. |
| 6,383,228 B1 | 5/2002 | Schmotzer |
| 6,387,131 B1 | 5/2002 | Miehlke et al. |
| 6,429,013 B1 | 8/2002 | Halvorsen et al. |
| 6,443,988 B2 | 9/2002 | Felt et al. |
| 6,443,991 B1 | 9/2002 | Running |
| 6,444,222 B1 | 9/2002 | Asculai et al. |
| 6,459,927 B1 | 10/2002 | Franklin et al. |
| 6,459,948 B1 | 10/2002 | Ateshian et al. |
| 6,468,314 B2 | 10/2002 | Schwartz et al. |
| 6,478,799 B1 | 11/2002 | Williamson |
| 6,479,996 B1 | 11/2002 | Hoogeveen et al. |
| 6,510,334 B1 | 1/2003 | Schuster et al. |
| 6,520,964 B2 | 2/2003 | Tallarida et al. |
| 6,558,421 B1 | 5/2003 | Fell et al. |
| 6,560,476 B1 | 5/2003 | Pelletier et al. |
| 6,575,980 B1 | 6/2003 | Robie et al. |
| 6,620,168 B1 | 9/2003 | Lombardo et al. |
| 6,626,945 B2 | 9/2003 | Simon et al. |
| 6,626,948 B2 | 9/2003 | Storer et al. |
| 6,632,225 B2 | 10/2003 | Sanford et al. |
| 6,632,235 B2 | 10/2003 | Weikel et al. |
| 6,652,587 B2 | 11/2003 | Felt et al. |
| 6,673,077 B1 | 1/2004 | Katz |
| 6,679,917 B2 | 1/2004 | Ek |
| 6,712,856 B1 | 3/2004 | Carignan et al. |
| 6,738,657 B1 | 5/2004 | Franklin et al. |
| 6,905,514 B2 | 6/2005 | Carignan et al. |
| 6,916,341 B2 | 7/2005 | Rolston |
| 6,928,742 B2 | 8/2005 | Broers et al. |
| 6,932,842 B1 | 8/2005 | Litschko et al. |
| 6,942,667 B1 | 9/2005 | Song |
| 6,944,518 B2 | 9/2005 | Roose |
| 6,969,393 B2 | 11/2005 | Pinczewski et al. |
| 6,980,849 B2 | 12/2005 | Sasso |
| 6,988,015 B1 | 1/2006 | Schopf et al. |
| 6,993,374 B2 | 1/2006 | Sasso |
| 7,008,430 B2 | 3/2006 | Dong et al. |
| 7,058,439 B2 | 6/2006 | Eaton et al. |
| 7,060,074 B2 | 6/2006 | Rosa et al. |
| 7,104,997 B2 | 9/2006 | Lionberger et al. |
| 7,115,131 B2 | 10/2006 | Engh et al. |
| 7,117,027 B2 | 10/2006 | Zheng et al. |
| 7,141,053 B2 | 11/2006 | Rosa et al. |
| 7,184,814 B2 | 2/2007 | Lang et al. |
| 7,201,762 B2 | 4/2007 | Green, Jr. et al. |
| 7,217,276 B2 | 5/2007 | Henderson et al. |
| 7,239,908 B1 | 7/2007 | Alexander et al. |
| 7,245,697 B2 | 7/2007 | Lang |
| 7,282,054 B2 | 10/2007 | Steffensmeier et al. |
| 7,292,674 B2 | 11/2007 | Lang |
| 7,347,690 B2 | 3/2008 | Jordan et al. |
| 7,364,581 B2 | 4/2008 | Michalowicz |
| 7,377,924 B2 | 5/2008 | Raistrick et al. |
| 7,379,529 B2 | 5/2008 | Lang |
| 7,467,892 B2 | 12/2008 | Lang et al. |
| 7,468,075 B2 | 12/2008 | Lang et al. |
| 7,534,263 B2 | 5/2009 | Burdulis, Jr. et al. |
| 7,618,451 B2 | 11/2009 | Berez et al. |
| 7,747,305 B2 | 6/2010 | Dean et al. |
| 7,806,896 B1 | 10/2010 | Bonutti |
| 7,881,768 B2 | 2/2011 | Lang et al. |
| 7,981,158 B2 | 7/2011 | Fitz et al. |
| 7,983,777 B2 | 7/2011 | Melton et al. |
| 8,036,729 B2 | 10/2011 | Lang et al. |
| 8,062,302 B2 | 11/2011 | Lang et al. |
| 8,066,708 B2 | 11/2011 | Lang et al. |
| 8,083,745 B2 | 12/2011 | Lang et al. |
| 8,105,330 B2 | 1/2012 | Fitz et al. |
| 8,112,142 B2 | 2/2012 | Alexander et al. |
| 8,122,582 B2 | 2/2012 | Burdulis, Jr. et al. |
| RE43,282 E | 3/2012 | Alexander et al. |
| 8,715,362 B2 | 5/2014 | Reiley et al. |
| 2001/0001120 A1 | 5/2001 | Masini |
| 2001/0010023 A1 | 7/2001 | Schwartz et al. |
| 2001/0039455 A1 | 11/2001 | Simon et al. |
| 2002/0013626 A1 | 1/2002 | Geistlich et al. |
| 2002/0029038 A1 | 3/2002 | Haines |
| 2002/0045940 A1 | 4/2002 | Giannetti et al. |
| 2002/0059049 A1 | 5/2002 | Bradbury et al. |
| 2002/0068977 A1 | 6/2002 | Jackson |
| 2002/0068979 A1 | 6/2002 | Brown et al. |
| 2002/0072821 A1 | 6/2002 | Baker |
| 2002/0079601 A1 | 6/2002 | Russell et al. |
| 2002/0082703 A1 | 6/2002 | Repicci |
| 2002/0087274 A1 | 7/2002 | Alexander et al. |
| 2002/0106625 A1 | 8/2002 | Hung et al. |
| 2002/0115647 A1 | 8/2002 | Halvorsen et al. |
| 2002/0120274 A1 | 8/2002 | Overaker et al. |
| 2002/0120281 A1 | 8/2002 | Overaker |
| 2002/0123817 A1 | 9/2002 | Clasbrummel et al. |
| 2002/0127264 A1 | 9/2002 | Felt et al. |
| 2002/0133230 A1 | 9/2002 | Repicci |
| 2002/0143402 A1 | 10/2002 | Steinberg |
| 2002/0151986 A1 | 10/2002 | Asculai et al. |

(56) References Cited

U.S. PATENT DOCUMENTS

| | | |
|---|---|---|
| 2002/0156150 A1 | 10/2002 | Williams et al. |
| 2002/0156479 A1 | 10/2002 | Schulzki et al. |
| 2002/0173852 A1 | 11/2002 | Felt et al. |
| 2002/0183850 A1 | 12/2002 | Felt et al. |
| 2002/0198531 A1 | 12/2002 | Millard et al. |
| 2003/0028196 A1 | 2/2003 | Bonutti |
| 2003/0055500 A1 | 3/2003 | Fell et al. |
| 2003/0055501 A1 | 3/2003 | Fell et al. |
| 2003/0055502 A1 | 3/2003 | Lang et al. |
| 2003/0060882 A1 | 3/2003 | Fell et al. |
| 2003/0060883 A1 | 3/2003 | Fell et al. |
| 2003/0060884 A1 | 3/2003 | Fell et al. |
| 2003/0060885 A1 | 3/2003 | Fell et al. |
| 2003/0100907 A1 | 5/2003 | Rosa et al. |
| 2003/0100953 A1 | 5/2003 | Rosa et al. |
| 2003/0120347 A1 | 6/2003 | Steinberg |
| 2003/0158558 A1 | 8/2003 | Horn |
| 2003/0158606 A1 | 8/2003 | Coon et al. |
| 2003/0163137 A1 | 8/2003 | Smucker et al. |
| 2003/0173695 A1 | 9/2003 | Monkhouse et al. |
| 2003/0216669 A1 | 11/2003 | Lang et al. |
| 2003/0225457 A1 | 12/2003 | Justin et al. |
| 2003/0236521 A1 | 12/2003 | Brown et al. |
| 2004/0098133 A1 | 5/2004 | Carignan et al. |
| 2004/0102852 A1 | 5/2004 | Johnson et al. |
| 2004/0122521 A1 | 6/2004 | Lee et al. |
| 2004/0133276 A1 | 7/2004 | Lang et al. |
| 2004/0138754 A1 | 7/2004 | Lang et al. |
| 2004/0147927 A1 | 7/2004 | Tsougarakis et al. |
| 2004/0153079 A1 | 8/2004 | Tsougarakis et al. |
| 2004/0153162 A1 | 8/2004 | Sanford et al. |
| 2004/0153164 A1 | 8/2004 | Sanford et al. |
| 2004/0167390 A1 | 8/2004 | Alexander et al. |
| 2004/0167630 A1 | 8/2004 | Rolston |
| 2004/0193280 A1 | 9/2004 | Webster et al. |
| 2004/0204644 A1 | 10/2004 | Tsougarakis et al. |
| 2004/0204760 A1 | 10/2004 | Fitz et al. |
| 2004/0236424 A1 | 11/2004 | Berez et al. |
| 2004/0249386 A1 | 12/2004 | Faoro |
| 2005/0015153 A1 | 1/2005 | Goble et al. |
| 2005/0021039 A1 | 1/2005 | Cusick et al. |
| 2005/0043807 A1 | 2/2005 | Wood |
| 2005/0049603 A1 | 3/2005 | Calton et al. |
| 2005/0055028 A1 | 3/2005 | Haines |
| 2005/0085920 A1 | 4/2005 | Williamson |
| 2005/0107883 A1 | 5/2005 | Goodfried et al. |
| 2005/0107884 A1 | 5/2005 | Johnson et al. |
| 2005/0119664 A1 | 6/2005 | Carignan et al. |
| 2005/0143745 A1 | 6/2005 | Hodorek et al. |
| 2005/0148843 A1 | 7/2005 | Roose |
| 2005/0171545 A1 | 8/2005 | Walsh et al. |
| 2005/0171612 A1 | 8/2005 | Rolston |
| 2005/0192588 A1 | 9/2005 | Garcia |
| 2005/0216305 A1 | 9/2005 | Funderud |
| 2005/0234461 A1 | 10/2005 | Burdulis, Jr. et al. |
| 2005/0267584 A1 | 12/2005 | Burdulis et al. |
| 2006/0052795 A1 | 3/2006 | White |
| 2006/0111722 A1 | 5/2006 | Bouadi |
| 2006/0149283 A1 | 7/2006 | May et al. |
| 2006/0200162 A1 | 9/2006 | Farling et al. |
| 2006/0235421 A1 | 10/2006 | Rosa et al. |
| 2007/0015995 A1 | 1/2007 | Lang |
| 2007/0073305 A1 | 3/2007 | Lionberger et al. |
| 2007/0118141 A1 | 5/2007 | Marchyn et al. |
| 2007/0198022 A1 | 8/2007 | Lang et al. |
| 2007/0203430 A1 | 8/2007 | Lang et al. |
| 2007/0233151 A1 | 10/2007 | Chudik |
| 2007/0233156 A1 | 10/2007 | Metzger |
| 2007/0276224 A1 | 11/2007 | Lang et al. |
| 2007/0293868 A1 | 12/2007 | Delfosse et al. |
| 2008/0004709 A1 | 1/2008 | O'Neill et al. |
| 2008/0015433 A1 | 1/2008 | Alexander et al. |
| 2008/0025463 A1 | 1/2008 | Lang et al. |
| 2008/0031412 A1 | 2/2008 | Lang et al. |
| 2008/0058613 A1 | 3/2008 | Lang et al. |
| 2008/0058945 A1 | 3/2008 | Hajaj et al. |
| 2008/0114370 A1 | 5/2008 | Schoenefeld |
| 2008/0170659 A1 | 7/2008 | Lang et al. |
| 2008/0195216 A1 | 8/2008 | Philipp |
| 2008/0219412 A1 | 9/2008 | Lang |
| 2008/0243127 A1 | 10/2008 | Lang |
| 2008/0255565 A1 | 10/2008 | Fletcher |
| 2008/0275452 A1 | 11/2008 | Lang et al. |
| 2008/0281328 A1 | 11/2008 | Lang et al. |
| 2008/0281329 A1 | 11/2008 | Lang et al. |
| 2008/0281426 A1 | 11/2008 | Fitz et al. |
| 2008/0287953 A1 | 11/2008 | Sers |
| 2009/0024131 A1 | 1/2009 | Metzger et al. |
| 2009/0043310 A1* | 2/2009 | Rasmussen ......... A61B 17/025 606/88 |
| 2009/0076371 A1 | 3/2009 | Lang et al. |
| 2009/0087276 A1 | 4/2009 | Rose |
| 2009/0088753 A1 | 4/2009 | Aram et al. |
| 2009/0088758 A1 | 4/2009 | Bennett |
| 2009/0099567 A1 | 4/2009 | Zajac |
| 2009/0131941 A1 | 5/2009 | Park et al. |
| 2009/0131942 A1 | 5/2009 | Aker et al. |
| 2009/0222014 A1 | 9/2009 | Bojarski et al. |
| 2009/0307893 A1 | 12/2009 | Burdulis, Jr. et al. |
| 2010/0160917 A1 | 6/2010 | Fitz et al. |
| 2010/0262150 A1 | 10/2010 | Lian |
| 2010/0281678 A1 | 11/2010 | Burdulis, Jr. et al. |
| 2010/0298894 A1 | 11/2010 | Bojarski et al. |
| 2010/0305573 A1 | 12/2010 | Fitz et al. |
| 2010/0305574 A1 | 12/2010 | Fitz et al. |
| 2011/0066193 A1 | 3/2011 | Lang et al. |
| 2011/0071581 A1 | 3/2011 | Lang et al. |
| 2011/0213368 A1 | 9/2011 | Fitz et al. |
| 2011/0213373 A1 | 9/2011 | Fitz et al. |
| 2011/0213374 A1 | 9/2011 | Fitz et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0218539 A1 | 9/2011 | Fitz et al. |
| 2011/0218584 A1 | 9/2011 | Fitz et al. |
| 2011/0230888 A1 | 9/2011 | Lang et al. |
| 2011/0238073 A1 | 9/2011 | Lang et al. |
| 2011/0313423 A1 | 12/2011 | Lang et al. |
| 2011/0319897 A1 | 12/2011 | Lang et al. |
| 2011/0319900 A1 | 12/2011 | Lang et al. |
| 2012/0029520 A1 | 2/2012 | Lang et al. |
| 2012/0041446 A1 | 2/2012 | Wong et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0101503 A1 | 4/2012 | Lang et al. |
| 2012/0143197 A1 | 6/2012 | Lang et al. |
| 2012/0151730 A1 | 6/2012 | Fitz et al. |
| 2012/0158001 A1 | 6/2012 | Burdulis, Jr. et al. |

FOREIGN PATENT DOCUMENTS

| | | |
|---|---|---|
| DE | 3516743 | 11/1986 |
| DE | 44 34 539 | 4/1996 |
| DE | 20303498 | 8/2003 |
| DE | 202008017199 | 3/2009 |
| DE | 202008017200 | 3/2009 |
| EP | 0377901 | 10/1989 |
| EP | 0528080 | 2/1993 |
| EP | 0530804 | 10/1993 |
| EP | 0626156 | 11/1994 |
| EP | 0704193 | 4/1996 |
| EP | 0896825 | 2/1999 |
| EP | 0938869 | 9/1999 |
| EP | 0613380 | 12/1999 |
| EP | 0993807 | 4/2000 |
| EP | 1074229 | 2/2001 |
| EP | 1077253 | 2/2001 |
| EP | 1120087 | 8/2001 |

(56) References Cited

FOREIGN PATENT DOCUMENTS

| | | |
|---|---|---|
| EP | 1129675 | 9/2001 |
| EP | 1132061 | 9/2001 |
| EP | 0732091 | 12/2001 |
| EP | 0814731 | 8/2002 |
| EP | 1234552 | 8/2002 |
| EP | 1234555 | 8/2002 |
| EP | 0809987 | 10/2002 |
| EP | 0833620 | 10/2002 |
| FR | 2819714 | 7/2002 |
| GB | 1451283 | 9/1976 |
| GB | 2291355 | 1/1996 |
| GB | 2348373 | 10/2000 |
| JP | 8-173465 | 7/1996 |
| JP | 9-206322 | 8/1997 |
| JP | 2002-102236 | 4/2002 |
| JP | 2008-537689 | 9/2008 |
| WO | WO 87/02882 | 5/1987 |
| WO | WO 90/09769 | 9/1990 |
| WO | WO 93/04710 | 3/1993 |
| WO | WO 93/09819 | 5/1993 |
| WO | WO 93/25157 | 12/1993 |
| WO | WO 95/27450 | 10/1995 |
| WO | WO 95/28688 | 10/1995 |
| WO | WO 95/30390 | 11/1995 |
| WO | WO 95/32623 | 12/1995 |
| WO | WO 96/24302 | 8/1996 |
| WO | WO 97/25942 | 7/1997 |
| WO | WO 97/26847 | 7/1997 |
| WO | WO 97/27885 | 8/1997 |
| WO | WO 97/38676 | 10/1997 |
| WO | WO 98/12994 | 4/1998 |
| WO | WO 98/20816 | 5/1998 |
| WO | WO 98/30617 | 7/1998 |
| WO | WO 98/32384 | 7/1998 |
| WO | WO 99/02654 | 1/1999 |
| WO | WO 99/08598 | 2/1999 |
| WO | WO 99/08728 | 2/1999 |
| WO | WO 99/42061 | 8/1999 |
| WO | WO 99/47186 | 9/1999 |
| WO | WO 99/51719 | 10/1999 |
| WO | WO 99/56674 | 11/1999 |
| WO | WO 00/09179 | 2/2000 |
| WO | WO 00/15153 | 3/2000 |
| WO | WO 00/35346 | 6/2000 |
| WO | WO 00/48550 | 8/2000 |
| WO | WO 00/59411 | 10/2000 |
| WO | WO 00/74554 | 12/2000 |
| WO | WO 01/10356 | 2/2001 |
| WO | WO 01/17463 | 3/2001 |
| WO | WO 01/19254 | 3/2001 |
| WO | WO 01/35968 | 5/2001 |
| WO | WO 01/45764 | 6/2001 |
| WO | WO 01/68800 | 9/2001 |
| WO | WO 01/70142 | 9/2001 |
| WO | WO 01/91672 | 12/2001 |
| WO | WO 02/00270 | 1/2002 |
| WO | WO 02/00275 | 1/2002 |
| WO | WO 02/02158 | 1/2002 |
| WO | WO 02/22013 | 3/2002 |
| WO | WO 02/22014 | 3/2002 |
| WO | WO 02/23483 | 3/2002 |
| WO | WO 02/34310 | 5/2002 |
| WO | WO 02/36147 | 5/2002 |
| WO | WO 02/096268 | 12/2002 |
| WO | WO 03/007788 | 1/2003 |
| WO | WO 03/037192 | 5/2003 |
| WO | WO 03/047470 | 6/2003 |
| WO | WO 03/051210 | 6/2003 |
| WO | WO 03/055400 | 7/2003 |
| WO | WO 2004/043305 | 5/2004 |
| WO | WO 2004/049981 | 6/2004 |
| WO | WO 2005/051239 | 6/2005 |
| WO | WO 2005/051240 | 6/2005 |
| WO | WO 2006/060795 | 6/2006 |
| WO | WO 2006/127283 | 11/2006 |
| WO | WO 2007/041375 | 4/2007 |
| WO | WO 2007/061983 | 5/2007 |
| WO | WO 2007/092841 | 8/2007 |
| WO | WO 2008/112996 | 9/2008 |
| WO | WO 2008/157412 | 12/2008 |
| WO | WO 2009/001083 | 12/2008 |
| WO | WO 2009/111639 | 9/2009 |
| WO | 2009/158522 A1 | 12/2009 |
| WO | WO 2010/099142 | 9/2010 |
| WO | WO 2010/121147 | 10/2010 |
| WO | WO 2011/110374 | 9/2011 |

OTHER PUBLICATIONS

Argenson, et al., "Is There a Place for Patellofemoral Arthroplasty?,"Clinical Orthopaedics and Related Research No. 321, 1995, pp. 162-167.

Birnbaum, et al., "Computer-Assisted Orthopedic Surgery with Individual Templates and Comparison to Conventional Operation Method," Spine, Feb. 2001, pp. 365-369, vol. 26, No. 4.

Chelule, et al., "Computer Aided Design of Personalized Jigs in Total Knee Replacement," 3rd Annual Meeting of CAOS Int'l Proc., Jun. 18-21, 2003, pp. 58-59, Spain.

Dare, S., Bobyn, J., Drouin, G., Dussault, R., Gariepy, R., "Use of Computerized Tomography and Numerical Control Machining for the Fabrication of Custom Arthroplasty Prostheses." Second World Congress on Biomaterials, 10th Annual Meeting of the Society for Biomaterials, p. 233, Washington, D.C., Apr. 27-May 1, 1984.

De Winter, et al., "The Richards Type II Patellofemoral Arthroplasty," Acta Orthop Scand, 2001, pp. 487-490, 72(5).

Delp, et al., "A Graphics-Based Software System to Develop and Analyze Models of Musculoskeletal Structures," Comput. Biol. Med., 1995, pp. 21-34, vol. 25, No. 1.

Farrar, et al., "Computed Tomography Scan Scout Film for Measurement of Femoral Axis in Knee Arthroplasty," J. Arthroplasty, 1999, pp. 1030-1031, vol. 14, No. 8.

Final Official Action for U.S. Appl. No. 13/465,547, dated Feb. 26, 2014.

First Office Action for Japanese Patent Appln. No. 2011-552091, dated Oct. 25, 2013.

Froemel, et al., "Computer Assisted Template Based Navigation for Total Knee Replacement," Documents presented at CAOS on Jun. 17, 2001, 4 pages.

Hafez, et al., "Computer Assisted Total Knee Replacement: Could a Two-Piece Custom Template Replace the Complex Conventional Instrumentations?", 4th Annual Meeting of CAOS Int'l Proc., Jun. 16-19, 2004, pp. 63-64, Chicago.

Hafez, et al., "Computer-Assisted Total Hip Arthroplasty: The Present and the Future," Future Rheumatol., 2006, pp. 121-131, vol. 1.

Kim, et al., "Measurement of Femoral Neck Anteversion in 3D. Part 1: 3D Imaging Method," Med. and Biol. Eng. and Computing, 2000, pp. 603-609, vol. 38, No. 6.

Lam, et al., "X-Ray Diagnosis: A Physician's Approach," 1998, Title page and Table of Contents pages Only, ISBN 9813083247, Springer-Verlag publishers.

Lam, et al.. "VarusNalgus Alignment of the Femoral Component in Total Knee Arthroplasty," The Knee, 2003, pp. 237-241, vol. 10.

Lu, et al., "In Vitro Degradation of Porous poly(L-lactic acid) Foams," Biomaterials, Aug. 2000, pp. 1595-1605, 21(15).

Marler, et al., "Soft-Tissue Augmentation with Injectable Alginate and Synegeneic Fibroblasts," Plastic & Reconstructive Surgery, May, 2000 pp. 2049-2058, 105(6).

PCT/US2010/025143, International Preliminary Report on Patentability and Written Opinion, Sep. 9, 2011.

Portheine, "Model-Based Operation Planning in Orthopedic Surgery," Thesis, Apr. 22, 2004, 90 pages, RWTH Aachen University, in German.

Portheine, "Model-Based Operation Planning in Orthopedic Surgery," Thesis, Apr. 22, 2004, 170 pages, RWTH Aachen University, English Translation with Certification.

(56) References Cited

OTHER PUBLICATIONS

Portheine, et al., "Potentials of CT-based Planning and Template-based Procedure in Hip and Knee Surgery," Orth. Prac., 2000, pp. 786-791, vol. 36, English Translation with Certification.
Portheine. et al.. "Potentials of CT-based Planning and Template-based Procedure in Hip and Knee Surgery," Orth. Prac., 2000, pp. 786-791, vol. 36, in German.
Radermacher, "Computer Assisted Matching of Planning and Execution in Orthopedic Surgery," Slide Presentation, Nov. 29, 1993, 22 pages.
Radermacher, "Computer-Based Decision Support in the Selection and Evaluation of Contact Surfaces for Manual Referencing," Lecture presented at Helmholtz Meeting '98 and OSS '98, 7 pages, in German.
Radermacher, "Computer-Based Decision Support in the Selection and Evaluation of Contact Surfaces for Manual Referencing," Lecture presented at Helmholtz Meeting '98 and OSS '98, 8 pages, English Translation with Certifications.
Radermacher, "Image Guided Orthopedic Surgery with Individual Templates," Helmholtz-Institute for Biomed. Eng., 1997, 2 pages.
Radermacher, "Template Based Navigation—An Efficient Technique for Hip and Knee Surgery," CAOS First Asian Meet, Mar. 27-28, 2004, pp. 45-50, India.
Radermacher, et al., "Computer Assisted Matching of Planning and Execution in Orthopedic Surgery," IEEE, EMBS, 1993, pp. 946-947, San Diego.
Radermacher, et al., "Computer Integrated Advanced Orthopedics (CIAO)," 2nd European Conference on Eng. and Med., Apr. 26, 1993, 12 pages.
Radermacher, et al., "Computer Integrated Surgery—Connecting Planning and Execution of Surgical Intervention in Orthopedics," Surgical Therapy Technology, Helmholtz-Institut Aachen Research Report, 1991-1992, pp. 187, 196-202.
Radermacher, et al., "Computer-Assisted Operative Interventions in Orthopedics—Are There Prospects for Endoprosthetics As Well?", Prac. Ortho., 1997, pp. 149-164, vol. 27, in German.
Radermacher, et al., "Computer-Assisted Planning and Operation in Orthopedics," Orth. Prac. 36th Year, Dec. 2000, pp. 731-737, English Translation with Certification.
Radermacher, et al., "Surgical Therapy Technology," Helmholtz-Institut Aaachen Research Report, 1993-1994, pp. 189-219.
Radermacher. et al.. "Computer-Assisted Operative Interventions in Orthopedics—Are There Prospects for Endoprosthetics As Well?". Prac. Ortho., 1997, pp. 1-17, vol. 27, English Translation with Certification.
Radermacher. et al.. "Computer-Assisted Planning and Operation in Orthopedics," Orth. Prac. 36th Year, Dec. 2000, pp. 731-737, in German.
Rau, et al., "Small and Neat," Medical Tech. Int'l, 1993-94, pp. 65, 67 and 69.
Schkommadau, et al., "Clinical Application of Individual Templates for Pedicle Screw Placement in Comparison to Computer Navigation," Poster presented at CAOS, Feb. 18, 2000, 1 page.
Schkommadau, et al., "Clinical Experience With the Individual Template Technique," Orth. Prac., 2001, pp. 19-22, vol. 37, No. 1, in German.
Schkommadau, et al., "Clinical Experience With the Individual Template Technique," Orth. Prac., 2001, pp. 19-22, vol. 37, No. 1, English Translation with Certification.
Seel, et al., "Three-Dimensional Planning and Virtual Radiographs in Revision Total Hip Arthroplasty for Instability," Clinical Orthopaedics and Related Research, Jan. 2006, pp. 35-38, No. 442.
Slone, et al., "Body CT: a Practical Approach," 1999, Title page and Table of Contents pages Only, ISBN 007058219, McGraw-Hill.
Staudte, et al., "Computer-Assisted Operation Planning and Technique in Orthopedics," North Rhine-Westphalia Acad. for Sciences, Lecture N.444, 2000, 17 pages, ISSN 0944-8799, in German.
Staudte, et al., "Computer-Assisted Operation Planning and Technique in Orthopedics," North Rhine-Westphalia Acad. for Sciences, Lecture N.444, 2000, 34 pages, ISSN 0944-8799, English Translation with Certification.
Stauffer, et al., "The Macintosh Prosthesis. Prospective Clinical and Gait Evaluation," Arch. Surg., 1975, pp. 717-720, 110(6).
Stout, et al., "X-Ray Structure Determination: A Practical Guide," 1989, Title page and Table of Contents pages Only, ISBN 0471607118, John Wiley & Sons.
Tamez-Pena, et al., "MRIIsotropic Resolution Reconstruction from Two Orthogonal Scans," Proceedings of the SPIE—The International Society for Optical Engineering SOIE-OMT, 2001, pp. 87-97, vol. 4322.
Testi, et al., "Border Tracing Algorithm Implementation for the Femoral Geometry Reconstruction," Camp. Meth. and Programs in Biomed., 2001, pp. 175-182, vol. 65.
Vandeberg, et al., "Assessment of Knee Cartilage in Cadavers with Dual-Detector Spiral CT Arthrography and MR Imaging," Radiology, Feb. 2002, pp. 430-435, 222(2).
Wiese, et al., "Biomaterial Properties and Biocompatibility in Cell Culture of a Novel Self-Inflating Hydrogel Tissue Expander," J. Biomedical Materials Research Part A, Nov. 2000, pp. 179-188, 54(2).
Woolson, S., Fellingham, L., Dev, P., and Vassiliadis, A., "Three Dimensional Imaging of Bone from Analysis of Computed Tomography Data." Orthopedics, vol. 8, No. 10, pp. 1269-1273, Oct. 1985.
Yusof, et al., "Preparation and Characterization of Chitin Beads as a Wound Dressing Precursor," J. Biomedical Materials Research Part A, Oct. 2000, pp. 59-68, 54(1).
In the United States Patent and Trademark Office: Final Office action issued for U.S. Appl. No. 12/711,307, Feb. 4, 2015, 17 pages.

\* cited by examiner

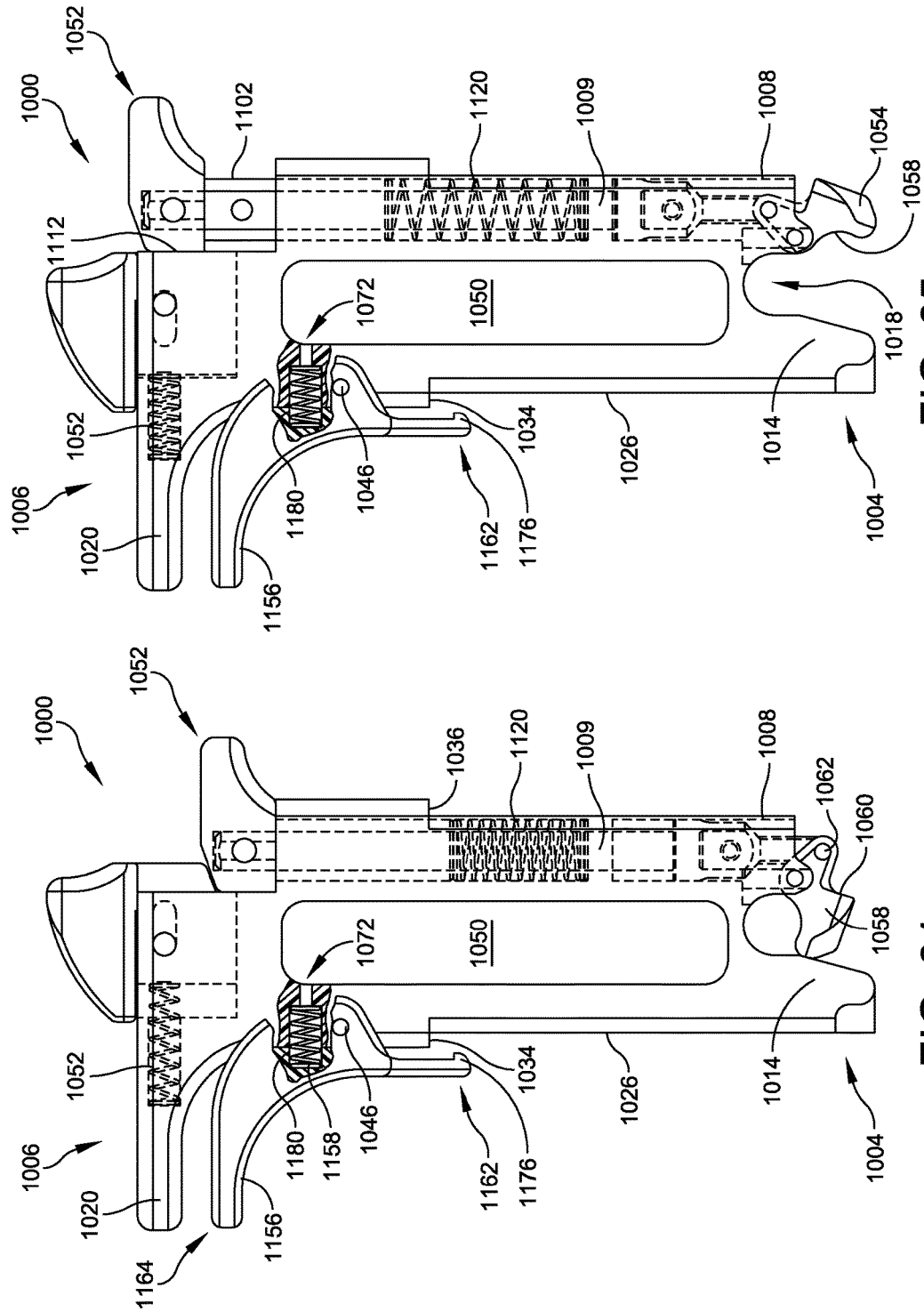

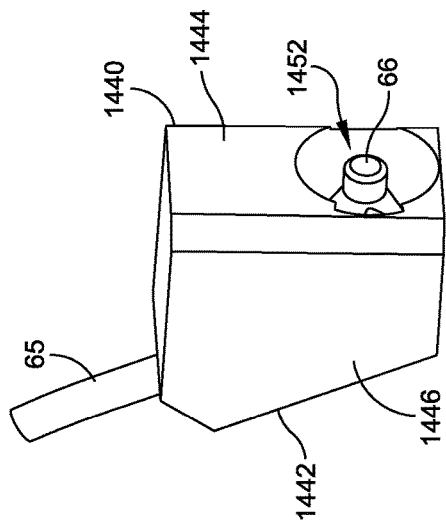
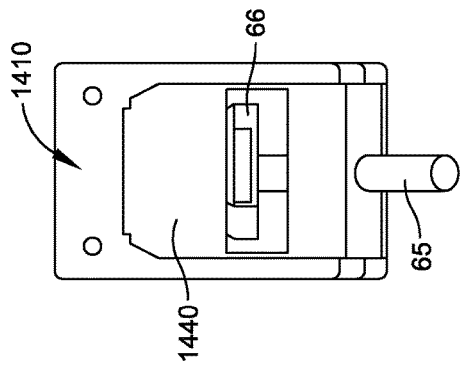
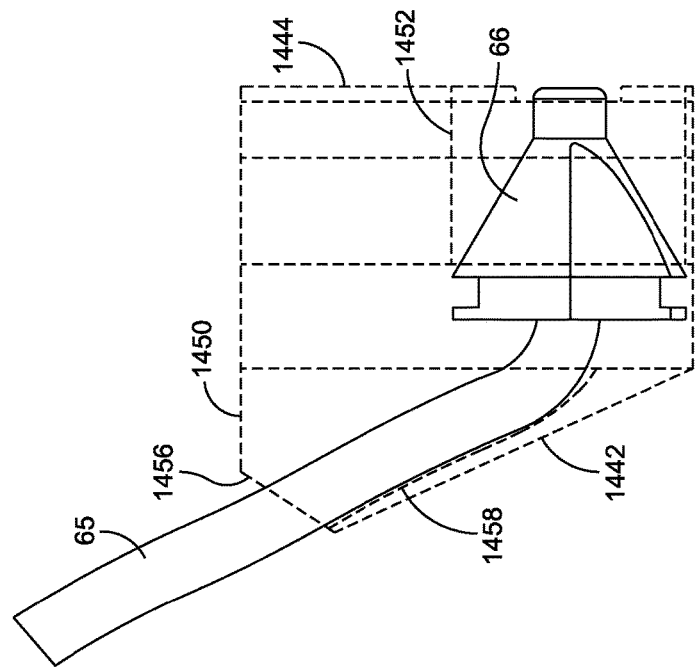

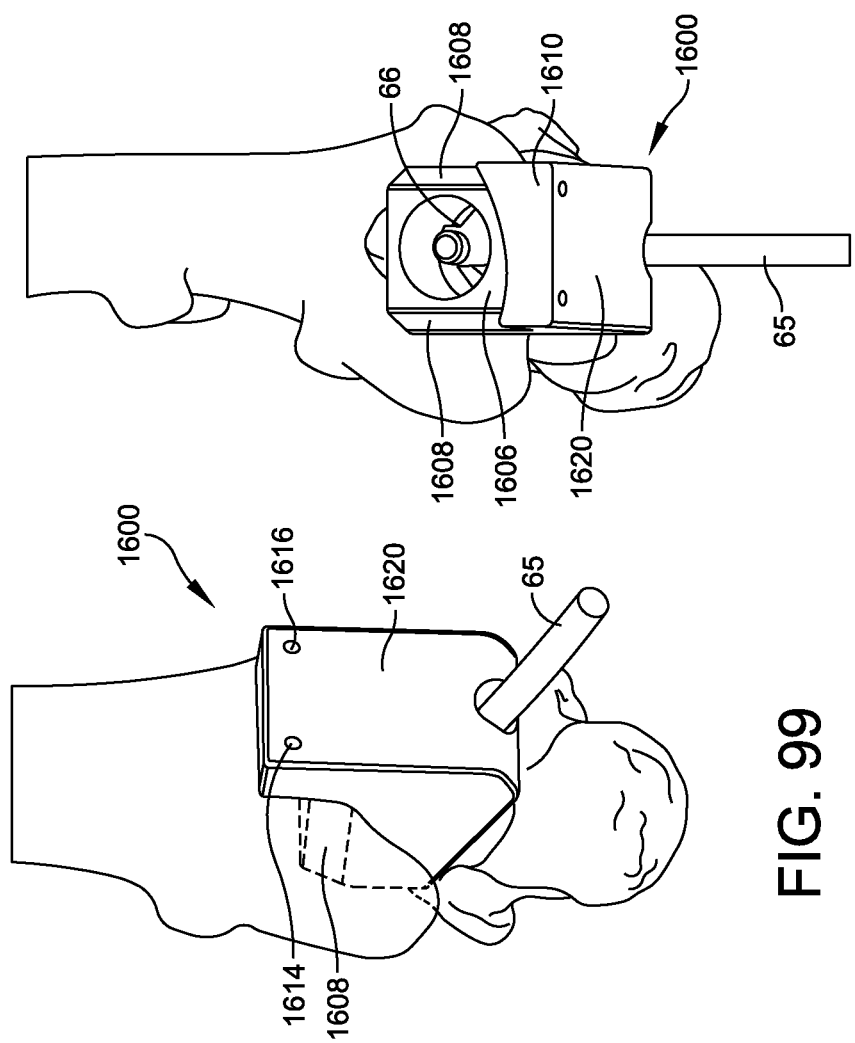
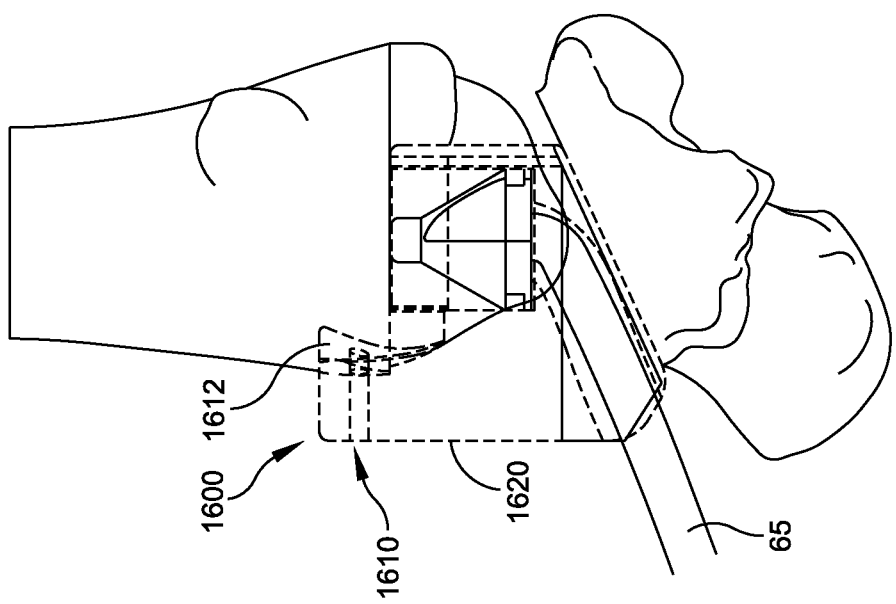
FIG. 100
FIG. 99
FIG. 98

ORTHOPEDIC SURGICAL GUIDE

CROSS REFERENCE TO RELATED APPLICATIONS

This application is a continuation of U.S. patent application Ser. No. 13/464,175, filed May 4, 2012, which is a continuation-in-part of U.S. patent application Ser. No. 13/330,091 filed on Dec. 19, 2011, which claims priority to U.S. Provisional Patent Application No. 61/425,054 filed on Dec. 20, 2010 and to U.S. Provisional Patent Application No. 61/482,657 filed on May 5, 2011, and which is a continuation-in-part of U.S. patent application Ser. No. 12/711,307 filed on Feb. 24, 2010 claiming priority to U.S. Provisional Patent Application No. 61/154,845 filed on Feb. 24, 2009, the entireties of which are herein incorporated by reference.

FIELD OF DISCLOSURE

The disclosed system and method generally relate to surgical guides. More specifically, the disclosed system and method relate to surgical guides for orthopedic procedures involving an ankle.

BACKGROUND

Total joint replacement prostheses typically include a specially designed jig or fixture to enable a surgeon to make accurate and precise bone resections in and around the joint being prepared to accept the prosthesis. The ultimate goal with any total joint prosthesis is to approximate the function and structure of the natural, healthy structures that the prosthesis is replacing. Should the prosthesis not be properly attached to the joint, i.e., an ankle or knee, the misalignment could result in discomfort to the patient, gait problems, or degradation of the prosthesis.

Many surgical procedures employ the use of intra-operative fluoroscopy to check the alignment of the intramedullary cavities that are prepared to receive the joint replacement prosthesis. However, the use of intra-operative fluoroscopy in the operating room has several drawbacks. One such drawback is that the use of fluoroscopy to check the alignment of intramedullary cavities formed during surgery increases the overall length of the surgical procedure as time is taken to acquire and evaluate the fluoroscopic images. Long surgery times lead to increased tourniquet time forth patient and therefore may increase recovery time.

Another drawback of fluoroscopy is exposing the patient and others in the operating room to the ionized radiation. For example, the U.S. Food and Drug Administration ("FDA") has issued several articles and public health advisories concerning the use of the fluoroscopy during surgical procedures. Consequently, even though steps are taken to protect the patient and other from the ionized radiation, it is virtually impossible to eliminate all risk associated with the ionized radiation.

SUMMARY

In some embodiments, a surgical device includes an elongate body extending from a proximal end to a distal end. The distal end of the elongate body defines a notch sized and configured to receive a reamer. A coupling assembly is supported by the elongate body and includes a reamer guide body disposed at the distal end of the elongate body. The reamer guide body configured to move between a first position and a second position in which the reaming guide body extends at least partially across the notch. A locking assembly is supported by the elongate body and is configured to releasably engage the coupling assembly to maintain the reamer guide body in the second position.

In some embodiments, a reamer stabilizer includes an elongate body extending from a proximal end to a distal end. The distal end of the elongate body defines a notch for receiving a reamer. A coupling assembly is supported by the elongate body and includes a reamer guide body pivotably coupled to the distal end of the elongate body. The reamer guide body is configured to move between a first position and a second position in which the reamer guide body extends at least partially across the notch. The reamer guide body includes an arcuate surface for supporting the reamer. A locking assembly is slidably supported by the elongate body. The locking assembly is configured to move between a third position and a fourth position in which the locking assembly releasably engages the coupling assembly to maintain the reamer guide body in the second position.

BRIEF DESCRIPTION OF THE DRAWINGS

These and other features and advantages of the present invention will be more fully disclosed in, or rendered obvious by, the following detailed description of the preferred embodiment of the invention, which is to be considered together with the accompanying drawings wherein like numbers refer to like parts and further wherein:

FIGS. 64 and 65 illustrate the reamer stabilizer illustrated in FIG. 63 during various stages of operation;

FIG. 84 is a side view of a flexible reaming rod and reaming head disposed within the insert illustrated in FIG. 82;

FIG. 85 is an isometric side view of the flexible reaming rod and reaming head disposed within the insert;

FIG. 86 is a front elevation view of the flexible reaming rod and reaming head disposed within the insert;

FIGS. 95-100 illustrate another example of an anterior reaming guide mount.

DETAILED DESCRIPTION

Figure 1:
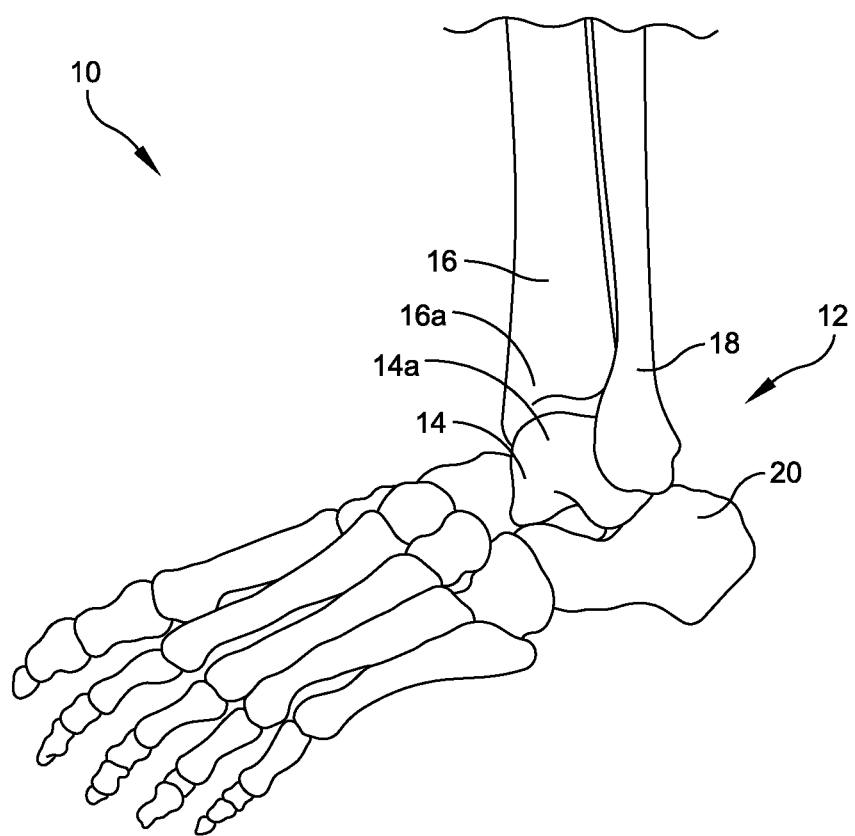
FIG. 1 illustrates the bones of a human foot and ankle.

This description of preferred embodiments is intended to be read in connection with the accompanying drawings, which are to be considered part of the entire written description. The drawing figures are not necessarily to scale and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. When only a single machine is illustrated, the term "machine" shall also be taken to include any collection of machines that individually or jointly execute a set (or multiple sets) of instructions to perform any one or more of the methodologies discussed herein. The term "operatively connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

The disclosed systems and methods advantageously utilize custom manufactured surgical instruments, guides, and/or fixtures that are based upon a patient's anatomy to reduce the use of fluoroscopy during a surgical procedure. In some instances, the use of fluoroscopy during a surgical procedure may be eliminated altogether. The custom instruments, guides, and/or fixtures are created by imaging a patient's anatomy with a computer tomography scanner ("CT"), a magnetic resonance imaging machine ("MRI"), or like medical imaging technology prior to surgery and utilizing these images to create patient-specific instruments, guides, and/or fixtures.

Although the following description of the custom patient-specific instruments are described with respect to a foot 10 and ankle 12 (FIG. 1), one skilled in the art will understand that the systems and methods may be utilized in connection with other joints including, but not limited to, knees, hips, shoulders, and the like. As shown in FIG. 1, a typical human foot 10 includes an ankle joint 12 formed between a talus 14, which is disposed on a calcaneus 20, and a tibia 16 and fibula 18.

A CT or MRI scanned image or series of images may be taken of a patient's ankle 12 (or other joint) and then converted from, e.g., a DICOM image format, to a solid computer model of the ankle including the calcaneus, talus, tibia, navicular, and fibula to determine implant alignment, type, and sizing using specialized modeling methods that are often embodied in computer software. Computer generated solid models that are derived from the data of the CT or MRI scan image will often include precise and accurate information regarding the surface contours surrounding the structures that have been imaged, e.g., the surface topography of the bones or contour of fascia that have been imaged. It will be understood that by surface topography it is meant the location, shape, size and distribution of surface features such as concavities and prominences or the like.

The methods disclosed in U.S. Pat. No. 5,768,134, issued to Swaelens et al., which is incorporated by reference herein in its entirety, have been found to yield adequate conversions of data of CT or MRI scan images to solid computer models. In some embodiments, images are made of a foot 10, i.e., the calcaneus 20, talus 14, tibia 16, and fibula 18 of a patient using a CT or MRI machine, or other digital image capturing and processing unit as is understood by one skilled in the art. The image data is processed in a processing unit, after which a model 50 is generated using the processed digitized image data as illustrated in FIGS. 2A and 2B.

Figure 2B:
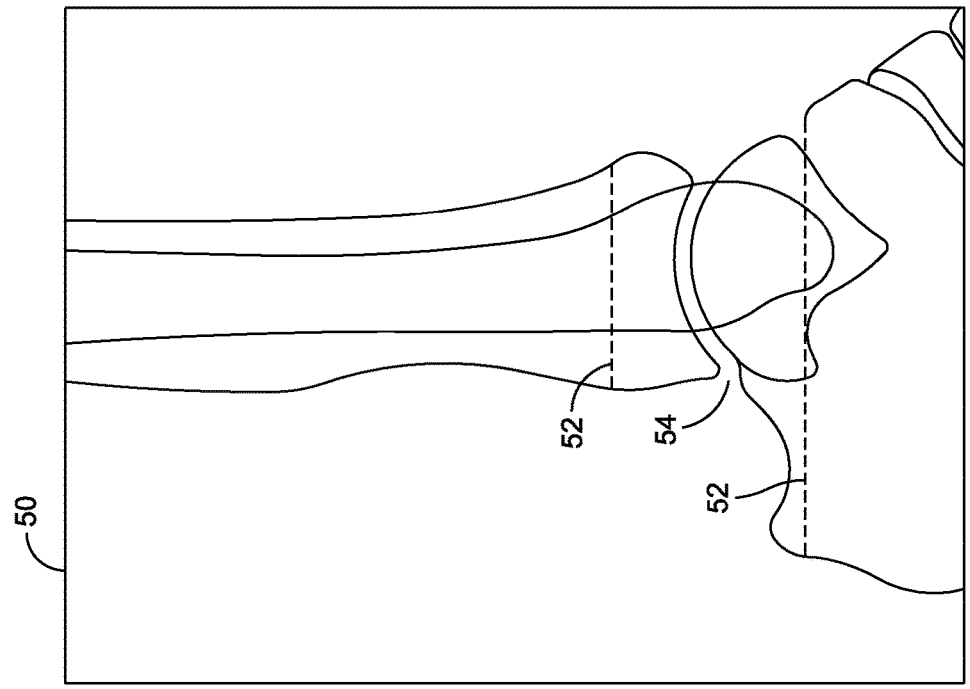
FIGS. 2A and 2B are schematic representations of a scanned image of a human foot and ankle joint.
Figure 2A:
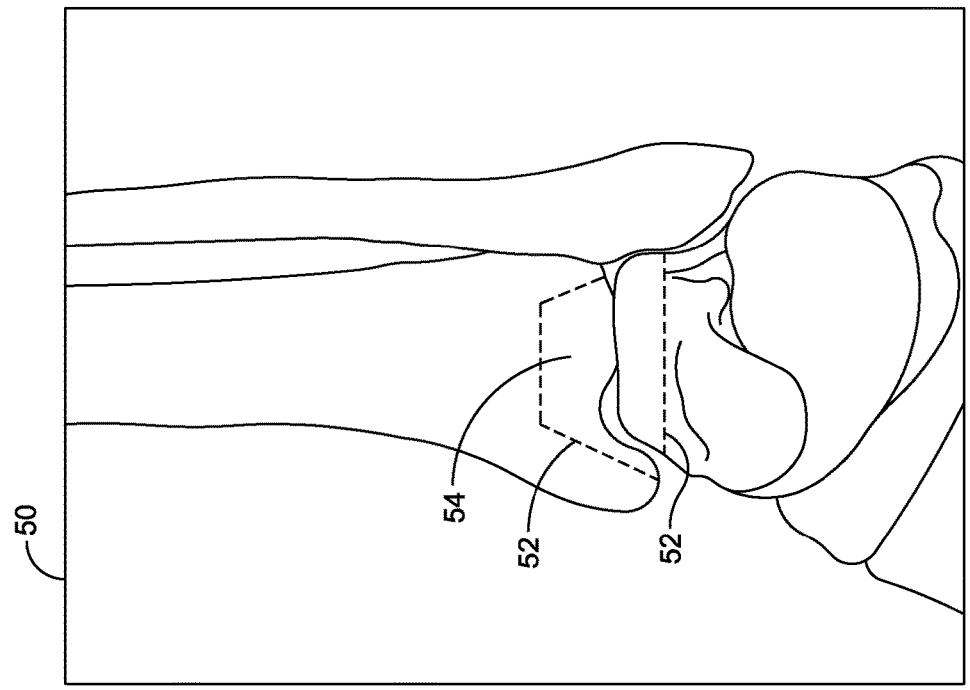

Interactive processing and preparation of the digitized image data is performed, which includes the manipulation and introduction of additional extrinsic digital information, such as, predefined reference locations 52 for component positioning and alignment so that adjustments to the surgical site 54, that will require resection during surgery, may be planned and mapped onto computer model 50 (FIGS. 2A and 2B). After the interactive processing of the digitized image data, it is possible to go back to original CAD data to obtain a higher resolution digital representation of the patient specific surgical instruments, prostheses, guides, or fixtures so as to add that digital representation to the patient's image data model.

Figure 3:
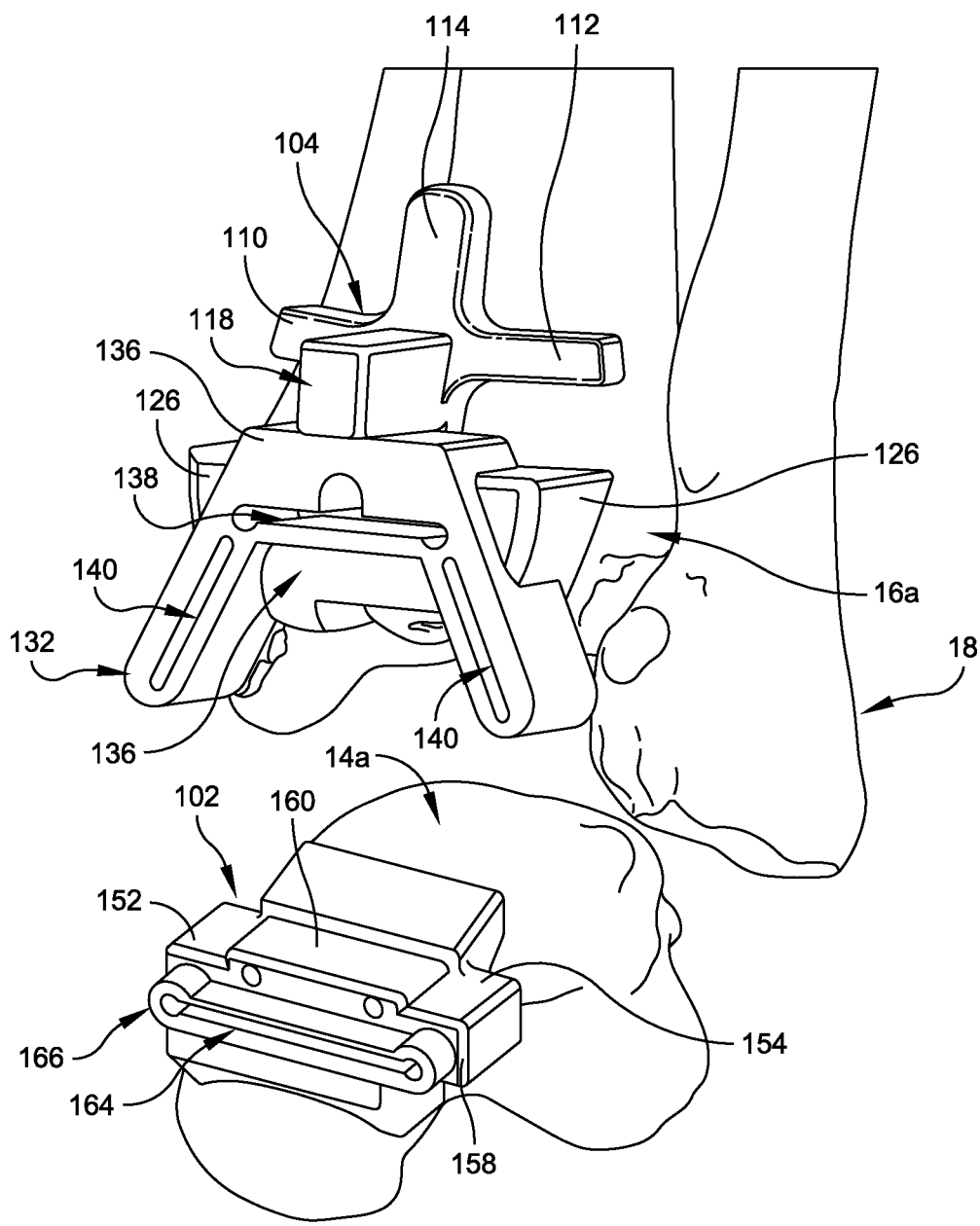
FIG. 3 is a perspective view of tibial and talar resection guides located upon portions of a tibia and a talus.

FIG. 3 illustrates a pair of custom cutting guides for an ankle replacement surgery including a tibial resection guide mount 100 and a talar resection guide mount 102, which are formed and mounted to the patient's lower tibia 16*a* and upper talus 14*a*. A custom tibial drill guide mount 200 (FIGS. 16-20) is also formed and configured to be received within ankle space created by using the custom tibial and talar resection guide mounts 100, 102. Although custom cutting guides are described for preparing a patient's talus, tibia, and femur, one skilled in the art will understand that other cutting guides may be implemented and that custom guides may be created for other joints including, but not limited to, the knee, hip, shoulder, or other joint.

Figure 4:
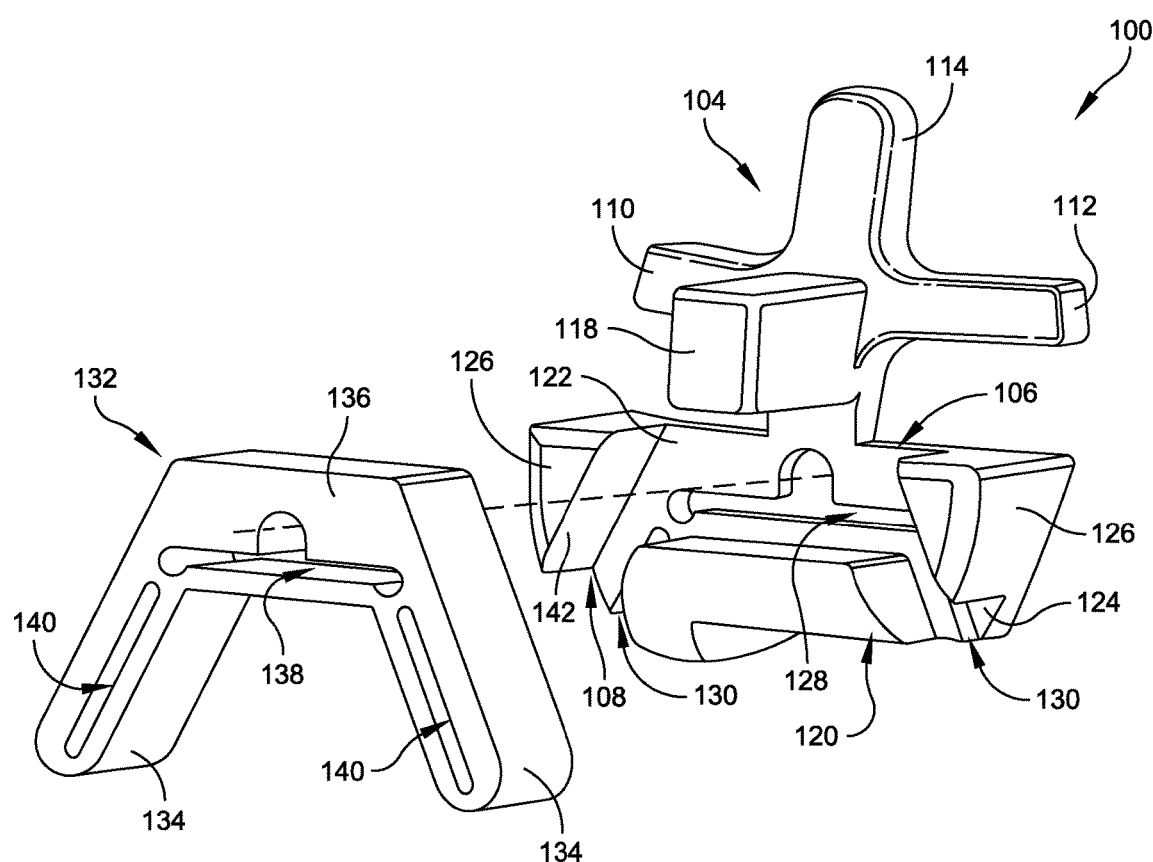
FIG. 4 is an exploded perspective view of a tibial cutting guide mount and tibial resection guide.
Figure 7:
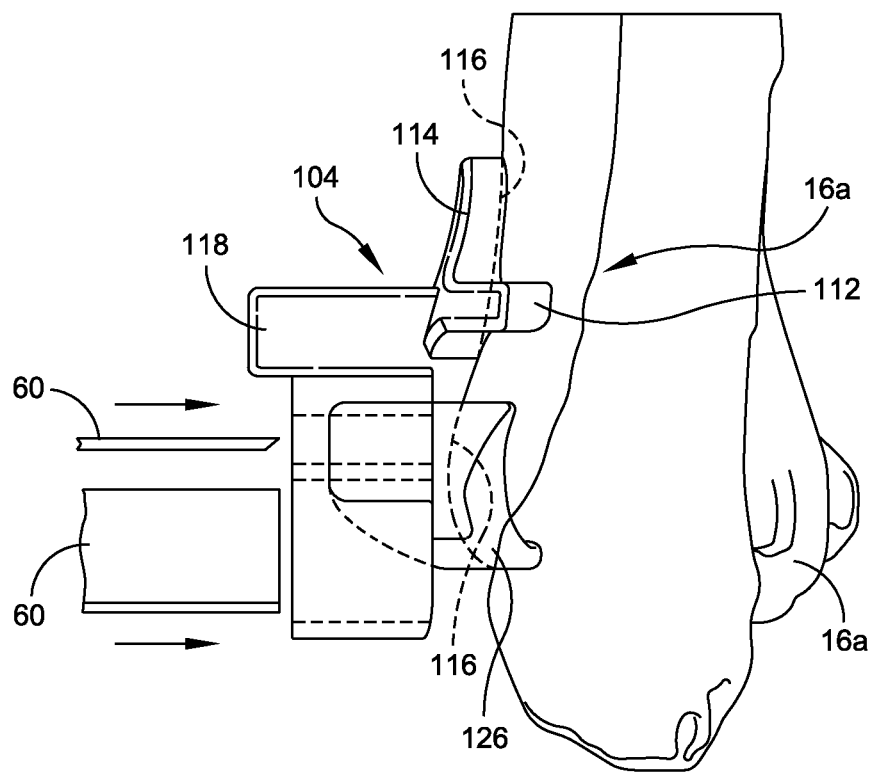
FIG. 7 is a side elevational view of a tibial cutting guide disposed within a tibial cutting guide mount located on an inferior portion of a tibia during resection of the tibia.

Tibial resection guide mount 100 illustrated in FIG. 3 is formed from a resilient polymer material of the type that is suitable for use in connection with stereo lithography, selective laser sintering, or like manufacturing equipment. Resection guide mount 100 includes a unitary body including a cruciform tibial yolk 104 projecting upwardly from a base 106 that further defines a guide receptacle recess 108 as best seen in FIG. 4. Cruciform yolk 104 includes a pair of spaced apart arms 110, 112 that project outwardly from a central post 114. Arms 110, 112 and central post 114 each have a conformal bone engaging surface 116 that is complementary to the contours of a corresponding portion of the patient's lower tibia 16*a* as illustrated in FIG. 7. Through the previously discussed imaging operations, conformal bone engaging surfaces 116 of arms 110, 112 and central post 114 are configured for complementary matching with anatomical surface features of a selected region of the patient's natural bone. For tibial resection guide mount 100, the selected bone region comprises the lower surfaces of the patient's tibia 16*a*.

Figure 5:
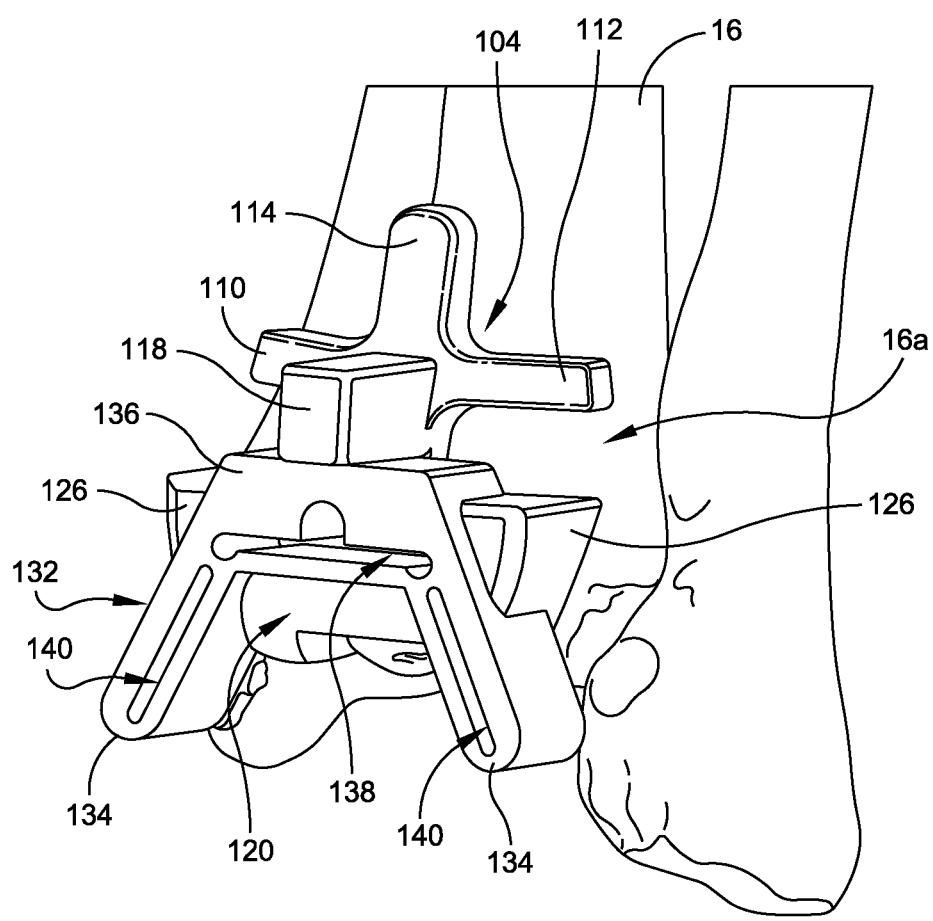
FIG. 5 is a perspective view of a tibial cutting guide disposed within a tibial cutting guide mount located on an inferior portion of a tibia.

As best seen in FIGS. 3-5, a pilot block 118 projects outwardly from central post 114, adjacent to the intersection of arms 110,112. A support block 120 (FIG. 4) is located on base 106 in spaced relation to pilot block 118. Guide receptacle recess 108 is defined by a pair of wings 122,124 that extend outwardly from either side of central post 114 in opposite directions on base 106, with support block 120 located between them. Each wing 122, 124 includes a respective pylori 126 projecting outwardly from base 106 so as to provide lateral support for tibial resection guide 132 (FIGS. 4 and 5). An elongate slot 128 is defined transversely in a central portion of base 106 below pilot block 118, but above support block 120. Each wing 122, 124 also defines a respective slot 130 that is oriented at an angle relative to central post 114. In some embodiments, slots 130 are disposed at a non-perpendicular angle relative to central post 114, although one skilled in the art will understand that slots 130 may be disposed at perpendicular angles with respect to the direction in which central post 114 extends. Slots 128 and 130 are sized and shaped to allow a typical surgical saw 60 (FIG. 7) of the type often used for bone resection, to pass through from a correspondingly positioned and sized slot in resection guide 132 without contact, or with only incidental contact with resection guide mount 100.

Referring again to FIG. 4, tibial resection guide 132 includes a pair of arms 134 that project downwardly and outwardly in diverging angular relation from the ends of a bridge beam 136. The shape of tibial resection guide 132 is complementary to the shape of guide receptacle recess 108 as defined by the inwardly facing surfaces of pilot block 118, support block 120, and pylons 126. Bridge beam 136 defines an elongate slot 138 that aligns with slot 128 when tibial resection guide is coupled to and supported by resection guide mount 100. Arms 134 each define a respective slot 140 that align with a respective slot 130.

The inwardly facing surfaces 142 of pilot block 118, support block 120, and pylons 126, that together define guide receptacle recess 108, have a shape that is complementary to the outer profile of tibial resection guide 132. Guide receptacle recess 108 is sized so as to accept tibial resection guide 132 with a "press-fit". By press-fit it should be understood that the inwardly facing surfaces 142 of pilot block 118, support block 120, and pylons 126 are sufficiently resilient to deflect or compress elastically so as to store elastic energy when tibial resection guide 132 is pushed into guide receptacle recess 108. Of course, it will also be understood that tibial resection guide 132 will have an outer peripheral shape that is complementary to the circumferential shape of guide receptacle recess 108, but slightly larger in size, for press-fit embodiments. Also, tibial resection guide 132 may be retained within guide receptacle recess 108 by only frictional engagement with the inwardly facing surfaces of pilot block 118, support block 120, and pylons 126. In some embodiments, tibial resection guide 132 can simply slide into guide receptacle recess 108 without operative contact or only incidental engagement with the inwardly facing surfaces of pilot block 118, support block 120, and pylons 126.

Figure 9:
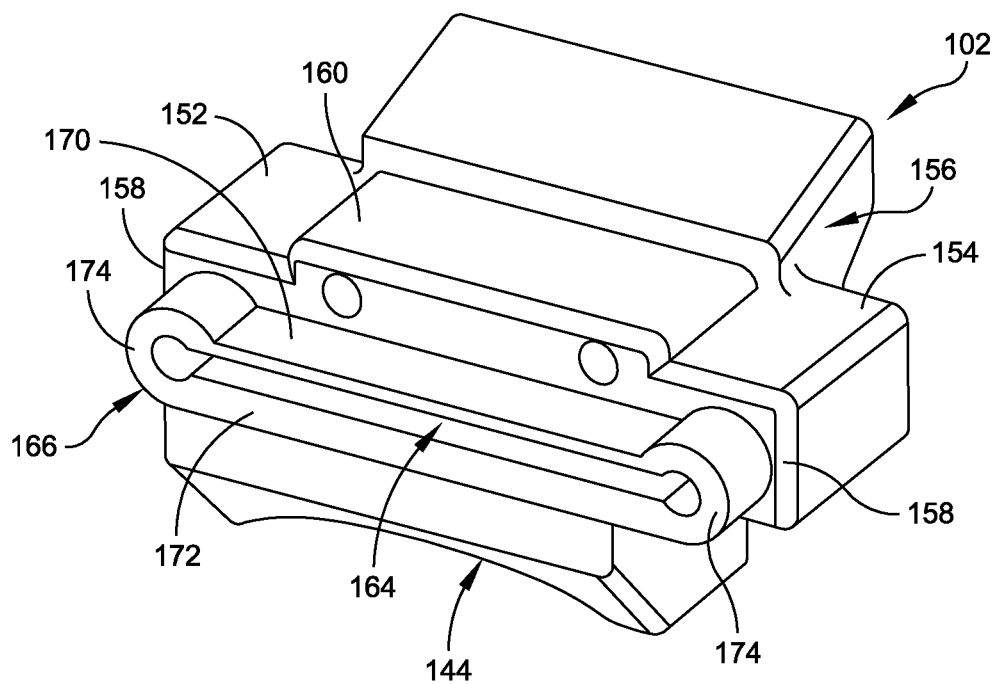
FIG. 9 is a perspective view of a talar cutting guide disposed within a talar cutting guide mount.
Figure 10:
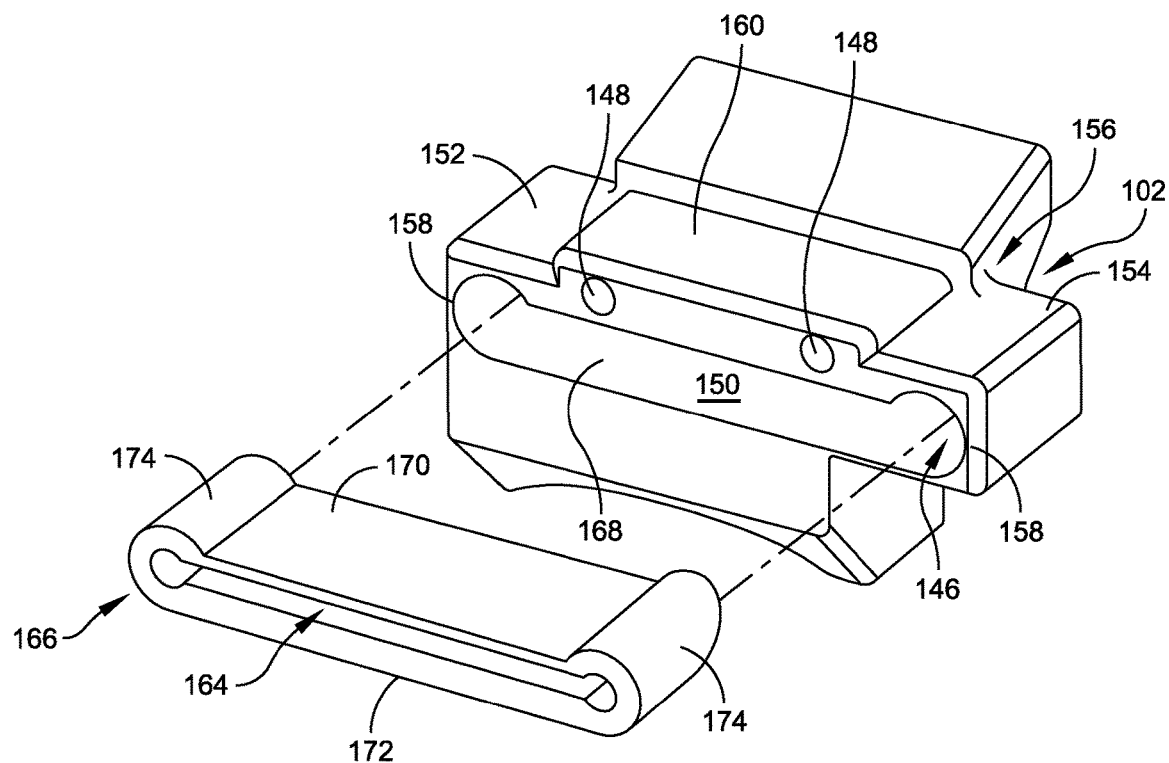
FIG. 10 is an exploded perspective view of the talar cutting guide mount and the talar cutting guide illustrated in FIG. 9.
Figure 11:
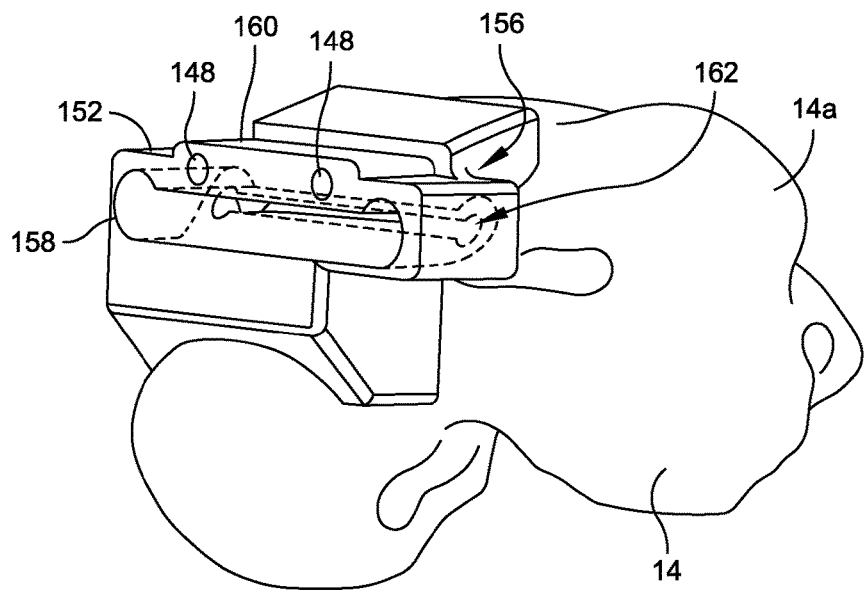
FIG. 11 is a perspective view of the talar cutting guide disposed within the talar cutting guide mount located on a superior portion of a talus.
Figure 13:
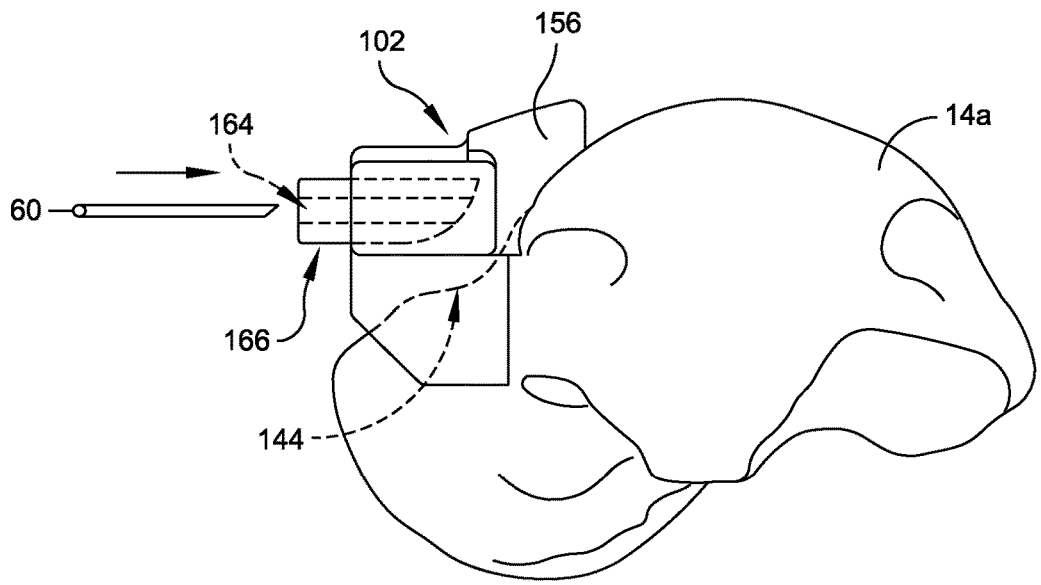
FIG. 13 is a side perspective view of the talar cutting guide disposed within the talar cutting guide mount located on a superior portion of a talus during resection of the talus.

Referring now to FIGS. 9 and 10, a talar resection guide mount 102 is formed from a resilient polymer material of the type that is suitable for use in connection with stereo lithography, selective laser sintering, or the like manufacturing equipment, e.g., a polyamide powder rapid prototype material is suitable for use in connection with selective laser sintering. Talar resection guide mount 102 also includes a conformal bone engaging surface 144 that is complementary to the contours of a corresponding portion of the patient's upper talus 14*a* (FIGS. 11 and 13). Through the previously discussed imaging operations, conformal bone engaging surface 144 of talar resection guide mount 102 is configured for complementary matching with anatomical surface features of a selected region of the patient's natural bone. For talar resection guide mount 102, the selected bone region comprises the outer, upper surfaces of the patient's talus.

Talar resection guide mount 102 comprises a unitary block that defines a central guide receptacle recess 146 and a pair of through-bores 148 (FIG. 10). Guide receptacle recess 146 is defined by the inwardly facing surfaces 150 of a pair of wings 152, 154 that project outwardly, in opposite directions from a base 156. Each wing 152,154 includes a pylori 158 projecting upwardly to support guide housing 160 such that an elongate slot 162 is defined within base 156 and below guide housing 160 (FIGS. 10 and 11). Slot 162 is sized and shaped to allow a typical surgical saw 60, of the type often used for bone resection, to pass through from a correspondingly positioned and sized slot 164 in talar resection guide 166 without contact, or with only incidental contact with talar resection guide locator 102 (FIGS. 11 and 13). An annular wall 168, having a shape that is complementary to the outer profile of talar resection guide 166, projects outwardly in substantially perpendicular relation to a back wall and so as to further defines guide receptacle recess 146.

Still referring to FIGS. 9 and 10, talar resection guide 166 includes a pair of confronting, parallel plates 170, 172 that define elongate slot 164 between them, and are joined to one another at their ends by wings 174. In this way, the shape of talar resection guide 166 is complementary to the shape of guide receptacle recess 146 as defined by the inwardly facing surfaces 150 of wings 152, 154, base 156, and pylons 158. Guide receptacle recess 146 is sized so as to accept talar resection guide 166 with a press-fit. Of course, it will also be understood that talar resection guide 166 will have an outer peripheral shape that is complementary to the circumferential shape of guide receptacle recess 146, but slightly larger in size, for press-fit embodiments. Also, talar resection guide 166 may be retained within guide receptacle recess 146 by only frictional engagement with the inwardly facing surfaces 150 of wings 152, 154, base 156, and pylons 158. In some embodiments, talar resection guide 166 can simply slide into guide receptacle recess 146 without operative contact or only incidental engagement with the inwardly facing surfaces 150 of wings 152, 154, base 156, and pylons 158.

Figure 8:
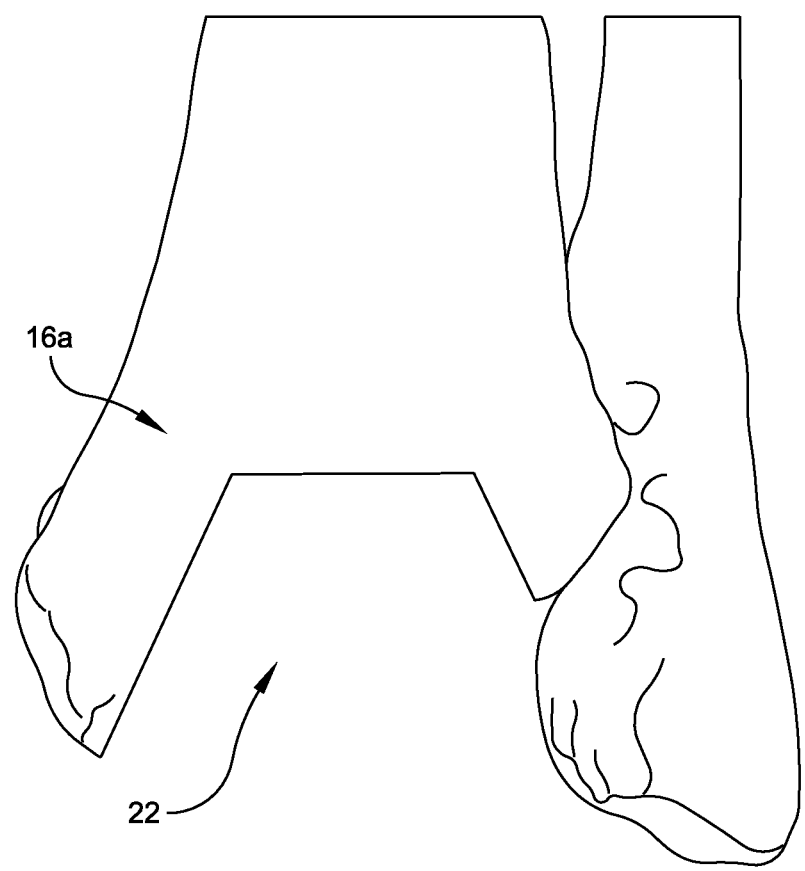
FIG. 8 is a schematic representation of a resected tibia following application and use of the tibial cutting guide and tibial cutting guide mount.

Tibial drill guide mount 200 illustrated in FIGS. 16-20 also may be fabricated from a resilient polymer material of the type that is suitable for use in connection with stereo lithography, selective laser sintering, or the like manufacturing equipment, e.g., a polyamide powder repaid prototype material is suitable for use in connection with selective laser sintering. As shown in FIGS. 16-20, tibial drill guide mount 200 includes a somewhat rectangular body 204 that defines an aperture 206 that extends from a top surface 208 of body 204 to a bottom surface 210 of body 204. Top surface 208 of body 204 may include a pair of chamfers 212 that are sized and configured to be mate against the resected surfaces of the lower tibia 16a (FIG. 8). Put another way, the top or upper surface 208 of body 204, including chamfers 212, is complementary to the geometry and locations of slots 138 and 140 of tibial resection guide 132.

Front side 214 of body 204 defines one or more blind holes 216. As illustrated in the embodiment shown in FIG. 17, body 204 may define three blind holes 216-1, 216-2, and 216-3. In some embodiments, blind holes 216-1 and 216-2 may be reamed holes that are sized and configured to receive a dowel pin, and blind hole 216-3 may also be a reamed hole for receiving a dowel pin or blind hole 216-3 may be threaded for engaging a screw as described below.

Figure 20:
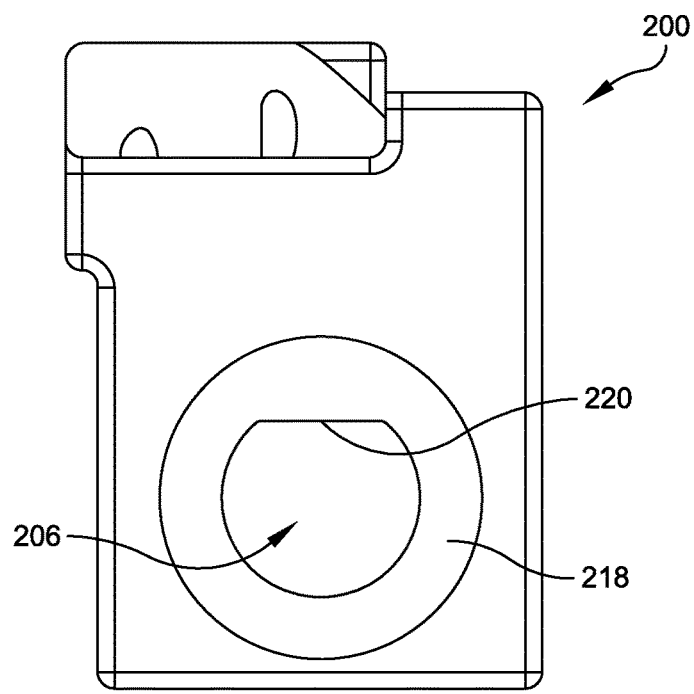
FIG. 20 is a top elevational view of the tibial drill guide mount illustrated in FIG. 16.

Aperture 206 may have a circular cross sectional area and include a shoulder 218 having a reduced diameter compared to aperture 206 and includes an anti-rotational feature 220 as best seen in FIG. 20. Anti-rotational feature 220 of shoulder 218 may include one or more flats or other geometric structure(s) to prevent tibial drill guide 202 from rotating with respect to tibial drill guide mount 200 when tibial drill guide 202 is disposed within aperture 206.

Extending from body 204 of tibial drill guide mount 200 are tibial engagement structure 222 and talar engagement structure 224. The outer surface 226 of tibial engagement structure 222 may have a rectangular shape that is substantially planar, and the internal and substantially conformal engagement surface 228 of tibial engagement structure 222 may be somewhat convex for engaging the tibia 16 of the patient. Tibial engagement structure 222 may define one or more holes 230 for receiving a k-wire or pin as described below.

Figure 14:
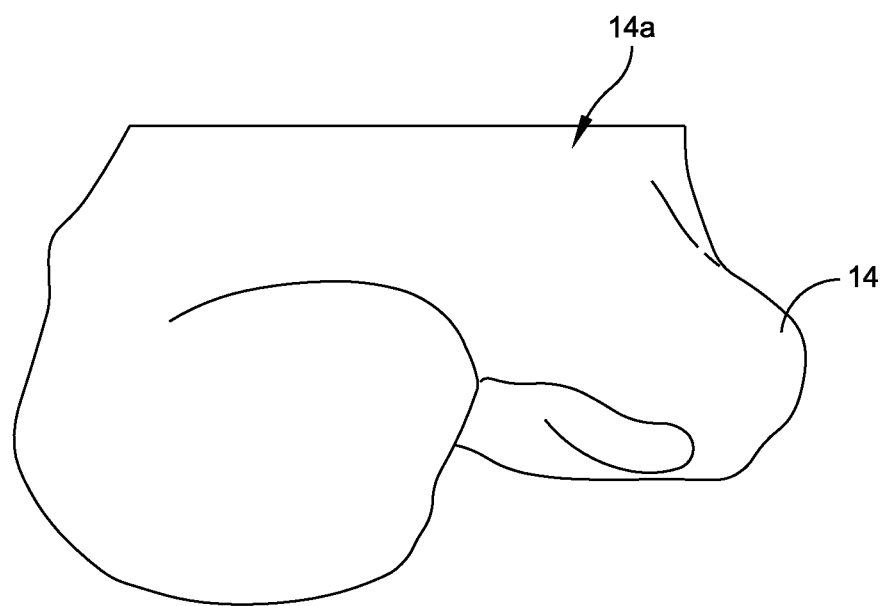
FIG. 14 is a schematic representation of a resected talus following application and use of the talar cutting guide and talar cutting guide mount.

Talar engagement structure 224 may also include a substantially planar and rectangular outer surface 232. The lower portion 234 of talar engagement structure 224 may be a conformal surface having a geometry that matches the geometry of the talar bone 14 (FIG. 14). Talar engagement structure 224 may also define one or more holes 236 sized and configured to receive a k-wire as described below.

Figure 21:
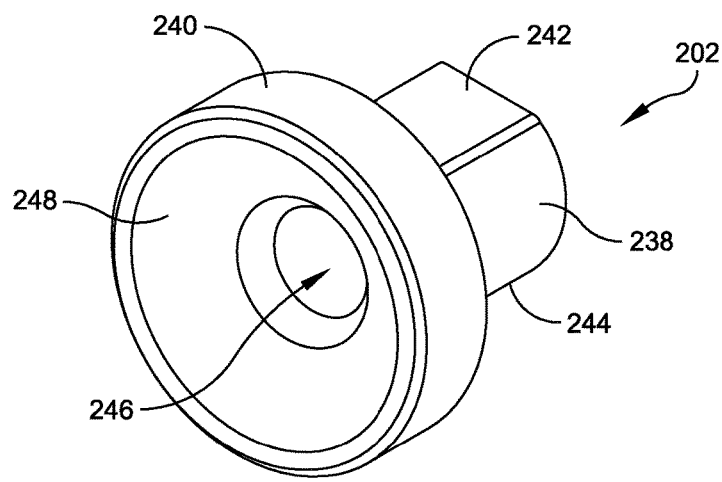
FIG. 21 is a perspective view of one example of a tibial drill guide.
Figures 22, 23:
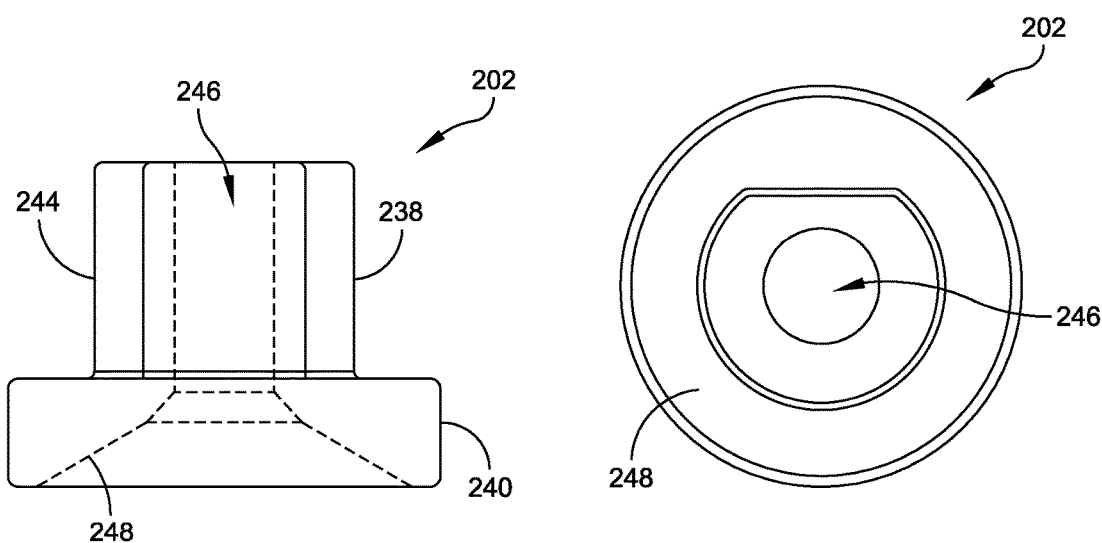
FIG. 22 is a side elevational view of the tibial drill guide illustrated in FIG. 21.
FIG. 23 is a top elevational view of the tibial drill guide illustrated in FIG. 21.

Tibial drill guide 202 illustrated in FIGS. 21-23 is preferably fabricated from a material having more structural integrity than tibial drill guide mount 200 to enable drill guide 202 to guide a drill bit without being damaged. Examples of materials include, but are not limited to, metals, ceramics, or the like. Drill guide 202 has a cylindrically shaped first portion 238 that is sized and configured to be received within the portion of aperture 206 that extends through the shoulder or reduced diameter area 218. A second portion 240 of drill guide 202 has a larger cross-sectional diameter than first portion 238 and is sized and configured to be received within aperture 206 of tibial drill guide mount 200. A flat 242, which is best seen in FIGS. 21 and 23, is formed along an exterior surface 244 of first portion 238 of drill guide 202. The internal surface 248 of second portion 240 of tibial drill guide 202 has a conical shape that intersects and communicates with aperture 246 such that a drill or reamer may be received through drill guide 202.

As with the digital image models 50 disclosed above, and considering a generalized digital model of a tibial resection guide mount 100 added to the patient's lower tibia image data, the anatomic surface features of the patient's lower tibia, e.g., the surface topography, may be complementarily mapped onto each of conformal bone engaging surfaces 116 of arms 110, 112, and central post 114, i.e., the surfaces that will engage the bones unique surface topography, of tibial resection guide mount 100. It will be understood that complementary mapping of the digital images results in localized prominences on the surface of a bone becoming localized concavities on conformal bone engaging surfaces 116 of arms 110, 112, and central post 114 of tibial resection guide mount 100, while localized concavities on the surface of a bone become localized prominences on conformal bone engaging surfaces 116 of arms 110, 112, and central post 114.

Each of conformal bone engaging surfaces 116 of arms 110, 112, and central post 114 of resection guide mount 100 is redefined with a complementary, substantially mirror image of the anatomic surface features of a selected region of the patient's lower tibia 16a. As a consequence of this complementary bone surface mapping, tibial resection guide mount 100 releasably "locks" on to the complementary topography of the corresponding portion of the patient's natural tibia without the need for other external or internal guidance fixtures. In other words, the mating of bone surface asperities in their corresponding concavities formed in conformal bone engaging surfaces 116 of tibial resection guide mount 100 ensures that little or no relative movement, e.g., slipping sideways, occurs between tibial resection guide mount 100 and the tibial surface.

A substantially identical mapping is carried out in connection with the design of a patient specific talar resection guide mount 102 and tibial drill guide mount 200. Notably, the mapping for the design of tibial drill guide mount 200 is performed by extrapolating where the resections to the tibia 16 and talus 14 will be made using tibial and talar resection guide mounts 100 and 102 and mapping the tibial drill guide mount 200 onto the extrapolated geometry of the tibia and talus.

A visual presentation of the virtual alignment results between the patient's lower tibia 16*a* and resection guide mount 100, the patient's upper talus 14*a* and resection guide mount 102, and the proposed resected area that that is to be created by resecting the talus 14 and tibia utilizing the tibial resection guide mount 100 and the talar resection guide mount 102 are created and forwarded to the surgeon to obtain approval of the results prior to manufacturing. Additionally, the surgeon may be provided with a visual representation of the virtual alignment results between the proposed resected joint space and tibial drill guide mount 200 are created and forwarded to the surgeon to obtain approval of the results prior to manufacturing. Upon receipt of the surgeon's approval, resection guide mount 100, resection guide mount 102, and tibial drill guide mount 200 are manufactured and returned to the surgeon for use in the surgery.

Figure 6:
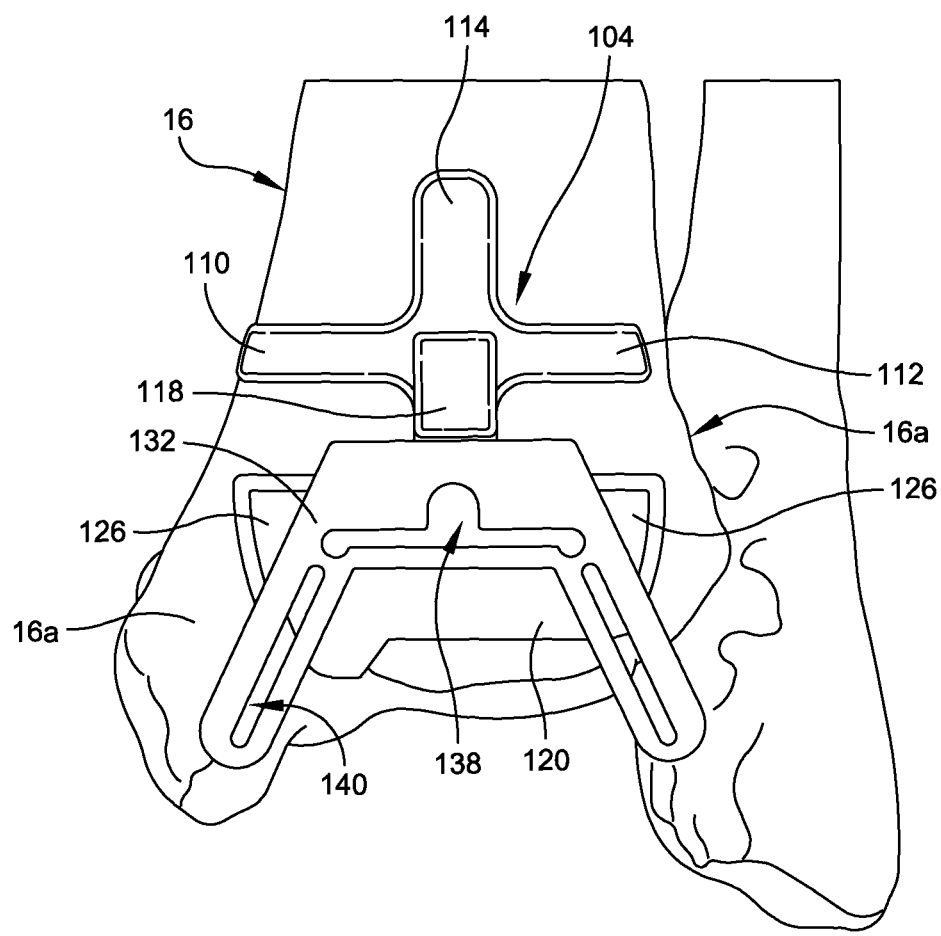
FIG. 6 is a front elevational view of a tibial cutting guide disposed within a tibial cutting guide mount located on an inferior portion of a tibia.

During a total ankle replacement, for example, the surgeon makes an anterior incision to gain initial access to the ankle joint. The surgeon orients tibia resection guide mount 100 on lower tibia 16*a* until the conformal bone engaging surfaces 116 of arms 110, 112 and central post 114 of tibial resection guide mount 100 securely engage one another so as to releasably "interlock" with the topography of the exposed surface of lower tibia 16*a* as best seen in FIGS. 5-7. With tibial resection guide mount 100 locked onto the patient's lower tibia 16*a*, a surgeon press-fits an appropriately configured distal resection guide 132 in guide receptacle recess 108 of tibial resection guide mount 100. This results in the resection guide mount 100 being sandwiched between the resection guide 132 and the patient's bone tibia 16*a* (FIGS. 5 and 6). With the resection guide mount 100 accurately positioned with respect to the selected bone region and resection guide mount 100 construct appropriately secured to the patient's bone by virtue of the mating of bone surface asperities in their corresponding concavities formed in conformal bone engaging surfaces 116, the surgeon uses a conventional surgical blade 60 and the resection slots 128 and 130 of resection guide 132 to resect the patient's bone 16 (FIGS. 7 and 8).

In a similar fashion, when talar resection guide mount 102 is added to the patient's talar image data, the anatomic surface features of the patient's upper talus, e.g., the surface topography, may be complementarily mapped onto conformal bone engaging surface 144. It will again be understood that complementary mapping of the digital images results in localized prominences on the surface of a bone becoming localized concavities on conformal bone engaging surface 144, while localized concavities on the surface of a bone become localized prominences on conformal bone engaging surface 144. In this way, conformal bone engaging surface 144 is redefined with a complementary, substantially mirror image of the anatomic surface features of a selected region of the patient's lower tibia. As a consequence of this complementary bone surface mapping, talar resection guide mount 102 releasably "locks" on to the complementary topography of the corresponding portion of the patient's natural talus without the need for other external or internal guidance fixtures.

Figure 12:
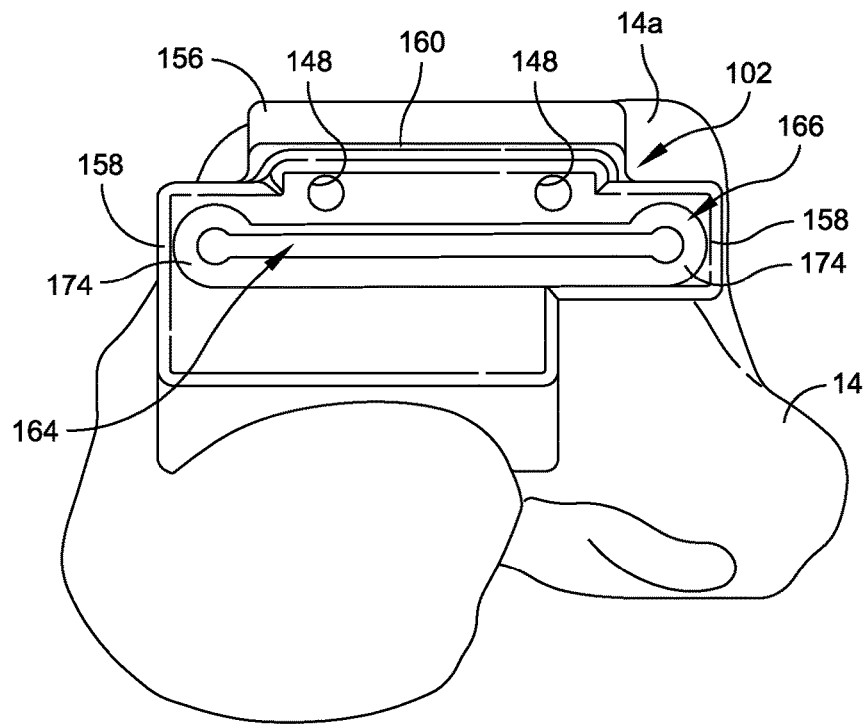
FIG. 12 is a front elevational view of the talar cutting guide disposed within the talar cutting guide mount located on a superior portion of a talus.

To continue the total ankle replacement the surgeon orients resection guide mount 102 on upper talus 14*a* until conformal bone engaging surface 144 of resection guide mount 102 "locks" to the topography of the exposed surface of upper talus 14*a* (FIG. 11). With resection guide mount 102 locked onto the patient's upper talus, a surgeon press-fits an appropriately configured distal resection guide 166 in guide receptacle recess 146 of talar resection guide mount 102. This results in resection guide mount 102 being sandwiched between resection guide 166 and the patient's bone 14 (FIGS. 12 and 13). With the resection guide mount 102 accurately positioned with respect to the selected bone region and resection guide 166 and guide mount 102 appropriately constructed and secured to the patient's bone, by virtue of the mating of bone surface asperities in their corresponding concavities formed in conformal bone engaging surfaces 144, the surgeon uses a conventional surgical blade 60 and the resection slot 164 of resection guide 166 to resect the patient's bone 14 (FIGS. 13 and 14).

Figure 15:
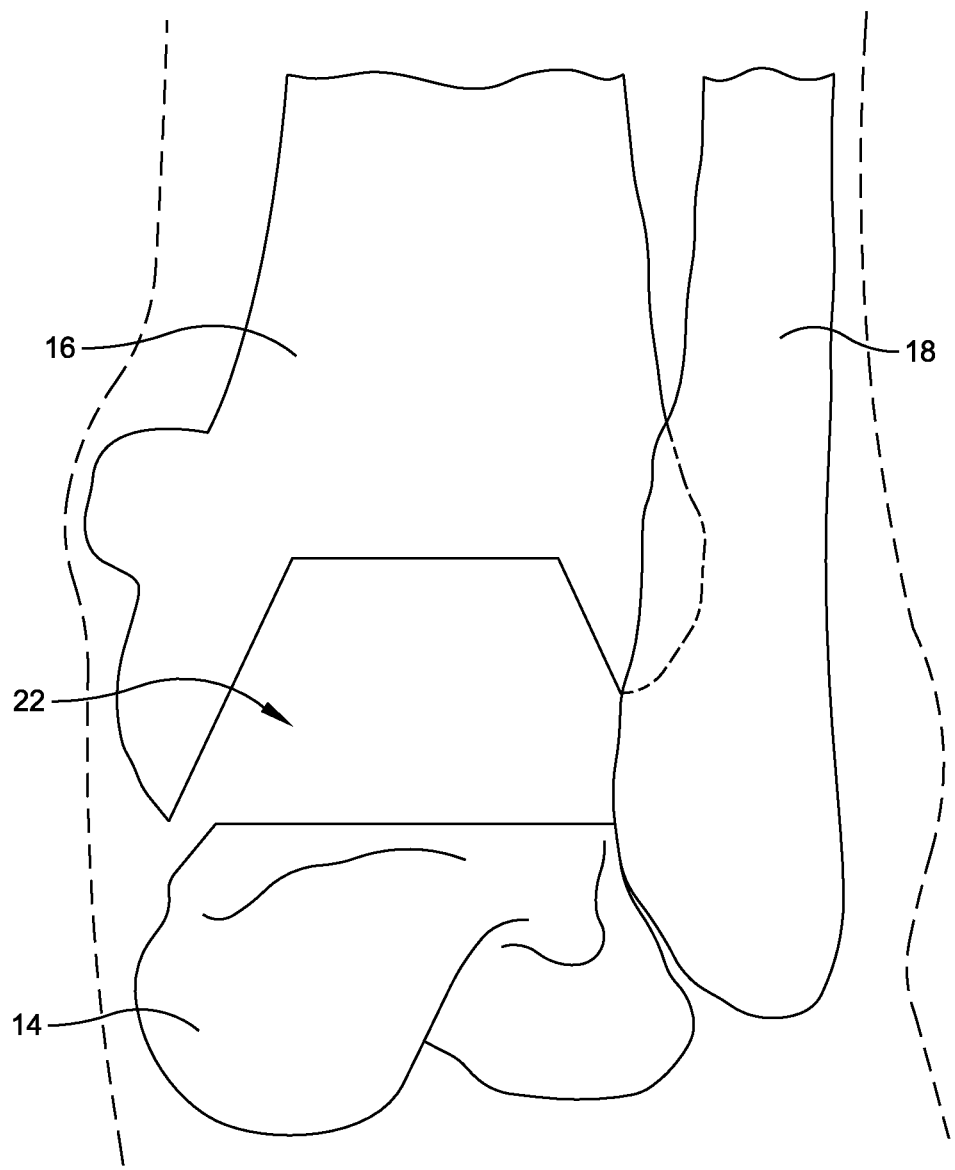
FIG. 15 is a schematic representation of a resected joint space following application and use of the talar and tibial cutting guide mounts and cutting guides.
Figure 16:
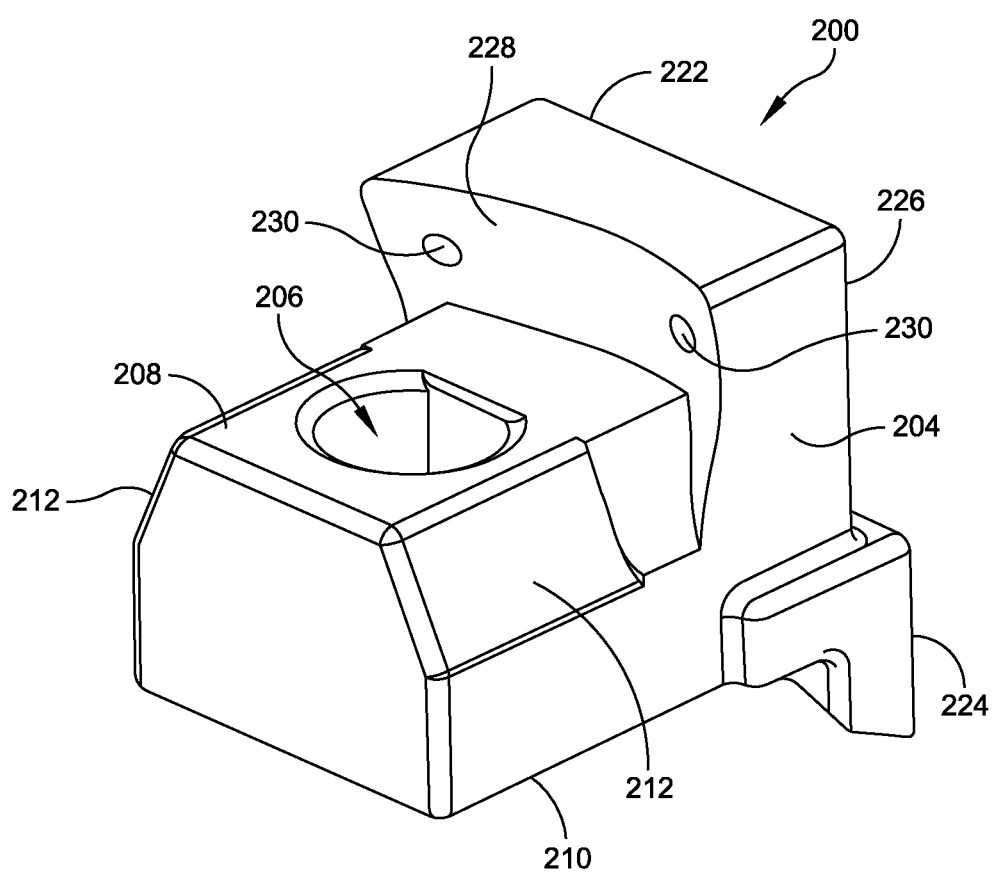
FIG. 16 is a perspective view of one example of a custom tibial drill guide mount.
Figure 17:
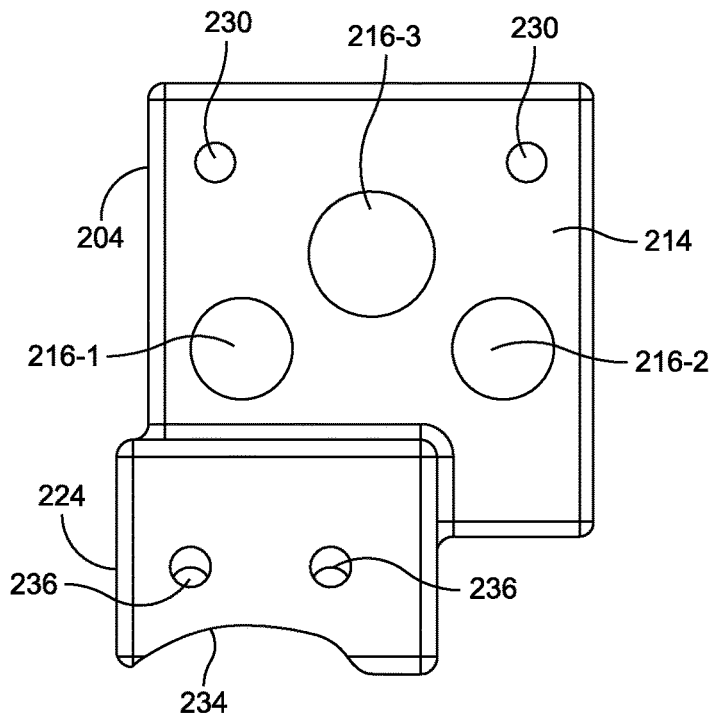
FIG. 17 is a front elevational view of the tibial drill guide mount illustrated in FIG. 16.
Figure 18:
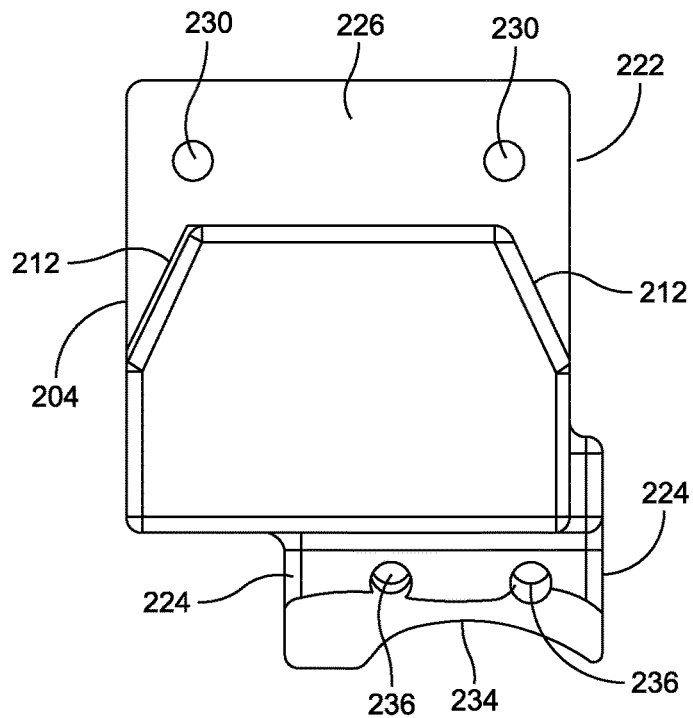
FIG. 18 is a rear elevation view of the tibial drill guide mount illustrated in FIG. 16.
Figure 19:
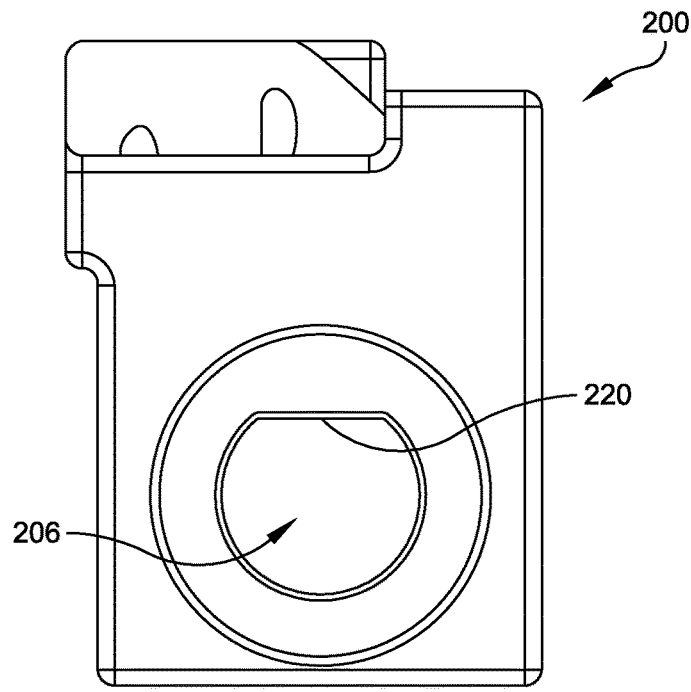
FIG. 19 is a bottom elevational view of the tibial drill guide mount illustrated in FIG. 16.
Figure 24:
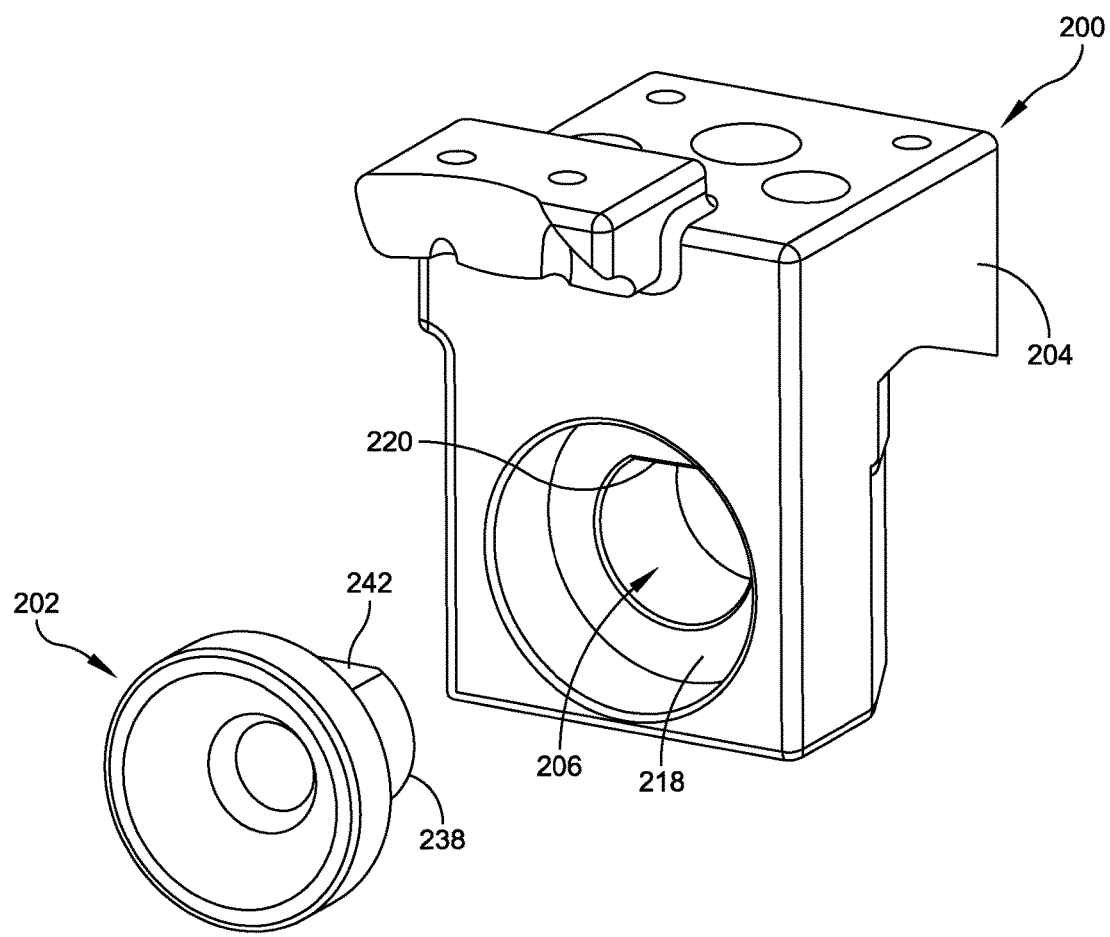
FIG. 24 is an exploded perspective view of the tibial drill guide mount and the tibial drill guide.

Once the tibia 16 and talus 14 have been resected, tibial drill guide mount 200 and tibial drill guide 202 are coupled together and installed into resected joint space 22 (FIG. 15). Tibial drill guide mount 200 and tibial drill guide 202 are coupled together by inserting first portion 238 of tibial drill guide 202 into aperture 206 defined by body 204 of tibial drill guide mount 200 (FIG. 24). Flat 242 formed on the first portion 238 of tibial drill guide 202 is aligned with anti-rotation feature 220 of shoulder 218 such that tibial drill guide 202 slides into aperture 206 until a lower surface 250 of second portion 240 of drill guide 202 contacts and abuts shoulder 218 of tibial drill guide mount 200.

Figure 25A:
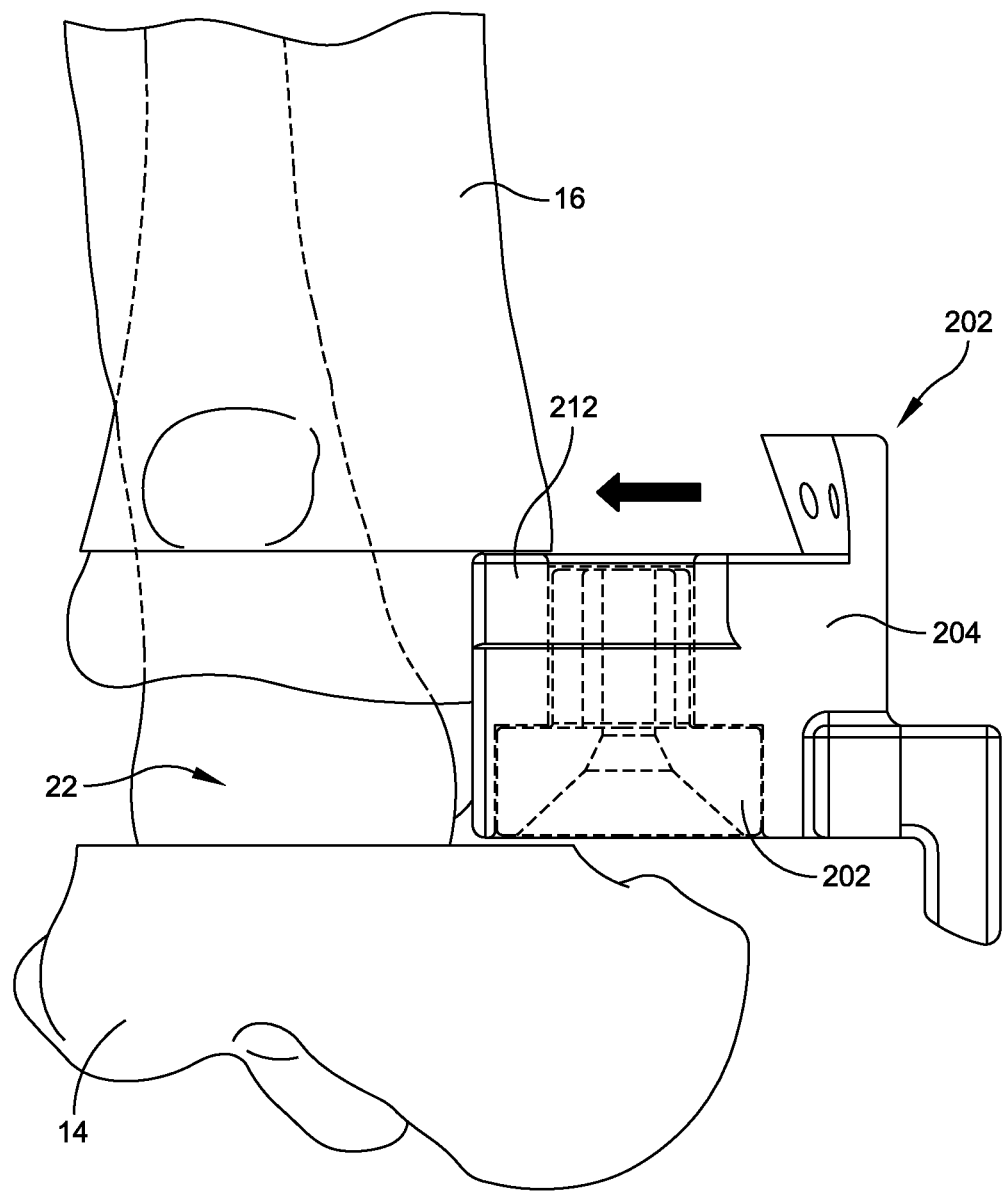
FIG. 25A is a side elevational view of the tibial drill guide disposed within the tibial drill guide mount being inserted into resected joint space.
Figure 25B:
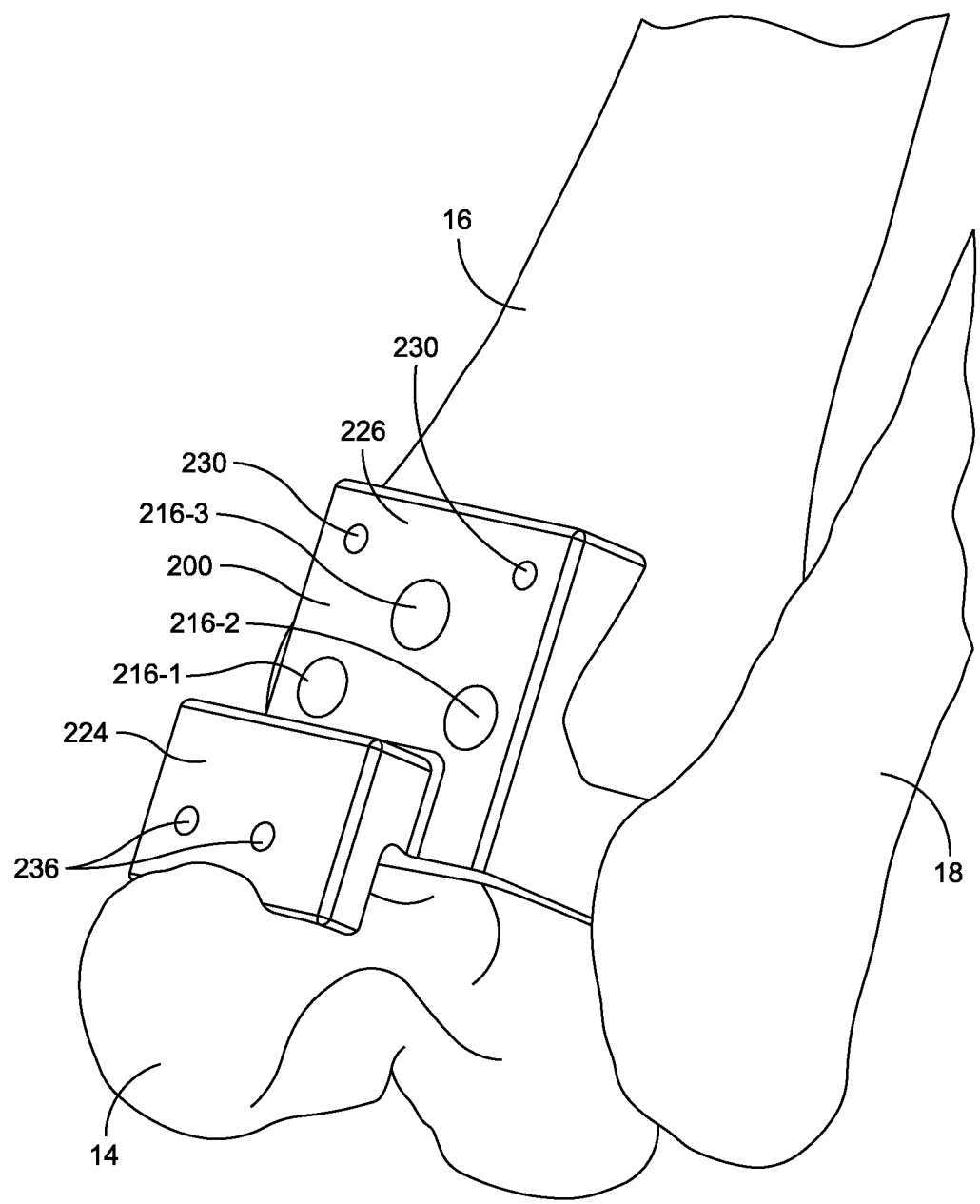
FIG. 25B is a perspective view of the assemblage of the tibial drill guide mount and tibial drill guide disposed within the resected joint space.
Figure 25C:
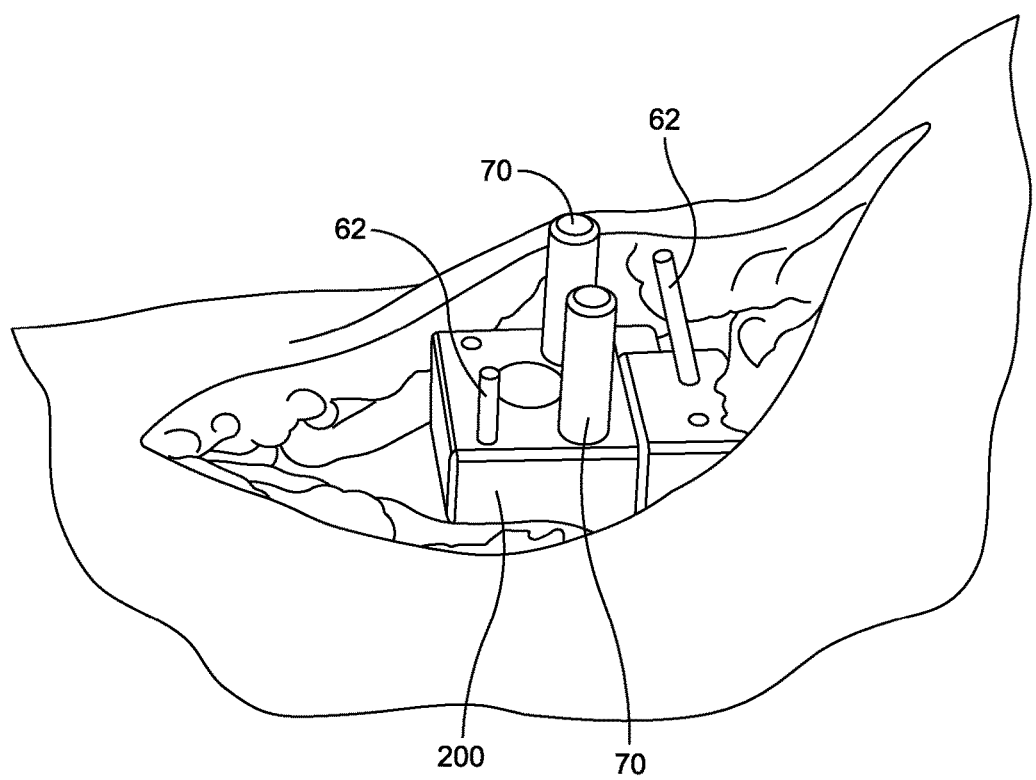
FIG. 25C is a perspective view of the assembly of the tibial drill guide mount and tibial drill guide disposed and pinned within the resected joint space.

Body 204 of tibial drill guide mount 200, in which tibial drill guide 202 is disposed, is inserted into resected joint space 22 in an anterior posterior direction with chamfers 212 sliding along resected areas of tibia 16 formed by utilizing slots 140 of tibial resection guide 132 as best seen in FIGS. 25A and 25B. The assemblage of tibial drill guide mount 200 and tibial drill guide 202 are slid into resected joint space 22 until talar engagement structure contacts talus 14. A surgeon may move tibial guide mount 200 within resected joint space until conformal surface 228 is appropriately secured to the patient's bone by virtue of the mating of bone surface asperities in their corresponding concavities formed in conformal bone engaging surface 228. Once properly located, k-wires 62 may be inserted into holes 230 and/or holes 236, respectively defined by tibial engagement structure 222 and talar engagement structure 224, to secure the assemblage of the tibial drill guide mount 200 and tibial drill guide 202 to the patient's tibia 16 and talus 14 as illustrated in FIG. 25C.

With tibial drill guide mount 200 and tibial drill guide 202 secured within resected joint space 22, the patient's leg is inserted into a foot holder and alignment tool 300. FIGS. 26-28B illustrate one example of an alignment tool 300, which serves the task of supporting the ankle joint during a prosthesis installation procedure. Alignment tool 300 includes a foot holder assembly 302 and a leg rest 304. Foot holder assembly 302 includes a foot rest 306, to which the foot is secured by a foot clamp 310 and heel clamps 308 during an prosthesis installation procedure. The calf of the leg is suitably secured to the leg rest 304 once the ankle joint has been resected and tibial drill guide mount 200 and tibial drill guide 200 have been installed. Together, foot holder assembly 302 and leg rest 304 hold the foot and ankle relative to the leg during an installation procedure.

Figure 26:
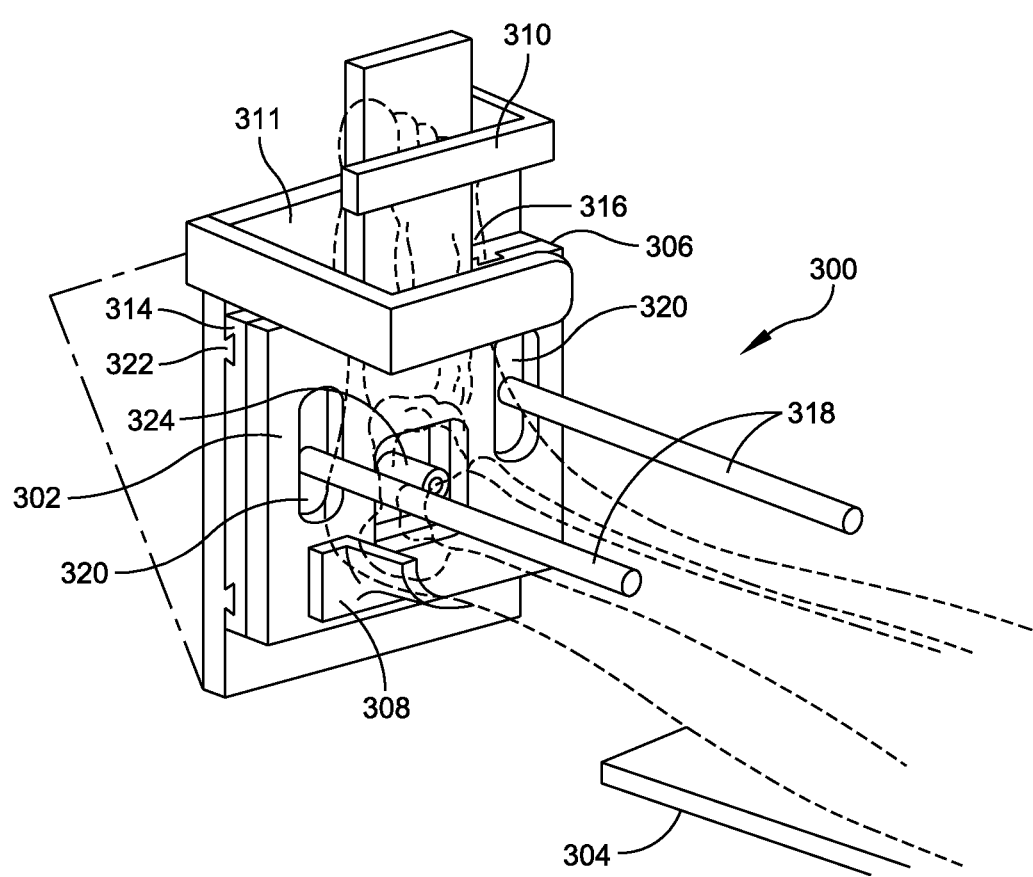
FIG. 26 is a perspective view of one example of an alignment tool.

As shown in FIG. 26, foot holder assembly 302 is sized and configured for pivoting, under control of the physician, from a vertical or upright condition (shown in solid lines in FIG. 26) toward a more horizontal or tilted condition (shown in phantom lines in FIG. 26). In the upright condition, assembly 302 serves to hold the ankle joint in a desired orientation with respect to the natural anterior-to-posterior and medial-to-lateral axes.

Figure 27:
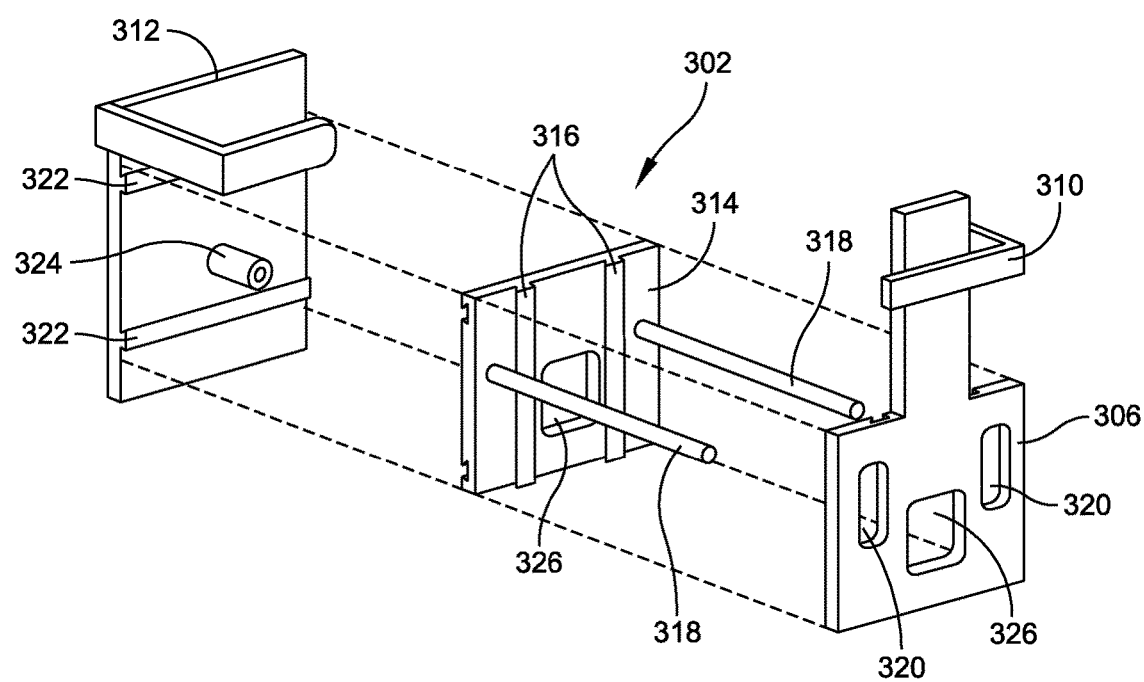
FIG. 27 is an exploded perspective view of the alignment tool illustrated in FIG. 26.

As best seen in FIG. 27, foot holder assembly 302 includes a back plate 312 and a mid-plate 314, which is sandwiched between foot rest 306 and back plate 312.

Mid-plate 314 is coupled to the foot rest 306 by sliding dovetail couplings 316 for up-and-down (i.e., vertical) movement relative to foot rest 306. A pair of oppositely spaced alignment rods 318 is carried by the mid-plate 314.

Figure 28A:
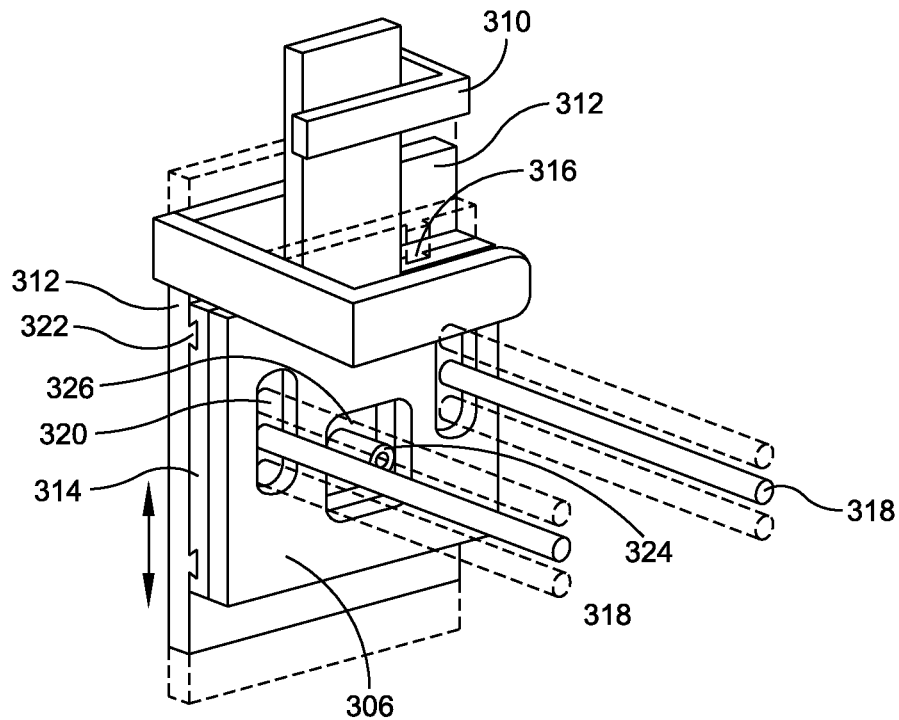
FIGS. 28A and 28B illustrate the relative movement permitted between each of the components of the alignment tool illustrated in FIG. 26.

Alignment rods 318 are disposed in the same horizontal plane and extend from mid-plate 314 through vertically elongated slots 320 defined by foot rest 306 such that rods 318 are disposed on opposite sides of the tibia in the medial-to-lateral plane when a foot is supported by foot holder assembly 302. Vertical movement of mid-plate 314 moves alignment rods 318 up-and-down in unison within slots 320 on opposite sides of the foot rest 306 (FIG. 28A).

Figure 28B:
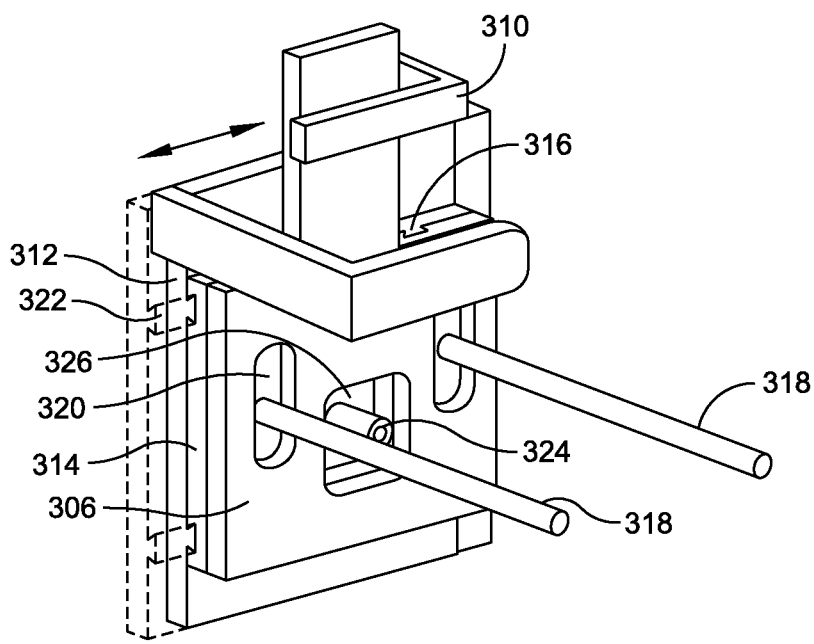

Back plate 312 is coupled to mid-plate 314 by sliding dovetail couplings 322 for side-to-side (i.e., horizontal) movement relative to foot rest 306 as illustrated in FIG. 28B. Back plate 312 also carries a bushing 324, which extends through openings 326 defined by mid-plate 314 and foot rest 306 and terminates at or near the plane of the foot rest 306 against which the bottom of the foot contacts. The center of the bushing 324 coincides with the intersection of the horizontal plane of the rods 318.

Figure 29:
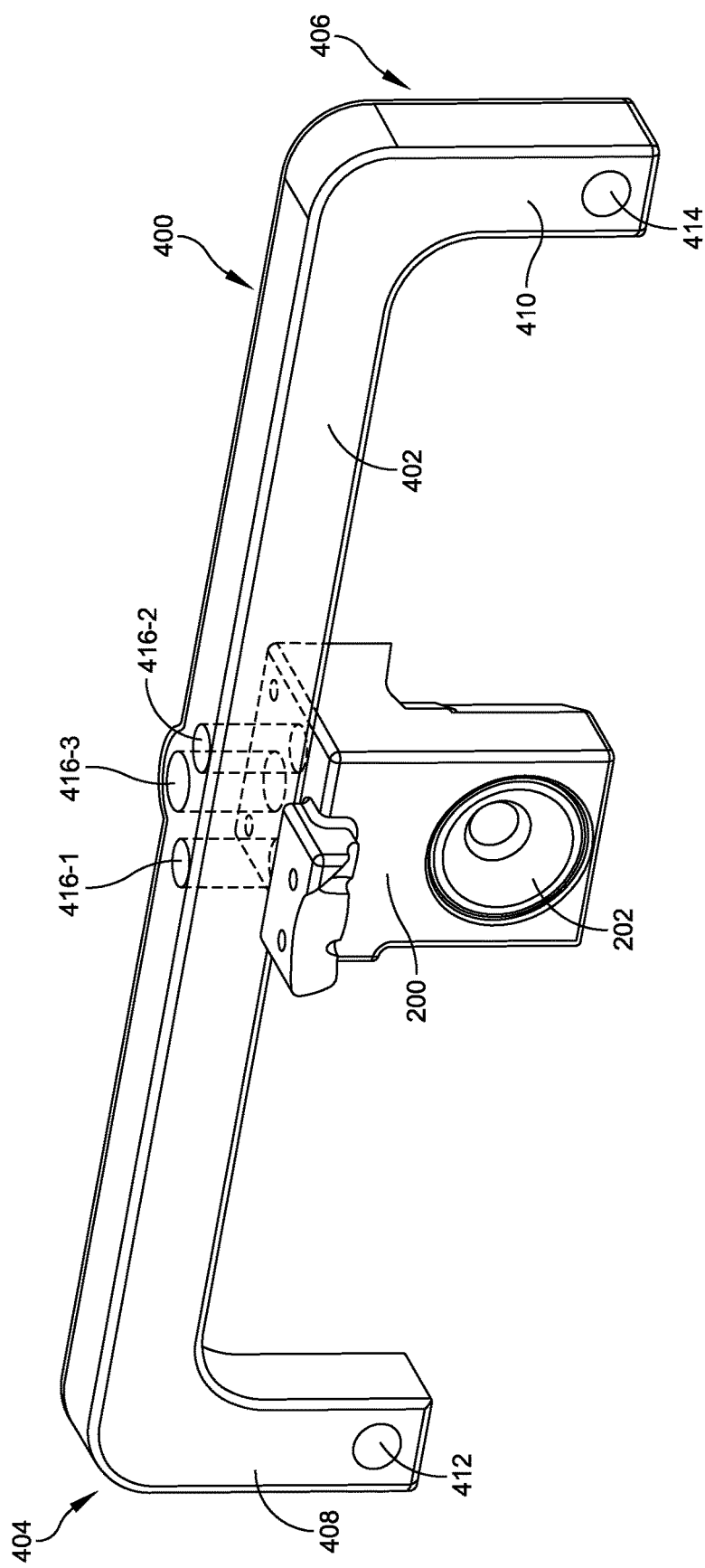
FIG. 29 is a perspective view of one example of an adapter bar for coupling the assemblage of the tibial drill guide mount and tibial drill guide to the alignment tool.

An adapter bar 400 for coupling tibial drill guide mount 200 to alignment tool 300 is illustrated in FIG. 29. Adapter bar 400 includes an elongate body 402 linearly extending from a first end 404 to a second end 406. Each of the ends 404, 406 includes a respective extension 408, 410 that extends from elongate body 402 at an angle. In some embodiments, extensions 408 and 410 orthogonally extend from elongate body 402, although one skilled in the art will understand that extensions 408 and 410 may diverge from elongate body 402 at other angles. In some embodiments, elongate body 402 may not have a linear shape, but may have a curved or arced shape as will be understood by one skilled in the art.

Each extension 408 and 410 defines a respective hole 412, 414 that is sized and configured to slidably receive alignment rods 318 that extend from alignment tool 300. Elongate body 402 defines one or more holes 416-1, 416-2, and 416-3 (collectively referred to as "holes 416") for coupling to adapter bar 400 to tibial drill guide mount 200. In some embodiments, the one or more holes 416 align with one or more holes 216 defined by body 204 of tibial drill guide mount 200 such that a pin or other device for maintaining the alignment and engagement of adapter bar 400 and tibial drill guide mount 200. For example, holes 216-1 and 216-2 of tibial drill guide mount 200 align with holes 416-1 and 416-2 of adapter bar 400, and hole 216-3 of drill guide mount 200 aligns with hole 416-3 of adapter bar 400. Dowel pins 70 (shown in FIG. 25C) may be inserted into holes 216-1 and 416-1 as well as into holes 216-2 and 416-2 to align tibial drill guide mount 200 with adapter bar 400 in both the horizontal and vertical directions (e.g., in the x- and y-directions), and a screw (not shown) may be inserted through hole 416-3 into threaded hole 216-3 to secure tibial drill guide mount 200 to adapter bar at the proper height or depth (e.g., in the z-direction).

Figure 30:
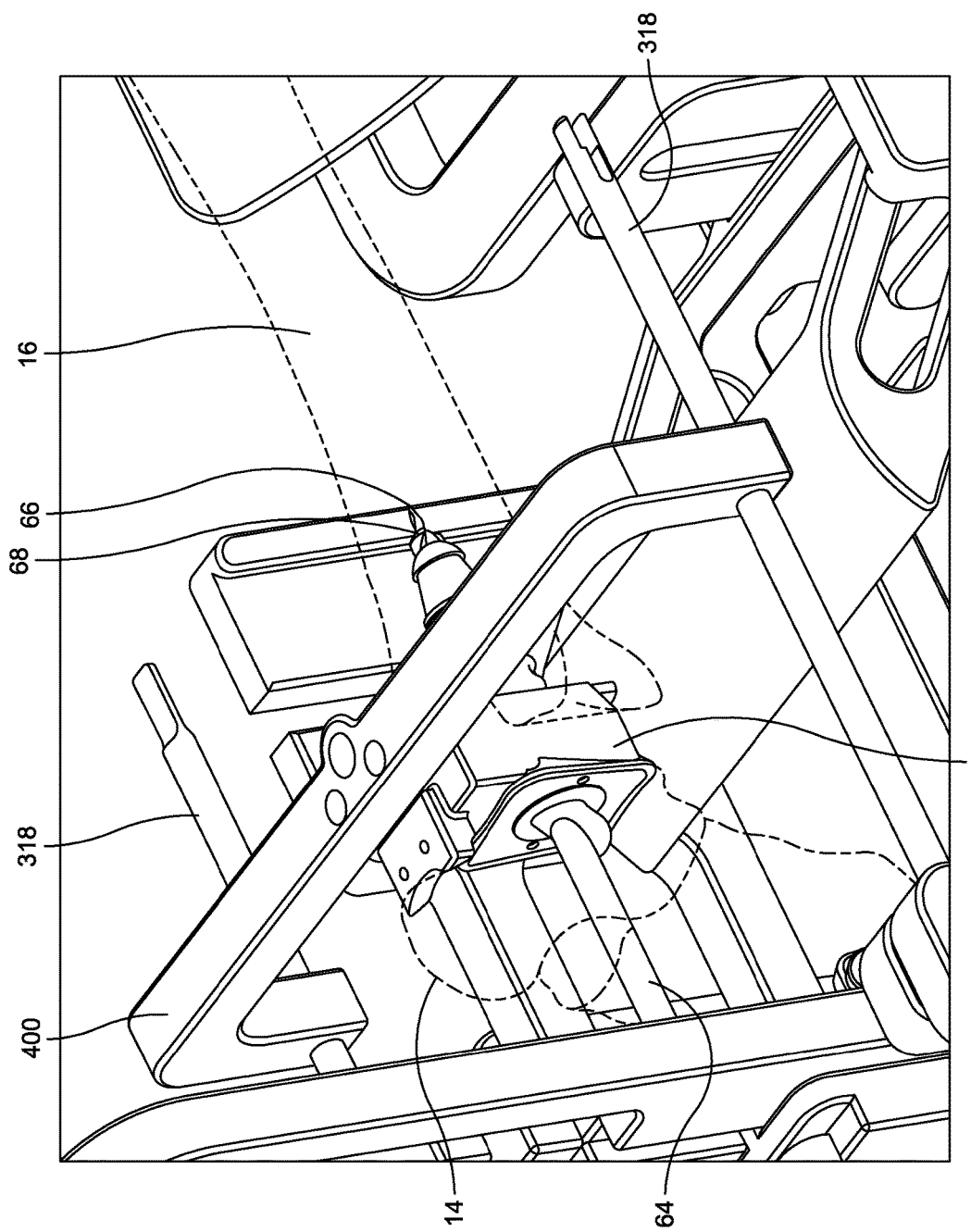
FIG. 30 is a perspective view of the adapter bar coupled to the assemblage of the tibial drill guide mount and tibial drill guide and to the alignment tool.

With tibial drill guide mount 200 and tibial drill guide 202 disposed within the resected ankle space 22, the foot and lower leg are placed in foot rest 306 and leg rest 304 (FIG. 30). The physician estimates the ankle's axis of dorsi-plantar rotation and visually aligns the ankle to the axis of rotation of the alignment tool 300. Foot rest 306 is adjusted to rotate the foot so that the big toe is essentially pointing in a vertical direction with respect to the leg that extends in a horizontal direction. The forefoot and heel are secured to foot rest 306 with clamps 308 and 310. Leg rest 304 is adjusted to the calf so that the tibia 16 is approximately parallel to the floor. The foot and calf are desirably aligned so that the anterior-posterior ("A-P") line of the talus's trochlea is essentially vertical.

Adapter bar 400 is coupled to alignment tool 300 by aligning holes 412 and 414 that are respectively defined by extensions 408 and 410 with alignment rods 318 of alignment tool 300. Adapter bar 400 is then slid along alignment rods 318 until holes 416 of adapter bar align with holes 216 defined by body 204 of tibial drill guide 200 (FIG. 30). As described above, dowel pins 70 are inserted into holes 416-1 and 416-2 of adapter bar 400 and holes 216-1 and 216-2 of tibial drill guide mount 200. With dowels 70 disposed within holes 216-1, 216-2, 416-1, and 416-2, tibial drill guide mount 200 is properly aligned with alignment tool 300 in the medial lateral (e.g., x-direction) and superior-inferior (e.g., y-direction) directions. A screw is inserted through hole 416-3 into threaded hole 216-3, which secures tibial drill guide mount 200 to adapter bar 400 and provides proper alignment in the anterior-posterior direction (e.g., the z-direction).

With the patient's foot disposed within alignment tool 300, bushing 324 on back plate 312 establishes alignment with the mechanical axis of tibia 16 and alignment of rods 318. Thus, after using adapter bar 400 to align tibial drill guide mount 200 with alignment tool 300 as described above, in line drilling of the center of the ankle and tibia for introduction of a bottom foot cannula is made possible without the use of fluoroscopy since aperture 246 of tibial drill guide 202 disposed within tibial drill guide mount 200 is aligned with an axis defined by bushing 324. Such arrangement enables an intramedullary channel to be formed that is substantially collinear with a mechanical axis defined by the tibia.

Various minimally invasive surgical techniques may be used to introduce a bottom foot cannula into the calcaneus 20, talus 14, and tibia 16. In one representative embodiment, bushing 324 is temporarily separated from the back plate 312 (e.g., by unscrewing) to provide access to the bottom of the foot. The physician uses a scalpel to make an initial incision in the bottom of the foot and replaces bushing 324. A cannulated trocar loaded with a k-wire (not shown) can be inserted through bushing 324, into the bottom of the foot, until the calcaneus 20 is contacted and the k-wire is firmly set within the calcaneus 20. The trocar can then be removed, and the k-wire lightly tapped further into the calcaneus 20. In a representative embodiment, the bushing 324 measures 6 mm in diameter, and the cannulated trocar can be 6 mm loaded with a 2.4 mm k-wire. The physician can now operate a cannulated first reamer (e.g., 6 mm) (not shown) over the k-wire up into the calcaneus 20 and talus 14. The first reamer opens an access path for insertion of a bottom foot cannula.

After withdrawing the first reamer and bushing 324, the physician then inserts a bottom foot cannula 64 as shown in FIG. 30. With the bottom foot cannula 64 in place, a second reamer 66 (e.g., 5 mm) can be operated through the cannula 64 to drill approximately another 100 mm through the talus 14 and up into the tibia 16 to establish an intramedullary guide path through the calcaneus 20 and talus 14 leading into the tibia 16 (FIG. 30). As second reamer 66 is advanced towards tibia 16, the tip 68 of reamer 66 is guided by the conical interior surface 248 of tibial drill guide 204, which is aligned with bushing 324 of alignment tool 300.

Once an intramedullary channel through the calcaneus 20, talus 14, and tibia 16 has been established, adapter bar 400 is decoupled from drill guide mount 200 and alignment rods 318. Drill guide mount 200 is removed from resected joint space 22 to expose the resected joint space to the surgeon.

With the resected ankle joint space 22 exposed to the surgeon, an ankle prosthesis is then installed. In one example, the ankle prosthesis includes a stem that may extend from the bottom of the calcaneus up to the top of the talus (i.e., a talo-calcaneal stem), although in some embodiment the stem is completely disposed within the talus (i.e., a talar stem). A convex dome is coupled to the stem and provides an articulating joint surface. A tibial stem may be monolithic or include a plurality of segments that may be coupled together in situ. A tibial platform couples to the tibial stem and either includes or is coupled to a convex joint surface for articulating with the articulating joint surface coupled to the talar/talo-calcaneal stem. Examples of such ankle prosthesis and methods of installing such prosthesis are disclosed in U.S. Pat. No. 7,534,246 issued to Reiley et al., the entirety of which is herein incorporated by reference.

Figure 31:
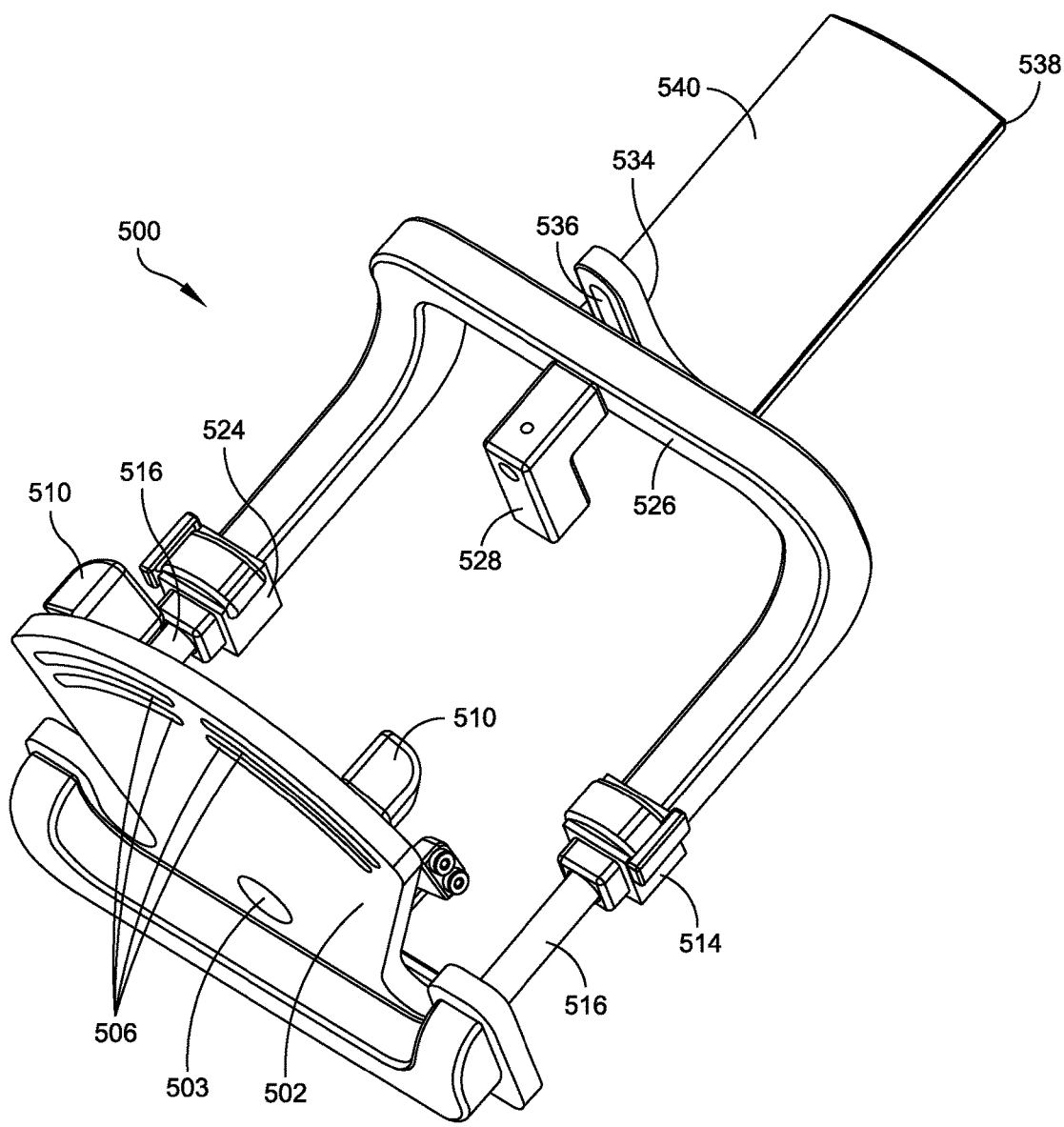
FIG. 31 is a top isometric view of another example of an alignment tool/foot holder assembly for use with a tibial drill guide mount and tibial drill guide.
Figure 32:
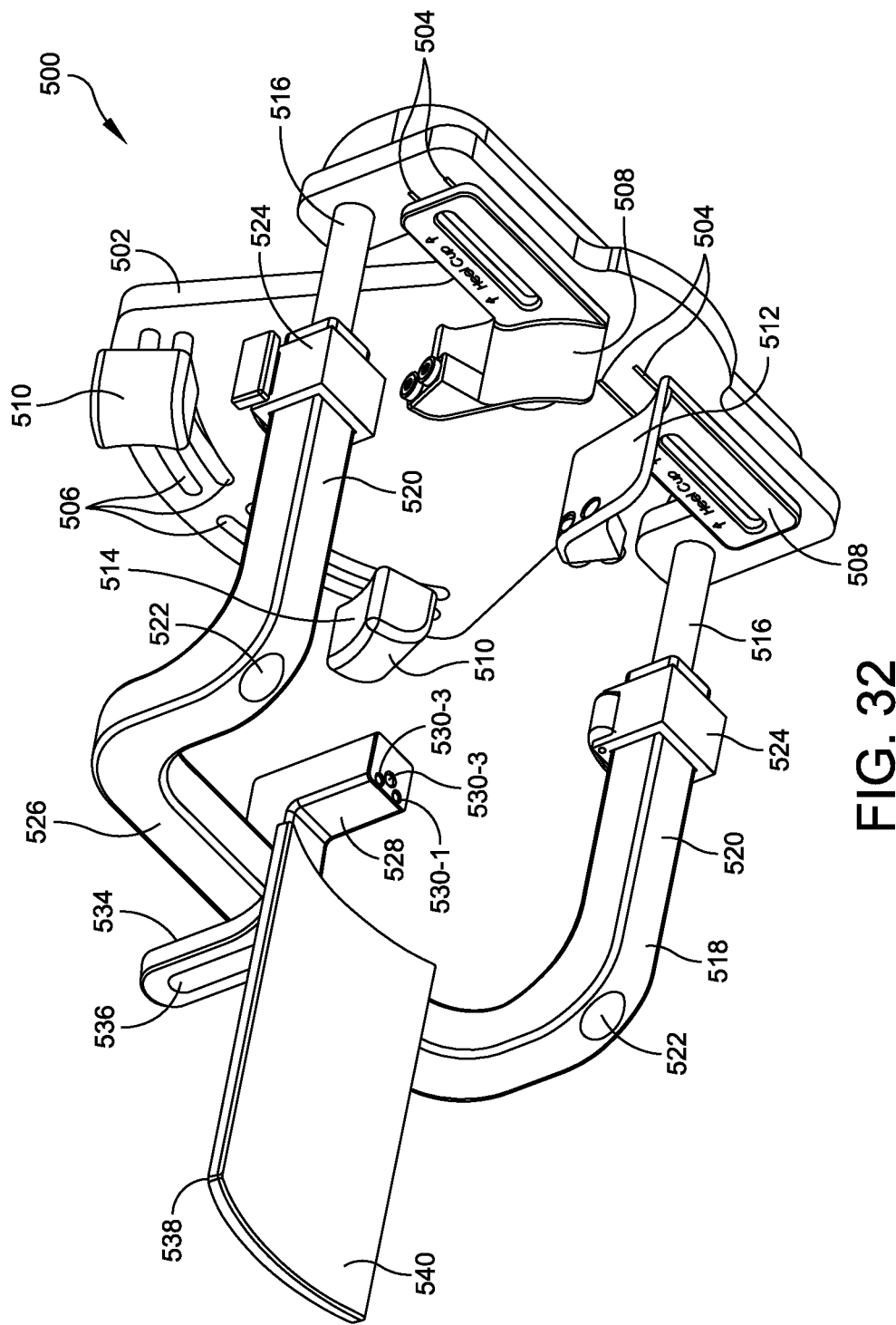
FIG. 32 is a bottom isometric view of the alignment tool/foot holder assembly illustrated in FIG. 31.
Figure 33:
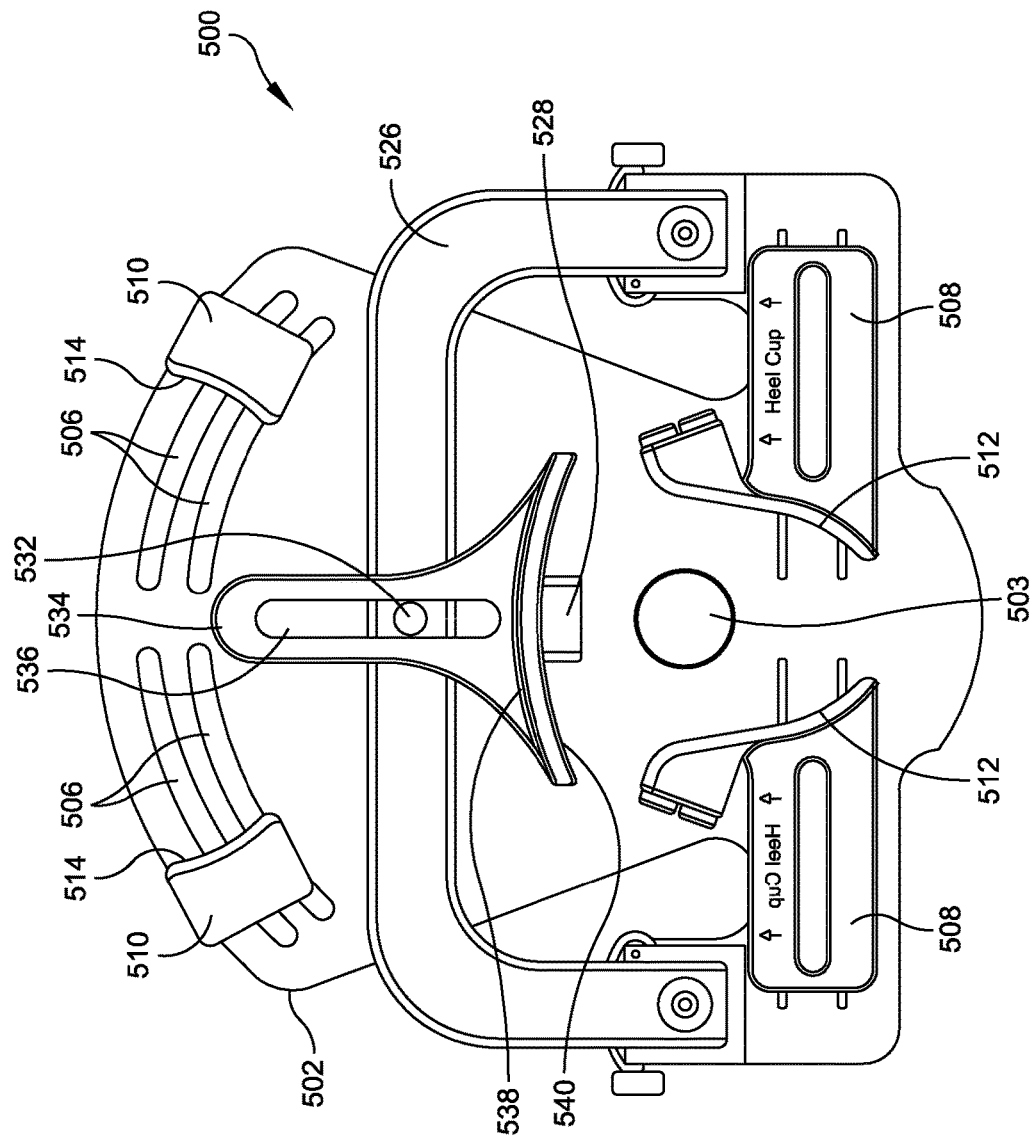
FIG. 33 is an elevational front view of the alignment tool/foot holder assembly illustrated in FIG. 31.

The disclosed tibial drill guide mount 200 and drill guide 202 may be used with a variety of alternative alignment tools. For example, FIGS. 31-34 illustrate another example of an alignment tool in the form of a foot holder assembly 500 to which tibial drill guide mount 200 may be directly coupled. As shown in FIGS. 31 and 32, foot holder assembly 500 includes a base plate 502 defining a plurality of slots 504 and 506 and an aperture 503.

Slots 504 are sized and configured to slidably receive a pair of heel clamps 508, and slots 506 are sized and configured to slidably receive a pair of forefoot clamps or guides 510. Heel clamps 508 and forefoot clamps 510 cooperate to maintain a foot of a patient in a desired position with respect to base plate 502 by utilizing a locking mechanism such as, for example, a set screw or other locking device, to fix the position of heel clamps 508 and forefoot clamps 510 to base plate 502. The respective foot engaging surfaces 512 and 514 of heel clamps 508 and forefoot clamps 510 may have a shape that complements the medial and lateral shape of a human foot.

Figure 34:
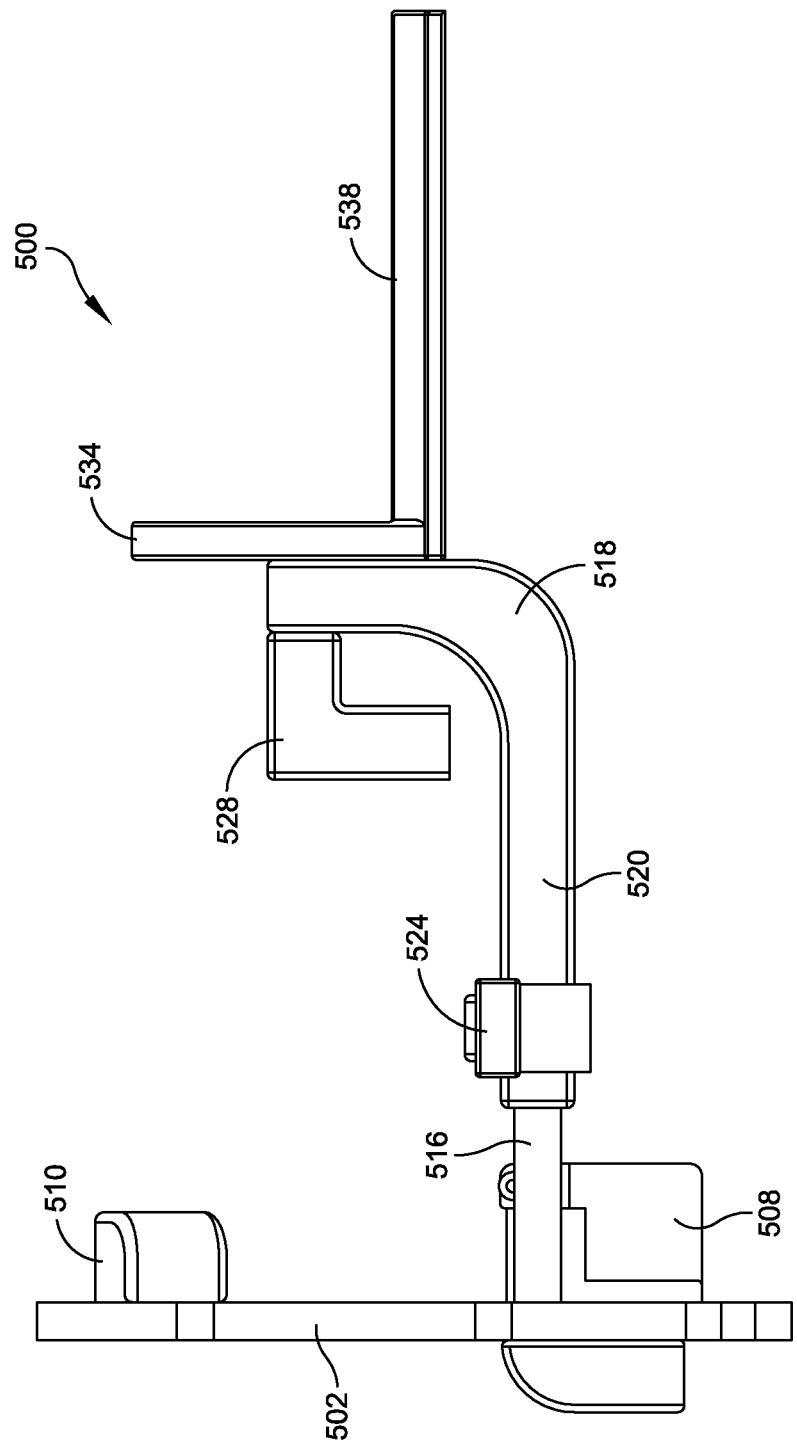
FIG. 34 is an elevational side view of the alignment tool/foot holder assembly illustrated in FIG. 31.

Extending from base plate 502 are a pair of alignment rods 516 that are arranged on base plate 502 such that one alignment rod is disposed on a medial side of a patient's foot and the other alignment rod is disposed on a lateral side of a patient's foot. A coupling bar 518 is sized and configured to slidably engage alignment rods 516 as best seen in FIGS. 32 and 34. Coupling bar 518 includes a pair of spaced apart legs 520 that define channels 522 (FIG. 32) in which alignment rods 516 are slidably received. One or both of legs 520 include a clamp or other locking mechanism 524 for increasing the friction between coupling bar 518 and alignment rods 516 in order to releasably lock coupling bar 518 at a certain position along the length of alignment rods 516.

Medial-lateral cross bar 526 couples together legs 520 of coupling bar 518. Extending from medial-lateral cross bar 526 is mount coupling member 528. Mount coupling member 528 includes one or more holes 530-1, 530-2, and 530-3 (collectively referred to as "holes 530") that are sized and configured to align with holes 216 defined by tibial drill guide mount 200.

A peg 532 (FIG. 33) extends from medial-lateral cross bar 526 for coupling shin engaging member 534 via slot 536 defined by shin engaging member 534. Shin engaging member 534 includes a shelf 538 having a concave surface 540 for abutting a shin of a patient. A nut or other locking mechanism (not shown) for engaging peg 532, which may be threaded, may be used to fix the position of shelf 538 relative to medial-lateral cross bar 526.

The use of foot holder assembly 500 in connection with the assemblage of tibial drill guide mount 200 and tibial drill guide 202 is similar to the use of alignment tool 300 described above. For example, once the assembly of tibial drill guide mount 200 and tibial drill guide 202 are disposed within resected joint space 22, the heel of the patient's foot is placed between heel clamps 508 and the patient's forefoot is placed between forefoot clamps 510. The locking mechanisms of heel and forefoot clamps 508 and 510 may be engaged to initially set positions of heel and forefoot clamps 508 and 510 relative to base plate 502.

Holes 530 of coupling member 528 are aligned with holes 216 defined by tibial drill guide mount 200 by sliding legs 520 of coupling bar 518 along alignment rods 516. Dowel pins 70 and/or a threaded screw (not shown) may be used to couple holes 530 of coupling member 528 to holes 216 of tibial drill guide mount 200. The surgeon may check to ensure that the patient's foot is firmly against base plate 502 and then engage clamps 524 such that coupling bar 518 is fixed to alignment rods 516.

Shin engaging member 534 is adjusted until concave surface 540 contacts the patient's shin. The adjustment of shin engaging member 534 is guided by the engagement between slot 536 and peg 532. With shin engaging member 534 in the desired position, the nut or other locking mechanism (not shown) locks shin engagement member 534 in place. The surgeon may make final adjustments to the heel and forefoot clamps 508 and 510 and then create the intramedullary channel as described above.

Figure 35:
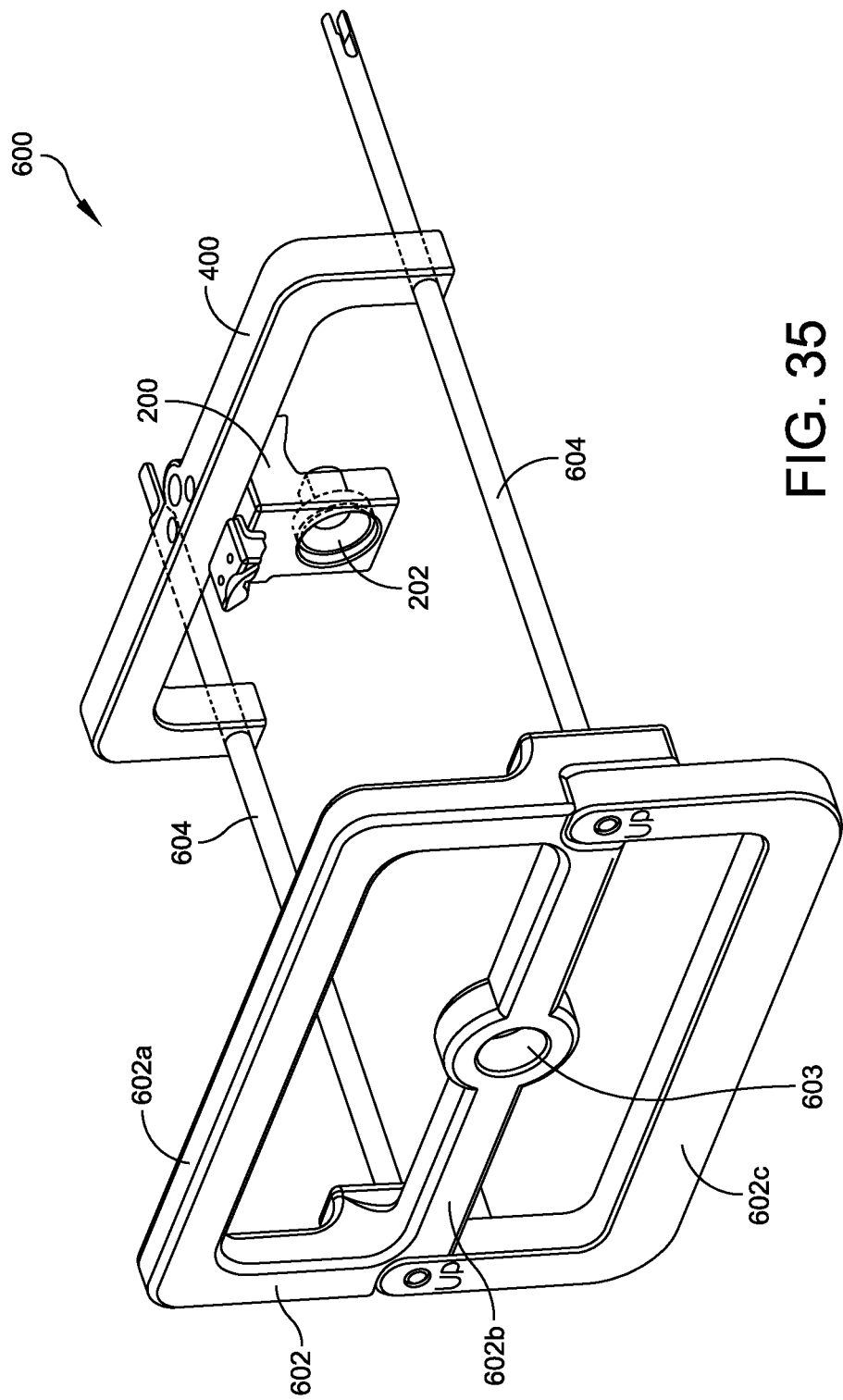
FIG. 35 is a top isometric view of another example of an alignment tool/foot holder assembly for use with the tibial drill guide mount and tibial drill guide.
Figure 36:
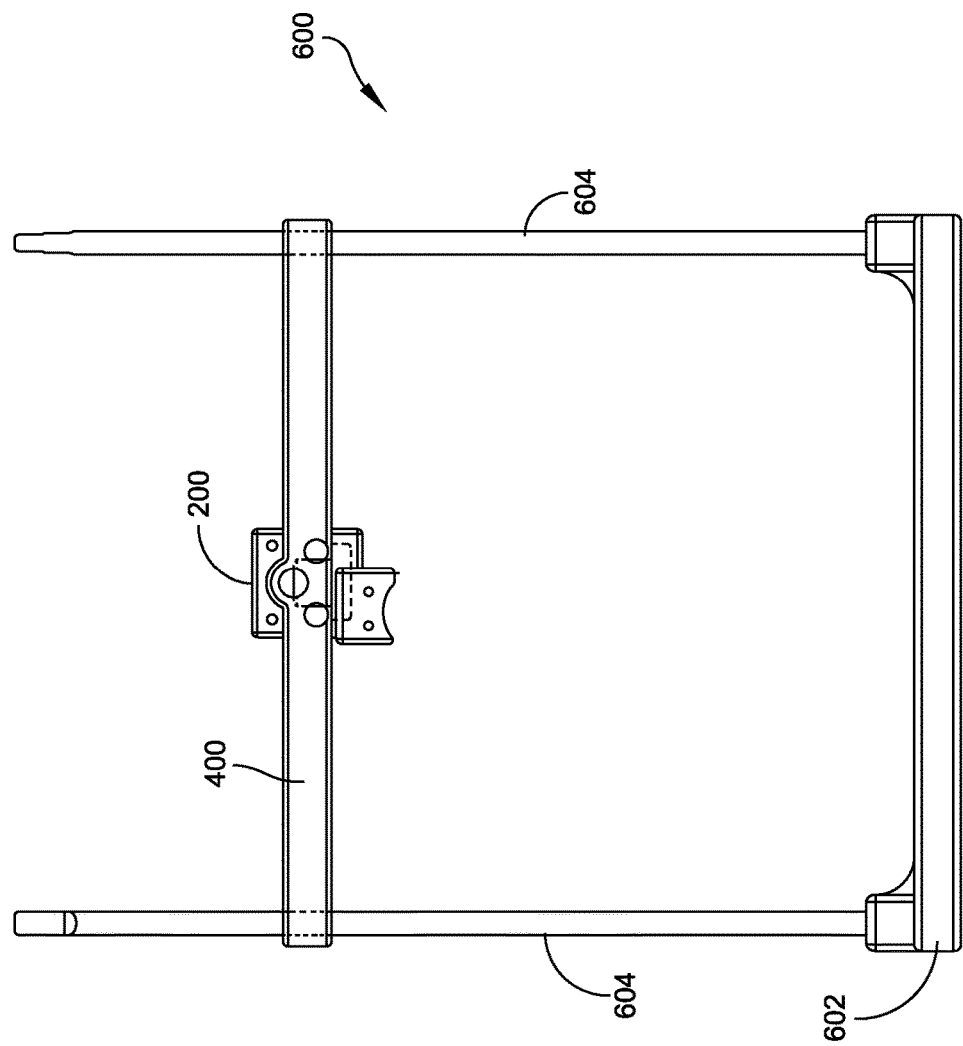
FIG. 36 is a top elevational view of the alignment tool/foot holder assembly illustrated in FIG. 35.
Figure 37:
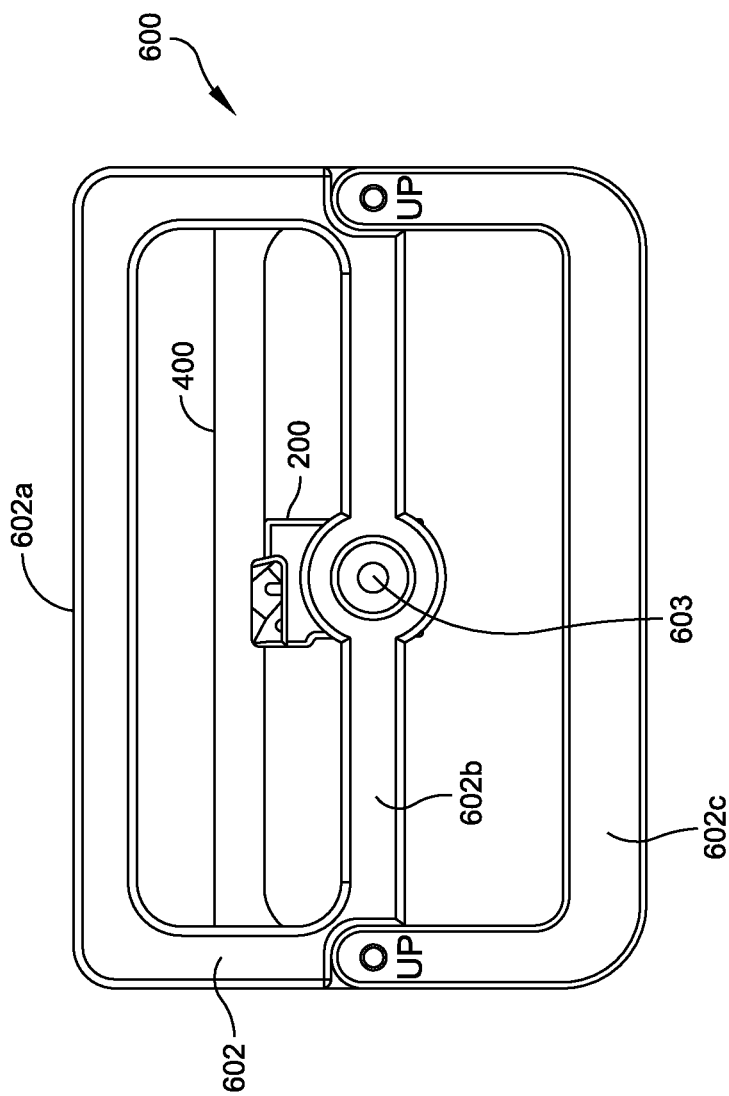
FIG. 37 is an elevational front view of the alignment tool/foot holder assembly illustrated in FIG. 35.
Figure 38:
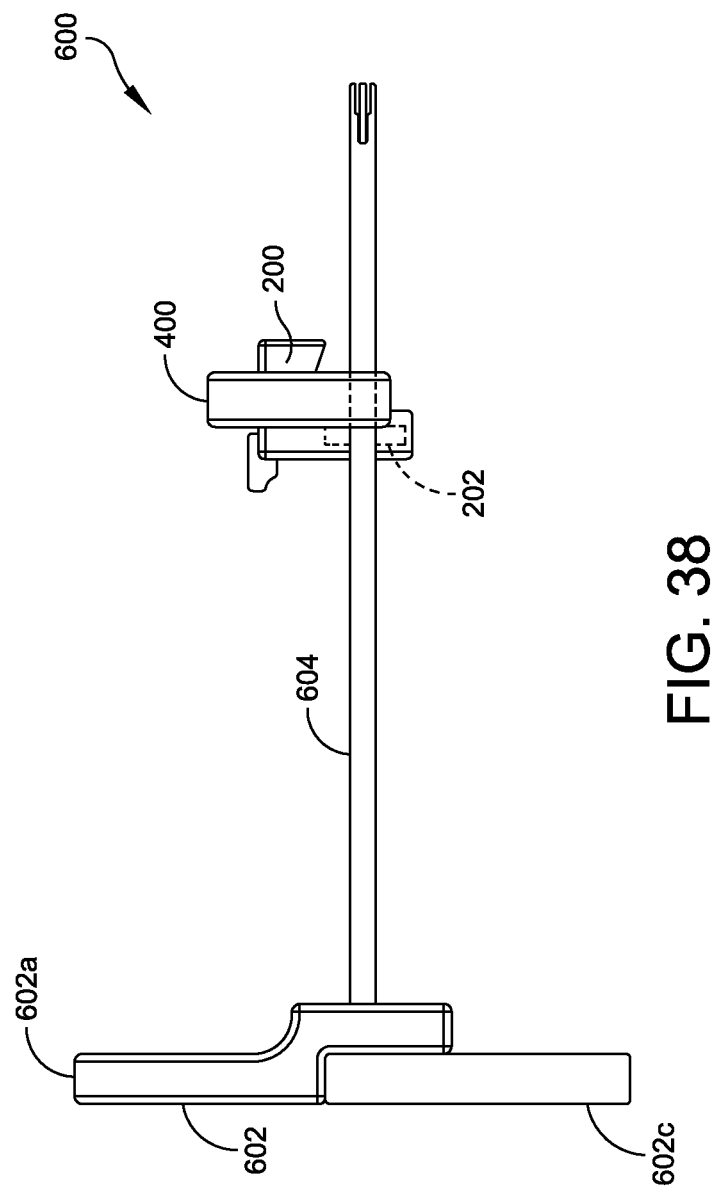
FIG. 38 is an elevational side view of the alignment tool/foot holder assembly illustrated in FIG. 35.
Figure 39:
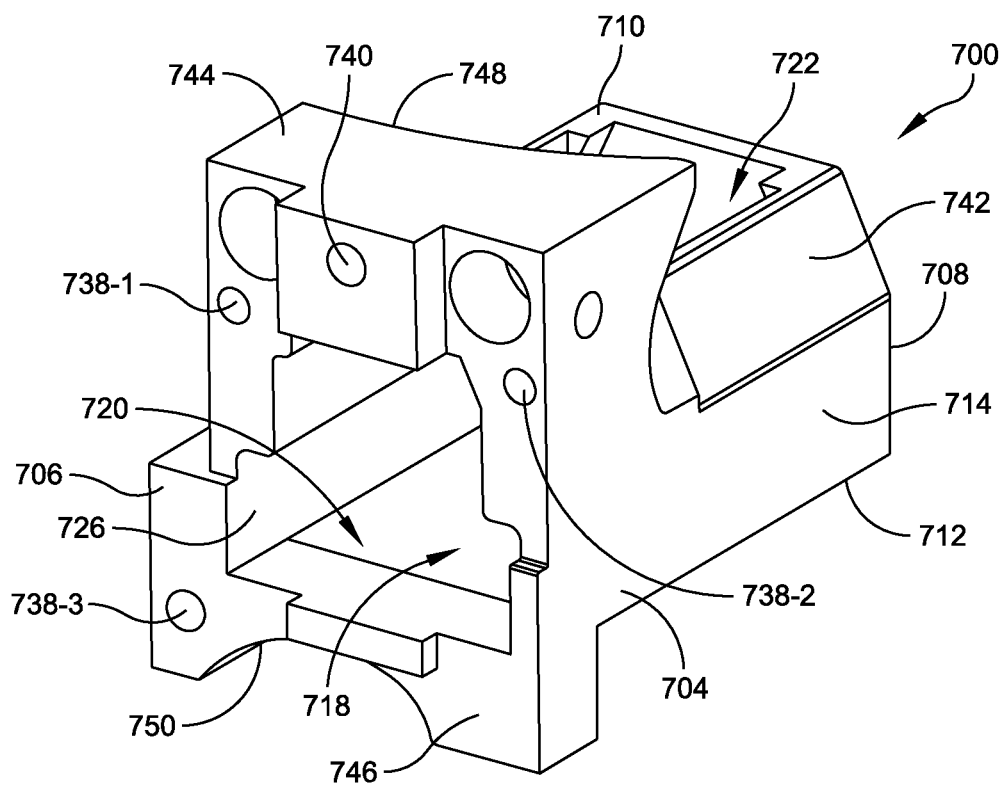
FIG. 39 is a perspective view of another example of a tibial cutting guide mount.
Figure 40:
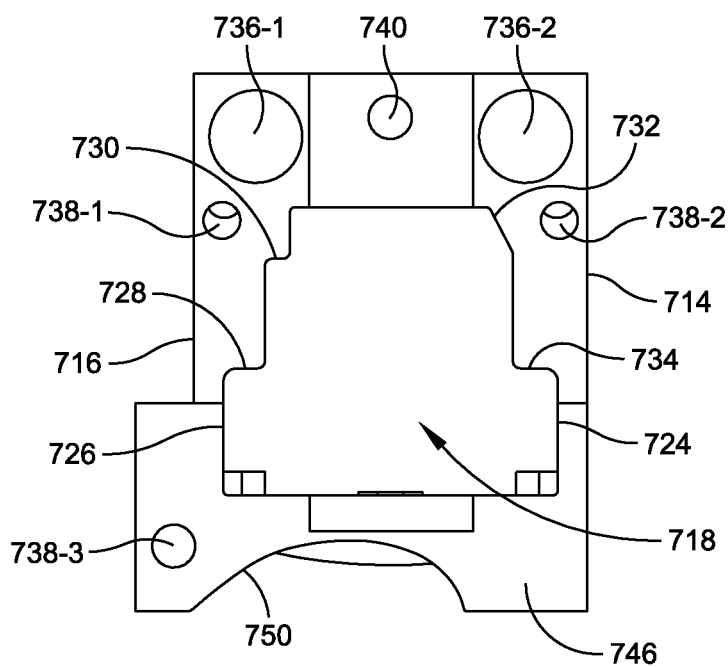
FIG. 40 is a front side elevational view of the tibial cutting guide mount illustrated in FIG. 39.
Figure 41:
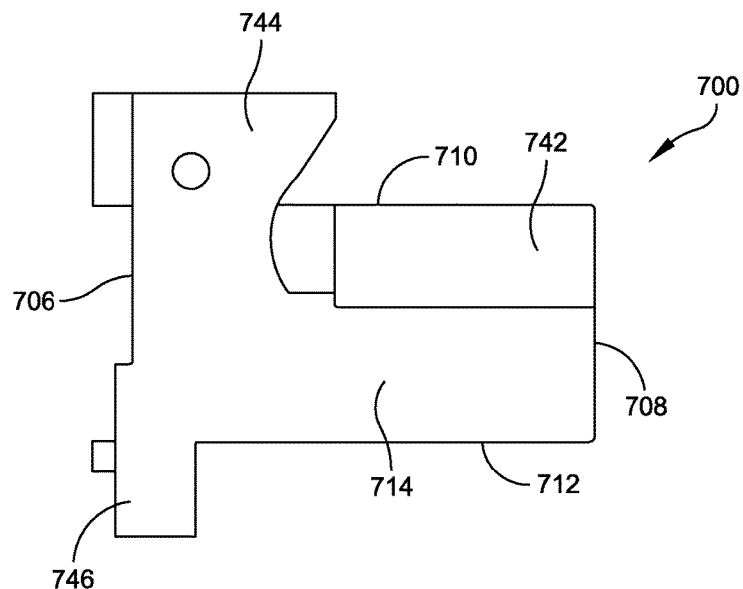
FIG. 41 is a side elevational view of the tibial cutting guide mount illustrated in FIG. 39.
Figures 42, 43:
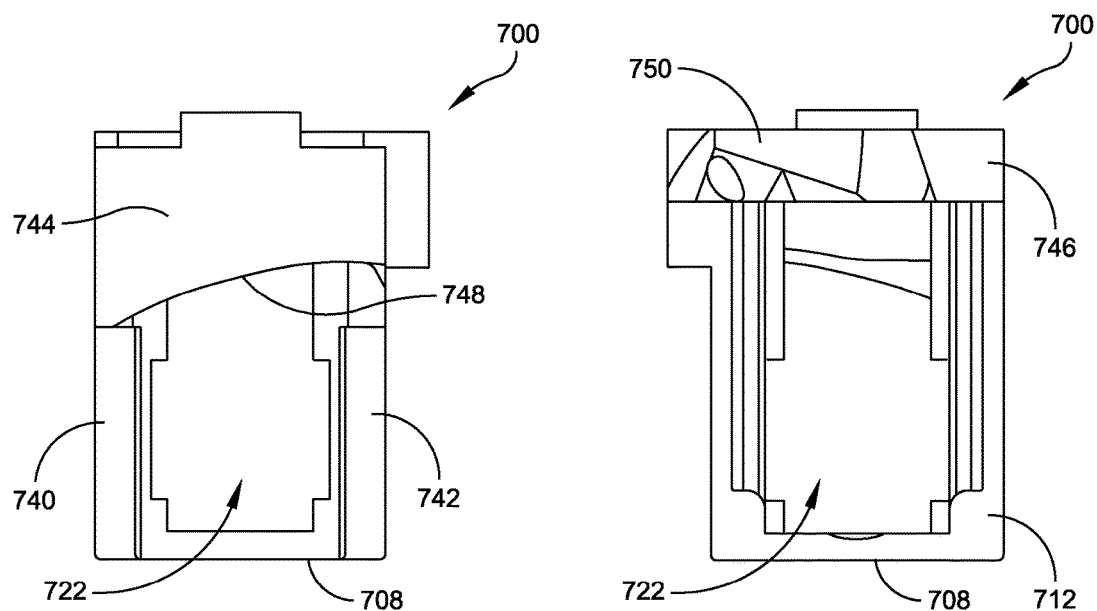
FIG. 42 is a top side view of the tibial cutting guide mount illustrated in FIG. 39.
FIG. 43 is a bottom side view of the tibial cutting guide mount illustrated in FIG. 39.

Another example of an alignment tool 600 for use with tibial drill guide mount 200 and tibial drill guide 202 is illustrated in FIGS. 35-38. As shown in FIG. 35, alignment tool 600 includes a base plate 602 comprising a plurality of bars 602a, 602b, and 602c. Although three bars 602a, 602b, and 602c are illustrated, one skilled in the art will understand that fewer or more bars may be implemented. Bar 602b defines a hole 603 sized and configured to receive a surgical tool, such as, for example, a cannulated drill. Additional elements including, but not limited to, heel clamps and/or forefoot clamps (not shown) may be coupled to the bars 602a, 602b, and 602c of base plate 602 for aiding in the positioning of a patient's foot with respect to hole 603.

Extending from base plate 602 is a pair of spaced apart alignment rods 604. One of alignment rods 604 may be disposed on a medial side of a patient's leg, and the other alignment rod 604 disposed on a lateral side of the patient's leg. Alignment rods 604, like alignment rods 318 of alignment tool 300, may be slidably receiving within holes 412, 414 of adapter bar 400.

The use of alignment tool 600 in connection with the assemblage of tibial drill guide mount 200 and tibial drill guide 202 and the adapter bar 400 is similar to the use of alignment tool 300 described above. For example, once the assembly of tibial drill guide mount 200 and tibial drill guide 202 are disposed within resected joint space 22, adapter bar 400 is coupled to alignment tool 600 by aligning holes 412 and 414 that are respectively defined by extensions 408 and 410 with alignment rods 604 of alignment tool 600. Adapter bar 400 is slid along alignment rods 604 until holes 416 of adapter bar align with holes 216 defined by body 204 of tibial drill guide 200. As described above, dowel pins are inserted into holes 416-1 and 416-2 of adapter bar 400 and 216-1 and 216-2 of tibial drill guide mount 200. With dowels disposed within holes 216-1, 216-2, 416-1, and 416-2, tibial drill guide mount 200 is properly aligned with alignment tool 600 in the medial lateral (e.g., x-direction) and superior-inferior (e.g., y-direction) directions. A screw is inserted through hole 416-3 into threaded hole 216-3, which secures tibial drill guide mount 200 to adapter bar 400 and provides proper alignment in the anterior-posterior direction (e.g., the z-direction). The surgeon may make final adjustments to the heel and forefoot clamps 508 and 510 and then create the intramedullary channel as described above.

FIGS. 39-63 illustrate another embodiment of a system for performing a surgical procedure. Specifically, FIGS. 39-43 illustrate a tibial drill guide mount 700 sized and configured to receive the tibial drill guide cartridge 702 illustrated in FIGS. 44-47. Tibial drill guide mount 700 may also receive other drill guide cartridges for use during other stages of the surgical procedures. Like tibial drill guide mount 200, tibial drill guide 700 may be fabricated from a resilient polymer material of the type that is suitable for use in connection with stereo lithography, selective laser sintering, or the like manufacturing equipment, e.g., a polyamide powder repaid prototype material is suitable for use in connection with selective laser sintering.

As shown in FIG. 39-43, tibial drill guide mount 700 has a somewhat rectangular body 704 having a front side 706, a rear side 708, top side 710, bottom side 712, and a pair of opposed sides 714 and 716. Front side 706 defines a recess 718 sized and configured to slidably receive tibial drill guide 702 therein. Recess 718 communicates with a recess 720 (FIGS. 39 and 43) defined by bottom side 712 and a recess 722 (FIGS. 39, 42, and 43) defined by top side 710 such that body 704 is substantially hollow.

The respective inner surfaces 724, 726 of sides 714, 716 have different geometries that correspond with the cross-sectional geometry of tibial drill guide cartridge 702 to ensure that tibial drill guide cartridge 702 is properly inserted into recess 718. In the embodiment illustrated in FIGS. 39-43, side 716 includes first and second ledges 728, 730 that inwardly extend into recess 718, and side 714 has an inwardly tapered upper region 732 and an inwardly extending ledge 734. One skilled in the art will understand that sides 714, 716 may include other features for ensuring proper insertion of tibial drill cartridge 702 into recess 718. In some embodiments, sides 714, 716 may have the identical geometry and tibial drill guide cartridge may be reversibly inserted into recess 718.

Front side 706 defines one or more dowel holes 736-1, 736-2 (collectively referred to as "dowel holes 736") sized and configured to receive a dowel pin 70 therein. One or more through holes 738-1, 738-2, 738-3 (collectively referred to as "through holes 738") extend through front side 706, which also defines a blind hole 740. Through holes 738 are sized and configured to receive k-wires for pinning tibial drill guide mount to a patient's bone as described below.

Top side 710 of tibial drill guide mount 700 includes a pair of chamfers 742 that are sized and configured to be mate against and reference the resected surfaces of the lower tibia 16a (FIG. 8). Tibial drill guide mount 700 also includes a tibial engagement structure 744 and a talar engagement structure 746. Tibial engagement structure 744 extends from top side 710 and includes a substantially conformal engagement surface 748. Talar engagement structure 746 extends from bottom side 712 and also includes a substantially conformal engagement surface 750.

Figure 44:
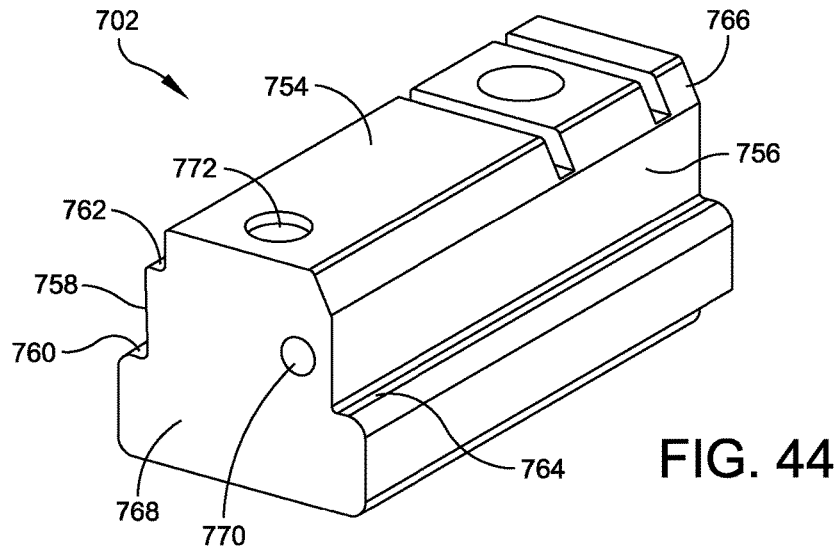
FIG. 44 is a perspective view of a tibial drill guide cartridge for use with the tibial drill guide mount illustrated in FIG. 39.
Figure 45:
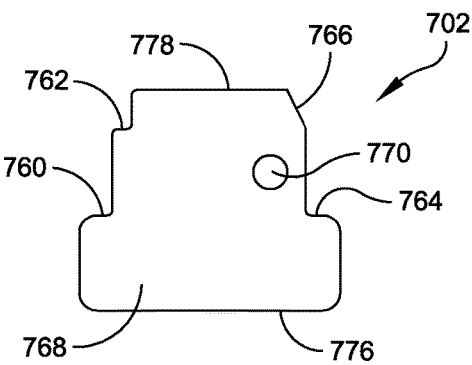
FIG. 45 is a front end view of the tibial drill guide cartridge illustrated in FIG. 44.
Figure 46:
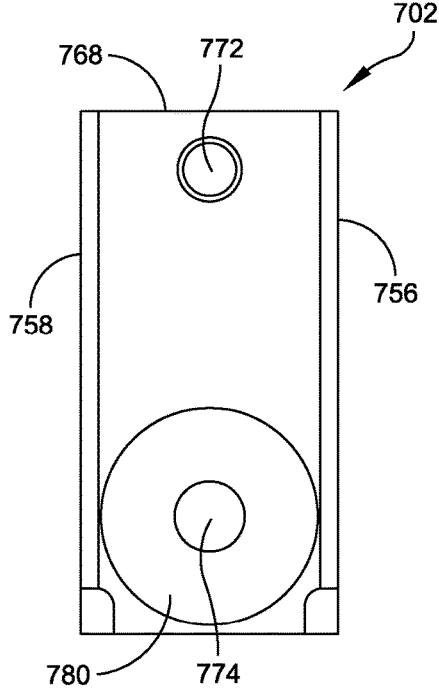
FIG. 46 is a bottom side plan view of the tibial drill guide cartridge illustrated in FIG. 44.

Tibial drill guide cartridge 702 has a substantially rectangular elongate body 754 that may be formed from a more substantial material than tibial drill guide mount 700 such as, for example, metals, ceramics, or the like. As best seen in FIGS. 44 and 45, the geometry of sides 756, 758 is respectively complementary to the sides 714, 716 of tibial drill guide mount 700. For example, side 758 includes ledges 760 and 762 that respectively correspond to ledges 728 and 730, and side 756 includes a ledge 764 and an angled section 766, which respectively correspond to ledge 734 and upper region 732 of tibial drill guide mount 700.

Figure 47:
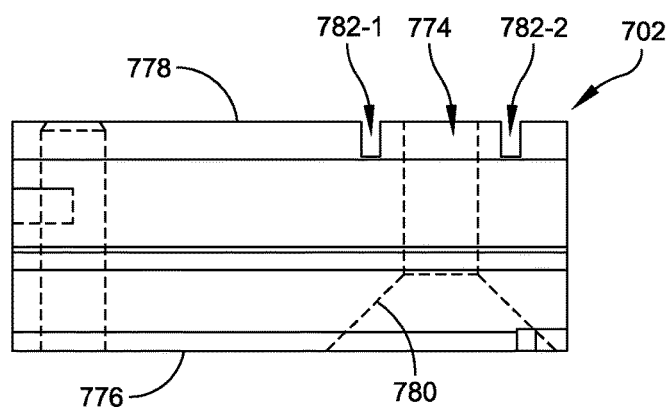
FIG. 47 is a side view of the tibial drill guide cartridge illustrated in FIG. 44.

Front side 768 of tibial drill guide cartridge 702 defines a blind hole 770, which may be threaded for reasons described below. Tibial drill guide cartridge 702 defines a pair of holes 772 and 774 that extend from bottom surface 776 to top surface 778. Hole 772 may be a reamed hole that is sized and configured to receive a ball detent therein, and hole 774 has an internal surface 780 that tapers from a larger diameter at bottom surface 776 to a smaller surface that is sized and configured to receive a surgical tool, such as a drill and/or reamer. Top surface 778 defines a pair of parallel slots 782-1, 782-2 (collectively referred to as "slots 782") that extend from side 756 to side 758. As best seen in FIGS. 44 and 47, slots 782 are disposed equidistant from a central axis defined by hole 774 to provide a visual key for a physician that wants check the alignment of hole 774 with a mechanical axis of a patient's tibia using fluoroscopy.

Figure 48:
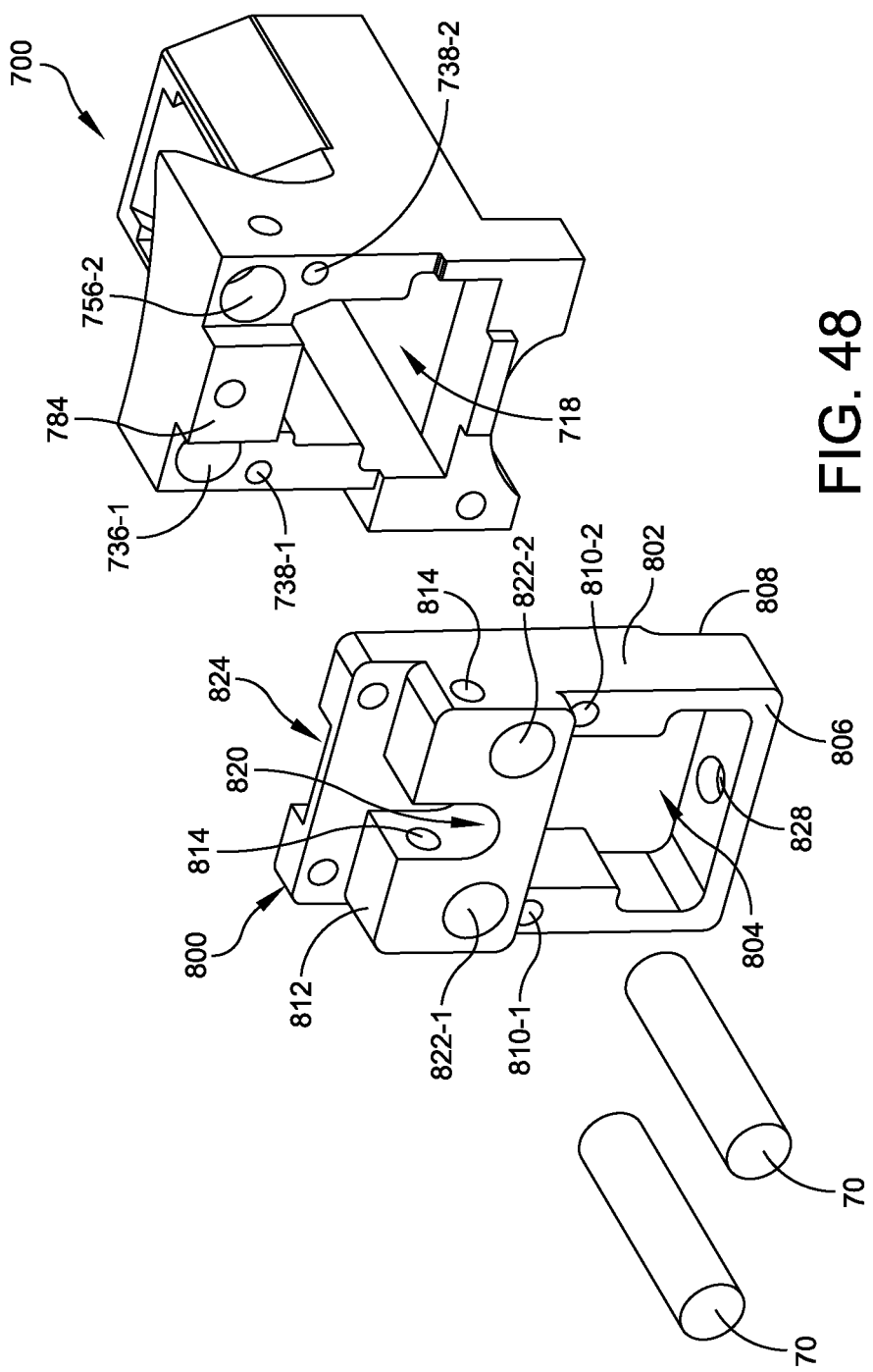
FIG. 48 is an exploded perspective view of a mounting plate and dowel pins configured to for use with the tibial drill guide mount illustrated in FIG. 39.

As illustrated in FIG. 48, a mounting plate 800 has a substantially rectangular body 802 that is fabricated from a material including, but not limited to, metals, ceramics, or the like. Body 802 defines an aperture 804 the extends from front side 806 to back side 808 and has a similar geometry of recess 718 of tibial drill guide mount 700 such that tibial drill guide cartridge 702 may be received therein. Body 802 also defines a pair of through holes 810-1, 810-2 (collectively referred to as "holes 810") that are arranged on body 802 such that they correspond to holes 738 of tibial drill guide mount 700 and are sized and configured to receive a k-wire or pin therein.

A mounting base 812 extends from front side 806 of mounting plate 800 and defines a hole 814 that extends from a first side 816 to a second side 818. Mounting base 812 defines a notch 820 and one or more dowel pin holes 822-1, 822-2 (collectively referred to as "holes 822") that are aligned with holes 736 of tibial drill guide mount 700. Notch 820 bisects hole 814. Mounting base 812 may also define one or more recesses 824 that correspond to one or more protrusions 784 that extends from front side 706 of tibial drill guide mount 700. Recesses 824 and protrusions 784 cooperate to ensure that mounting base 812 and tibial drill guide mount 700 are properly aligned. One skilled in the art will understand that other geometric features may be implemented to ensure proper alignment between mounting base 812 and tibial drill guide mount 700.

Figure 49:
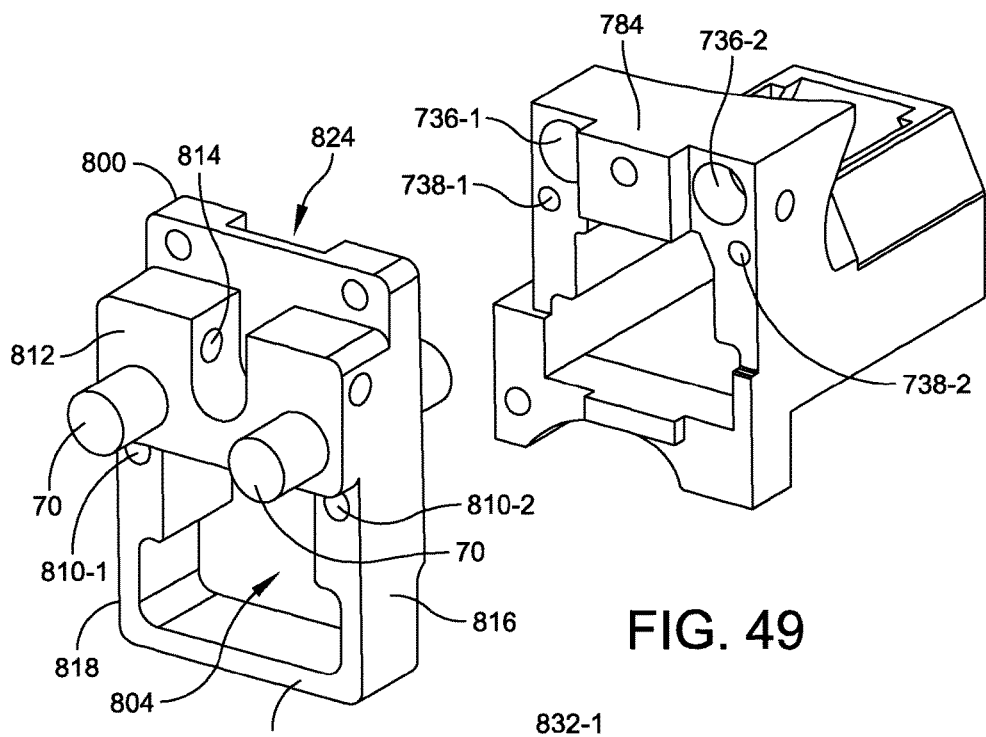
FIG. 49 is a partially exploded perspective view of a mounting plate and dowel pins configured to for use with the tibial drill guide mount illustrated in FIG. 39.
Figure 50:
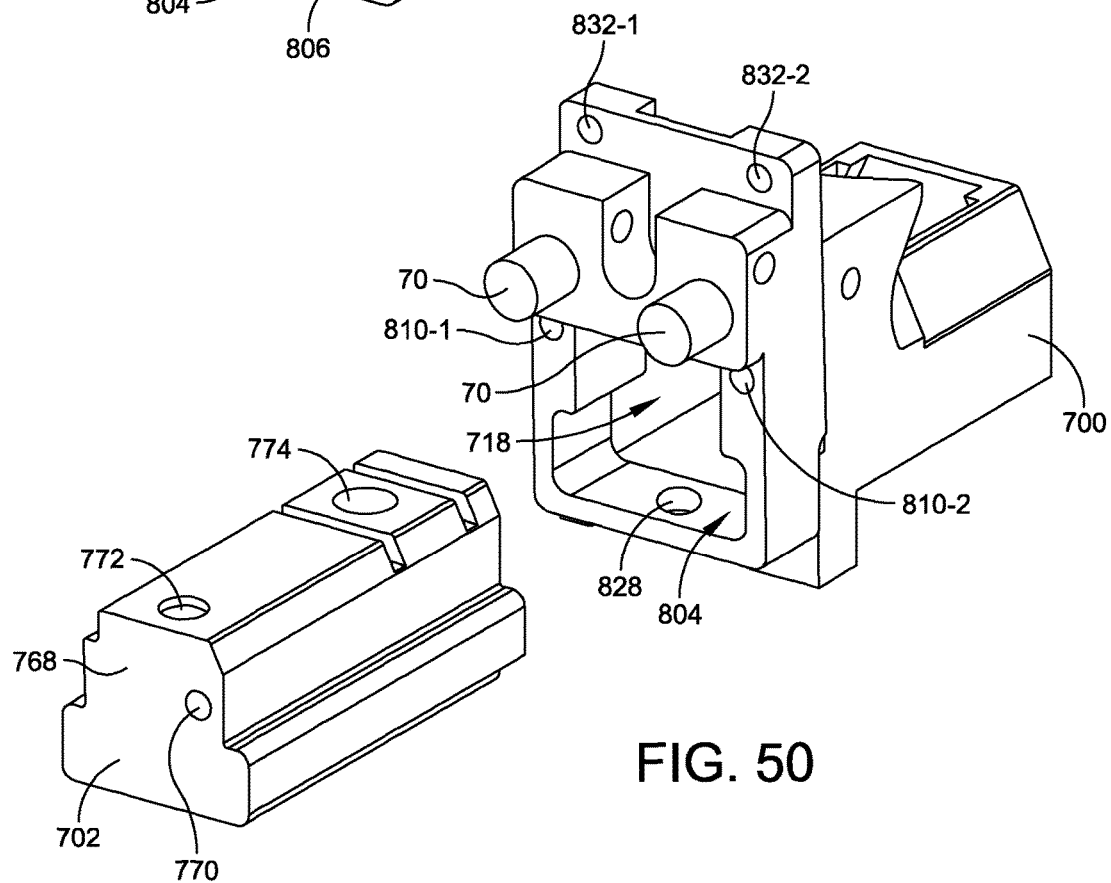
FIG. 50 is a partially exploded perspective view of a mounting plate, dowel pins, and tibial drill guide mount configured to receive a tibial drill guide cartridge in accordance with FIG. 44.
Figure 51:
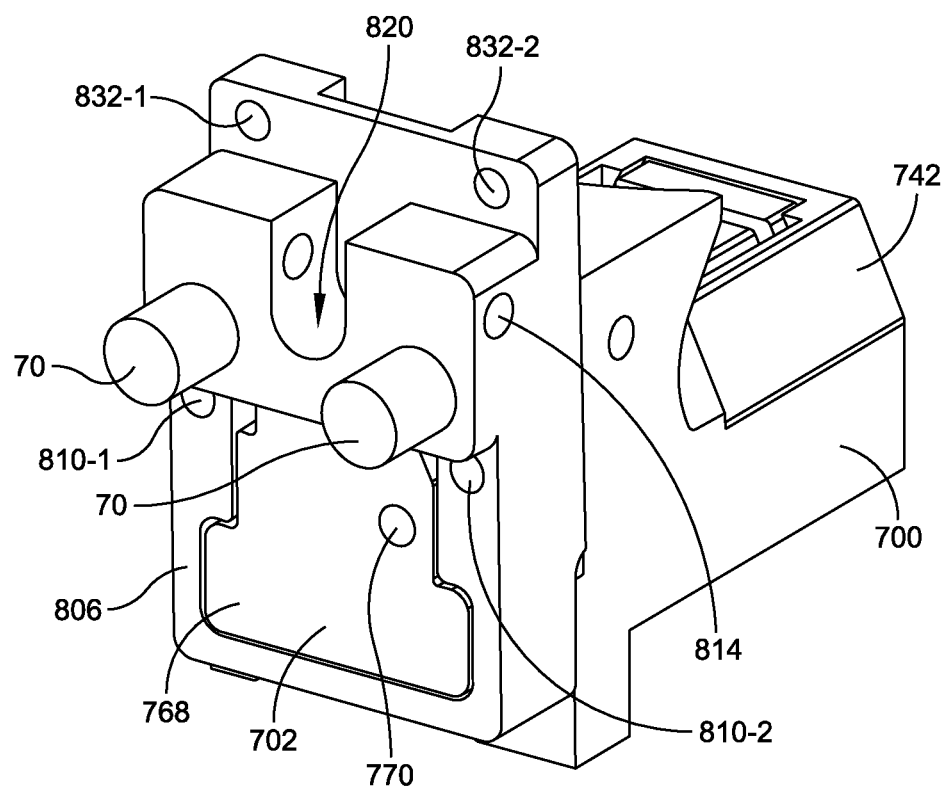
FIG. 51 is a perspective view of the tibial drill guide mount, tibial drill guide cartridge, dowel pins, and mounting plate assembled together.
Figure 52:
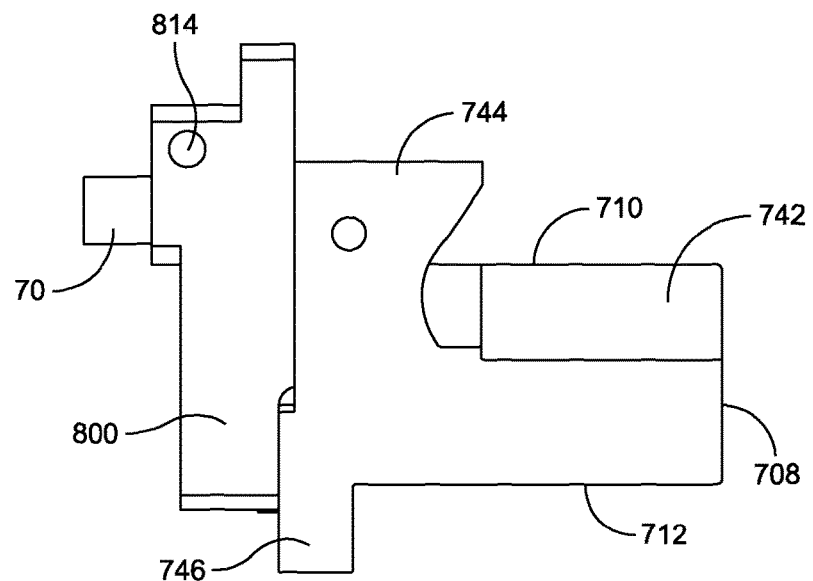
FIG. 52 is a side view of the assembly illustrated in FIG. 51.
Figure 53:
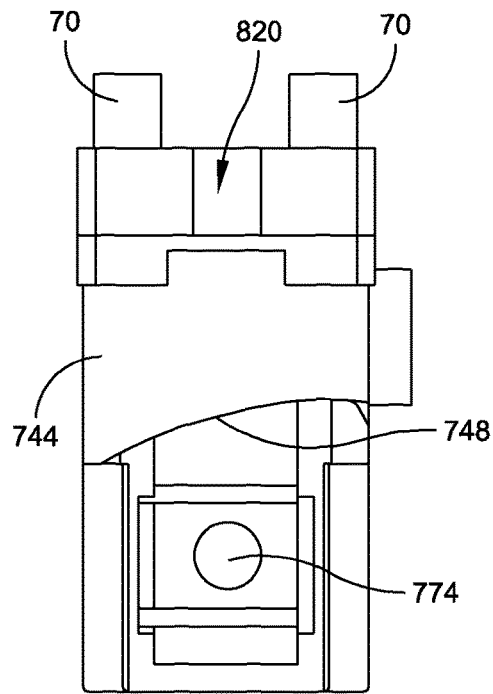
FIG. 53 is a top side plan view of the assembly illustrated in FIG. 51.
Figure 54:
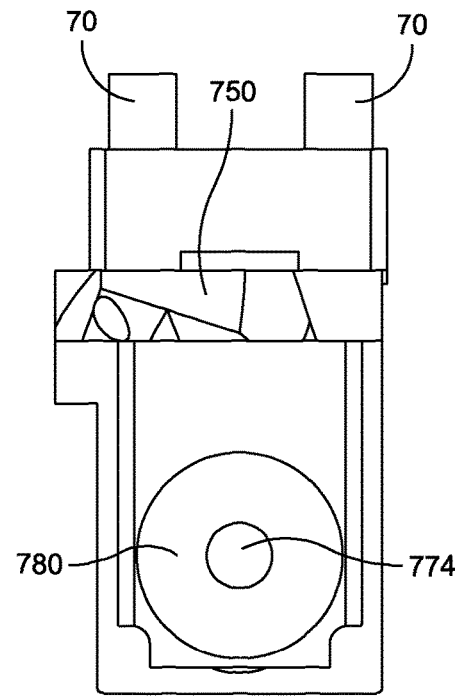
FIG. 54 is a bottom side plan view of the assembly illustrated in FIG. 51.

As illustrated in FIGS. 49-54, mounting plate 800 may be coupled to tibial drill guide mount 700 using dowel pins 70, which are received through holes 822 and 734. Tibial drill guide cartridge 702 is received through aperture 804 and recess 718 as best seen in FIG. 51. FIGS. 53 and 54 illustrate that when tibial drill guide cartridge 702 is properly inserted into the assemblage of tibial drill guide mount 700 and mounting plate 800, hole 772 aligns with hole 828 defined by mounting plate 800, which may include a ball detent (not shown) disposed therein. Consequently, the ball detent is received within hole 772 to retain tibial drill guide cartridge 702 disposed within aperture 804 and recess 718 such that hole 774 is disposed within recesses 754 and 756. A screw or other threaded object (not shown) can be inserted into threaded hole 770 and then pulled to remove tibial drill guide cartridge 702 from aperture 804 and recess 718 as illustrated in FIGS. 53 and 54.

Tibial drill guide mount 700, tibial drill guide 702, and mounting plate 800 may be used in connection with alignment tool 300, adapter bar 400, foot holder assembly 500, and alignment tool 600 as described above. Additionally, tibial drill guide mount 700, tibial drill guide 702, and mounting plate 800 may also be used in conjunction with foot holder assembly 900 illustrated in FIGS. 55-60 as can tibial drill guide mount 200 and tibial drill guide 202.

Figure 55:
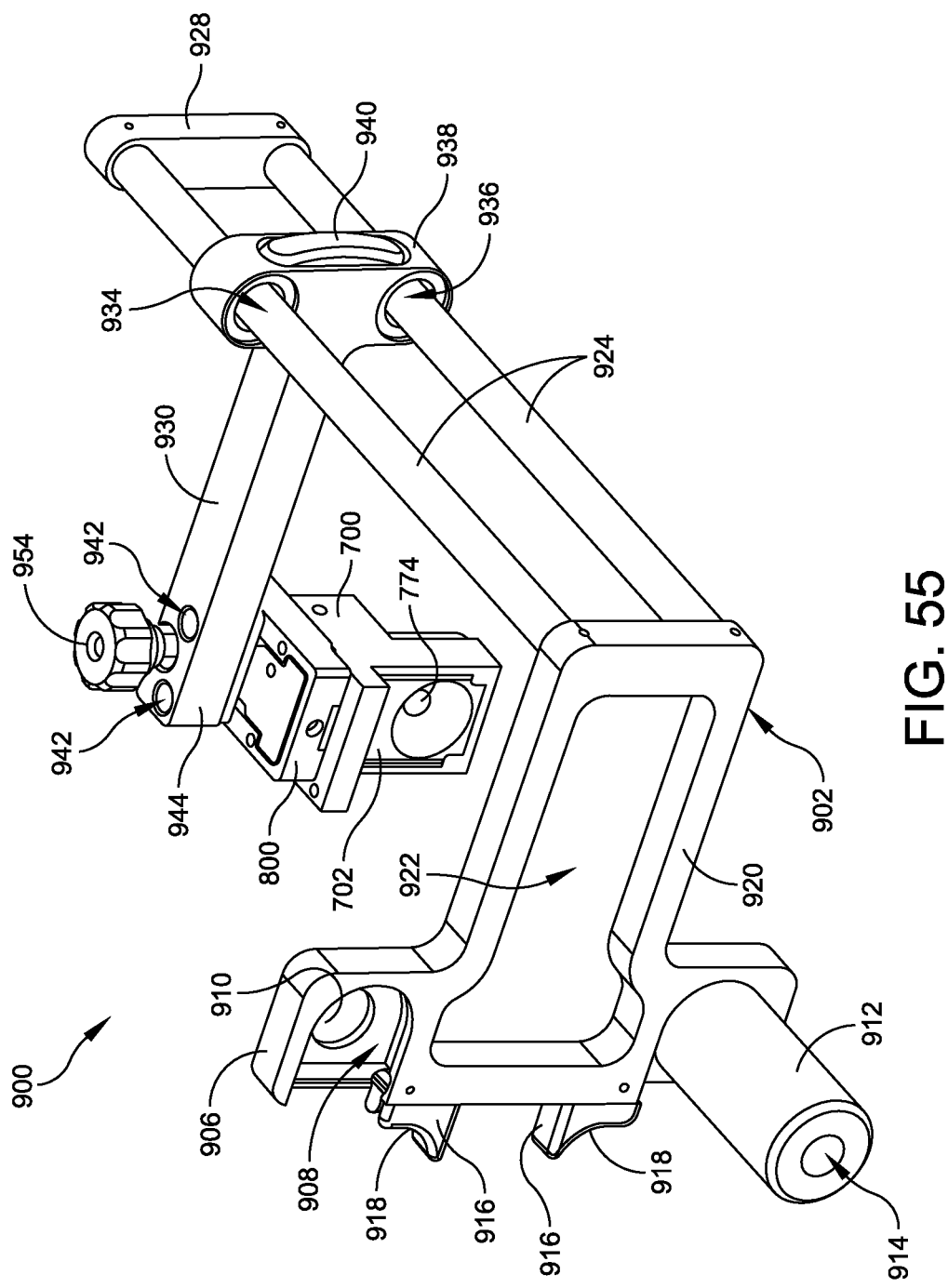
FIG. 55 is a perspective view of a foot holder assembly for use with the assembly illustrated in FIG. 51.

As shown in FIG. 55, foot holder assembly 900 includes a base plate 902 that extends from a first end 904 to a second end 906. First and second ends 904, 906 each define a pocket 908 and a hole 910. Pocket 908 is sized and configured to receive a drill bushing 912 having a cylindrical body defining hole 914 that aligns with through hole 910. Accordingly, both first end 904 and second end 906 may support an ankle or forefoot of a patient. Each pocket 908 includes a spring loaded detent 916 communicatively coupled to it that include a finger receiving surface 918 and is configured to slide relative to base plate 902 and secure drill bushing 912 within pocket 908. In some embodiments, drill bushing may be threaded and configured to be coupled to base plate 902 with complementary threads disposed on an inner surface of holes 910.

Base plate 902 also includes a medial/lateral extension 920 that extends in a substantially perpendicular direction from an approximate mid-point between first end 904 and second end 906. Base plate 902 may also define a viewing opening 922 such that a surgeon may be able to view the bottom of a patient's foot when the foot is secured to foot holder assembly 900.

Figure 56:
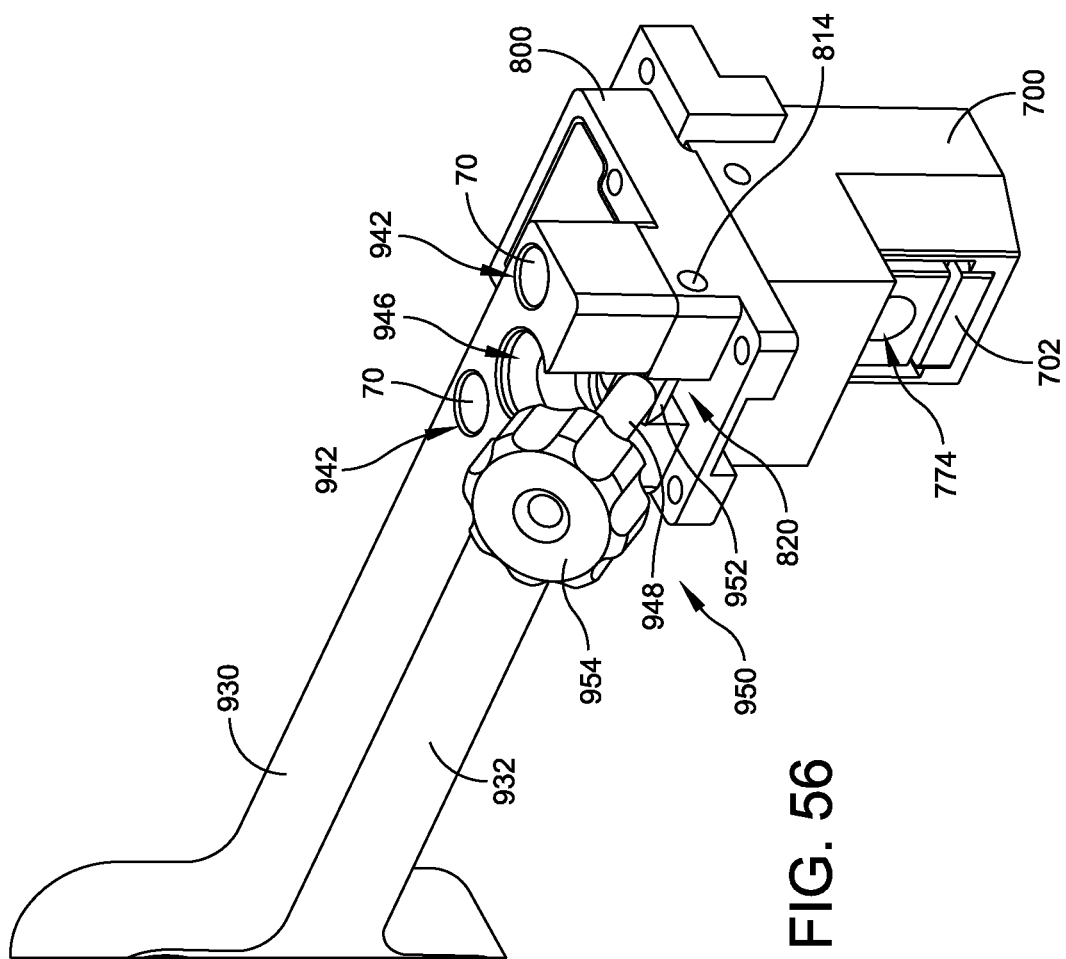
FIG. 56 is a perspective view of a pivoting arrangement used to secure the assembly illustrated in FIG. 51 to the foot holder assembly.
Figure 57:
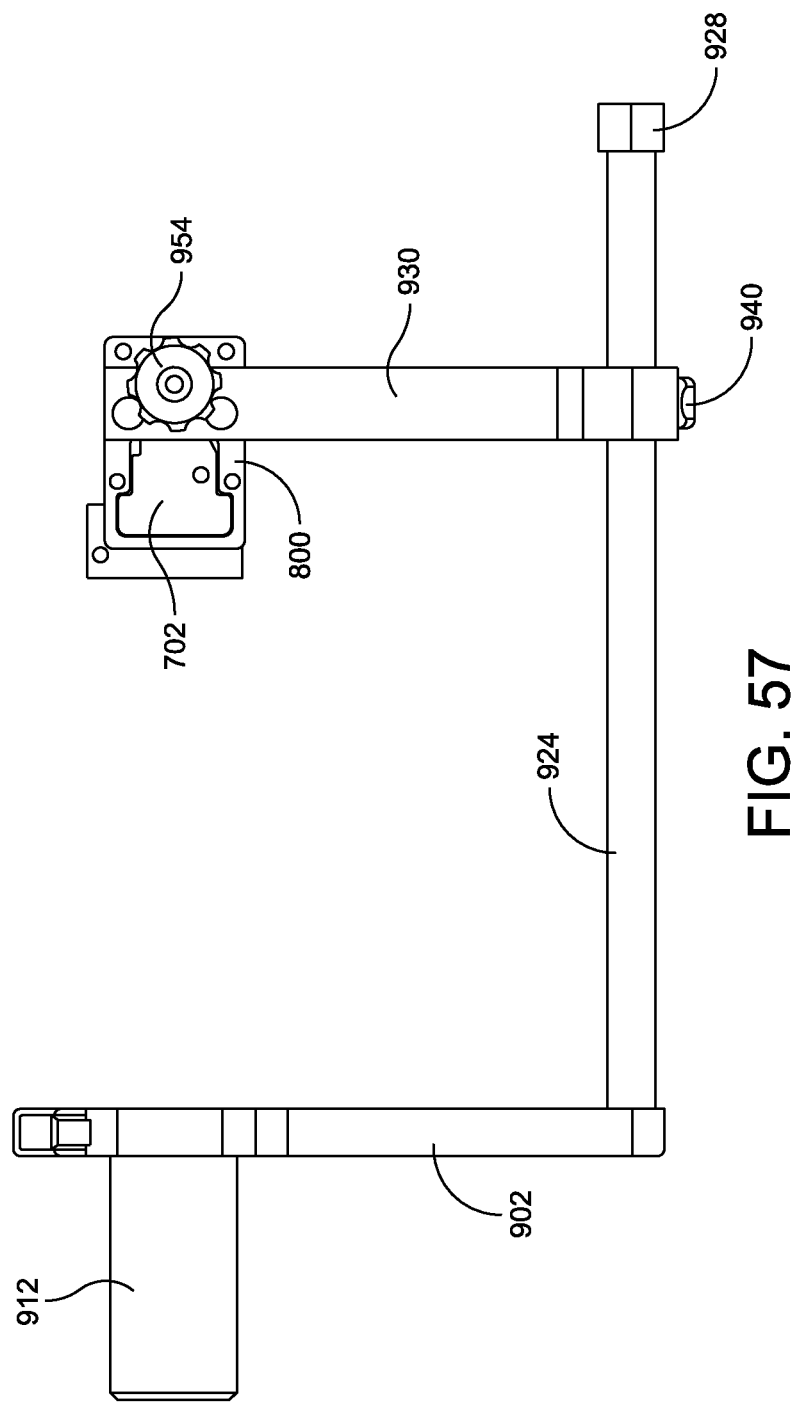
FIG. 57 is a top side plan view of the foot holder assembly illustrated in FIG. 55.
Figure 58:
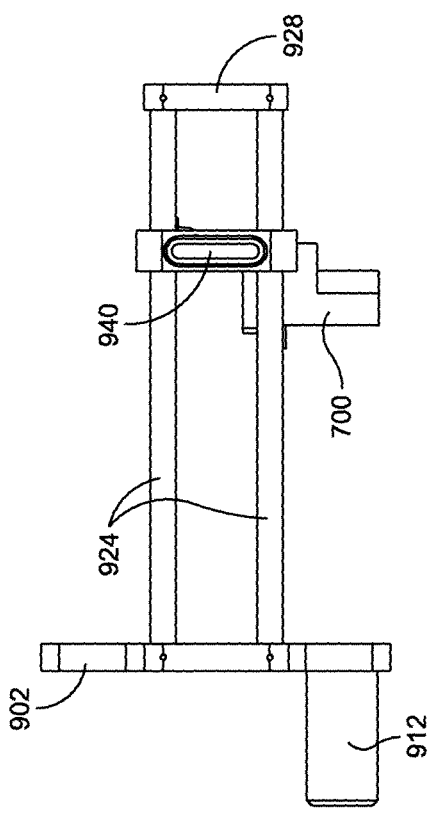
FIG. 58 is a side view of the foot holder assembly illustrated in FIG. 55.
Figure 59:
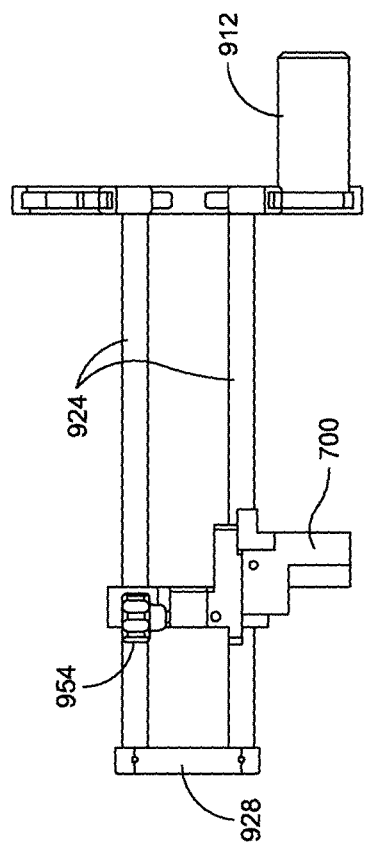
FIG. 59 is an opposite side view of the foot holder assembly illustrated in FIG. 55.
Figure 61:
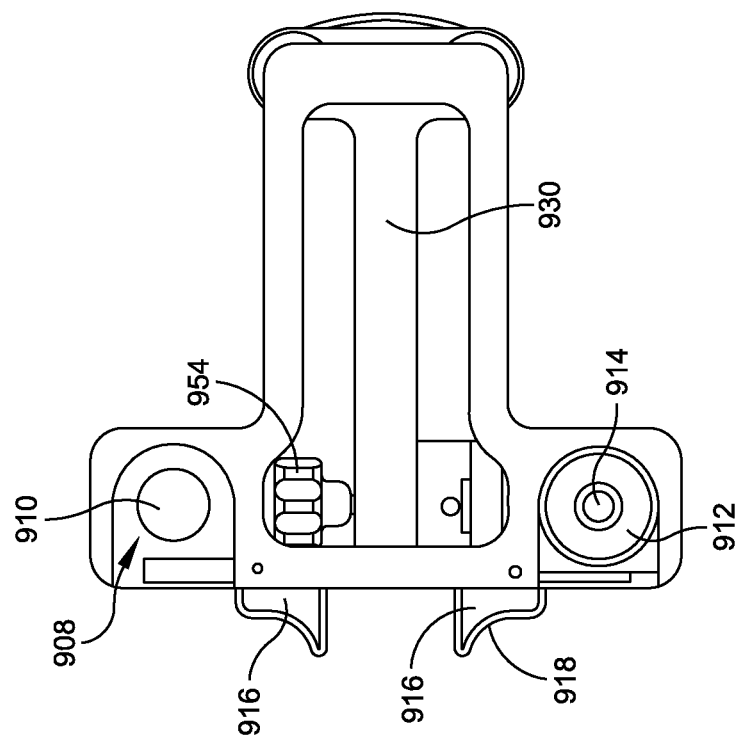
FIG. 61 is a front end view of the foot holder assembly illustrated in FIG. 55.

One or more rods 924 extend from base plate 902 in a substantially perpendicular direction with respect to an upper foot holding surface 926 (FIG. 56). Rods 924 may be secured to base plate 902 using screws or through other securing means as will be understood by one skilled in the art. A cap 928 is secured to an upper end of rods 924 and be secured to rods 924 using screws or other fixation means.

A mounting member 930 has an elongate body 932 that defines a pair of holes 934, 936 at one end 938 that slidably receive rods 924 such that mounting member 930 may be slid along rods 924 in order to position tibial drill guide mount 700 with respect to base plate 902. A spring loaded button 940 is disposed at first end 938 of mounting member 930 and is coupled to a locking mechanism (not shown) disposed within mounting member 930 for locking mounting member 930 at a position along rods 924.

Figure 60:
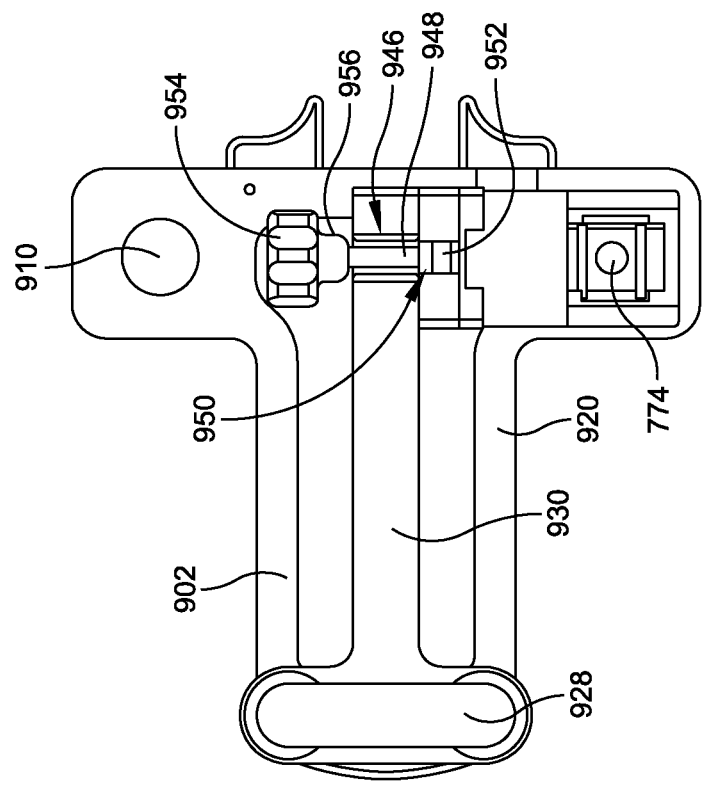
FIG. 60 is a rear end view of the foot holder assembly illustrated in FIG. 55.
Figure 62:
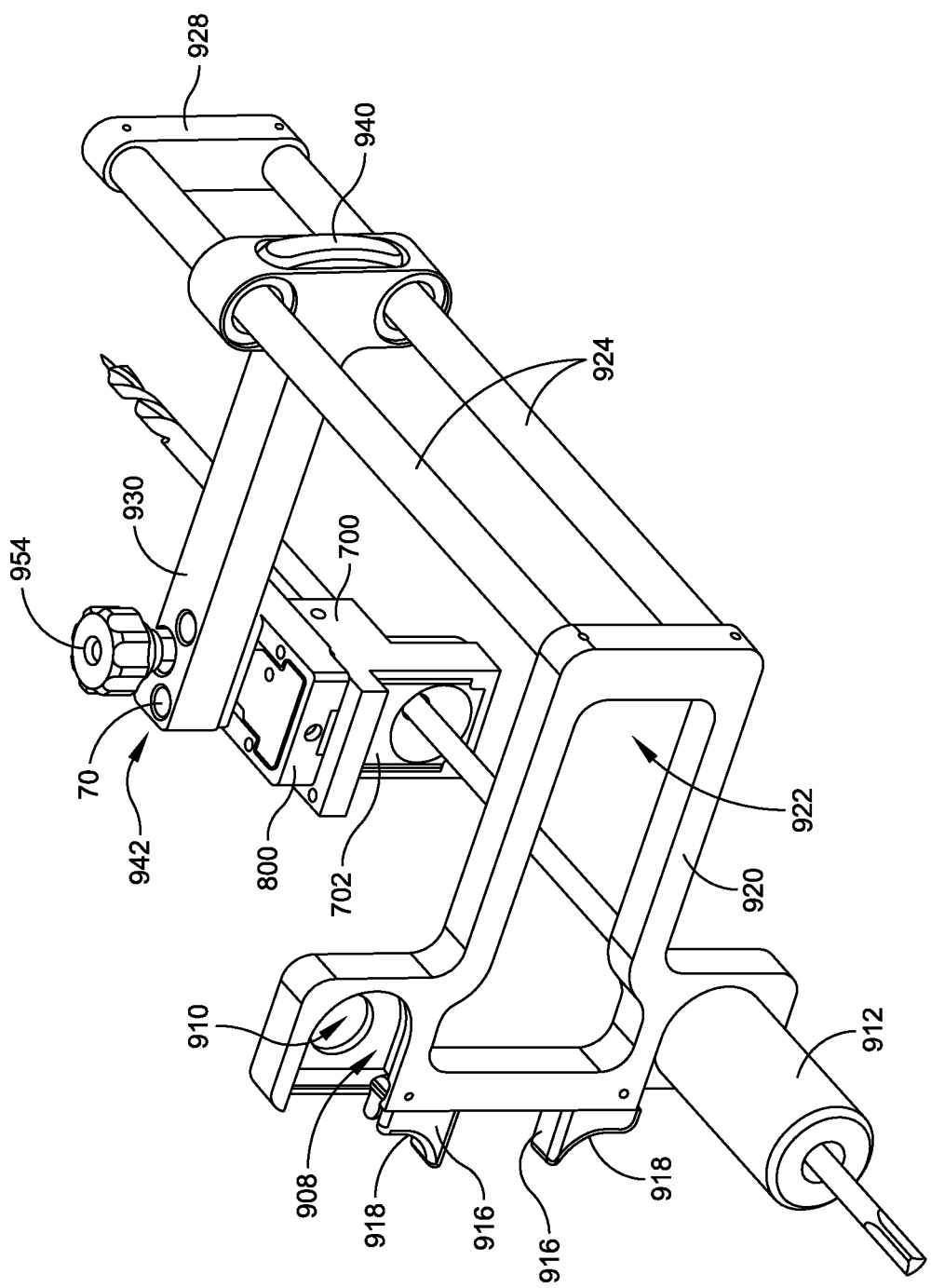
FIG. 62 is a perspective view of a drill being extended through the foot holder assembly and tibial drill guide.

One or more holes 942 are defined at the second end 944 of mounting member 930 and correspond to holes 716 of drill guide mount 700 for coupling drill guide mount 700 to foot holder assembly 900. Second end 942 also defines a slot 946, as best seen in FIGS. 56 and 60, that is sized and configured to receive an internally threaded rod 948 of a pivoting arrangement 950, which includes a lower portion 952 that is received within slot 820 of mounting plate 800 and is cross-pinned through hole 814. The cross-pinning of pivoting arrangement 950 may pivot about an axis defined by hole 814 and is configured to receive an support tightening knob 954. Bottom surface 956 (FIG. 60) of knob 954 has an outer dimension that is greater than slot 946 and is configured to engage mounting member 930 in order to secure the assemblage of mounting plate 800 and tibial drill guide mount 700, which may include tibial drill cartridge 702.

In operation, tibial drill guide mount 700 is inserted into resected joint space 22. Mounting plate 800 is connected to tibial drill guide mount 700 using dowel pins 70 as best seen in FIGS. 49 and 50. With pivoting arrangement 950 cross-pinned to mounting plate 800, the assemblage of mounting plate 800 and pivoting arrangement 948 is coupled to tibial drill guide mount with dowel pins 70, which may be press fit into holes 822 of mounting plate 800 and holes 716 of tibial drill guide mount 700 as will be understood by one skilled in the art. Tibial drill guide mount 700 and mounting plate may be secured within resected joint space 22 by inserting k-wires (not shown) into holes 736, 790 defined by tibial drill guide mount 700 and holes 830-1, 830-2 (corresponding to holes 736-1, 736-2) and 832-1, 832-2 defined by mounting plate 800.

With mounting plate 800 coupled to tibial drill guide mount 700 that is disposed within resected joint space 22, pivoting arrangement 948 is rotated such that it extends in a direction approximately parallel to a longitudinal axis defined by a patient's leg and the cartridge-style tibial drill guide 702 is inserted into aperture 804 of mounting plate 800 and recess 718 of tibial drill guide mount 700. Tibial drill guide cartridge 702 is inserted until leading end 786 of tibial drill cartridge 702 abuts rear wall 788 of tibial drill guide mount 700 at which point the ball detent disposed within hole 772 engages hole 828 defined by mounting plate 800 and the front side 768 of tibial drill guide cartridge 702 is flush with front side 806 of mounting plate 800.

Holes 940 of mounting member 930 are aligned with, and received over, dowel pins 70 that extend from front side 806 of mounting plate to couple mounting member 930 of foot holder assembly 900 to the assemblage of mounting plate 800, tibial drill guide mount 700, and tibial drill guide cartridge 702. With mounting member 903 coupled to dowel pins 70 and mounting plate 800, pivoting arrangement 948 is rotated with respect to mounting plate 800 such that rod 946 of pivoting arrangement 948 is received within slot 944 of mounting member 930. Knob 952 is then rotated about its axis (clockwise or counterclockwise) such that the bottom surface 954 of knob 952 contacts mounting member 930 to maintain engagement between mounting member 930 and the assemblage of tibial drill guide mount 700 and mounting plate 800.

Drill bushing 912 is coupled to hole 910 that is aligned with the heel of a patient's foot. As described above, drill bushing 912 may be slid into pocket 908 defined by bottom plate 902 until spring loaded detents 916 releasably lock drill bushing 912 in place. In some embodiments, drill bushing 912 may be screwed into base plate 902 by way of corresponding threads disposed on an outer surface of drill bushing 912 that engage threads defined by an inner surface of pocket 908 and/or hole 910. With drill bushing 912 in place and the patient's leg secured to foot holder assembly 900, various minimally invasive surgical techniques may be used to introduce a bottom foot cannula into the calcaneus 20, talus 14, and tibia 16 as described above.

Once access to the patent's calcaneus has been achieved, a bottom foot cannula 64 is inserted through the patient's calcaneus 20. A reamer 66 is operated through the cannula 64 to drill approximately another through the talus 14 and up into the tibia 16 to establish an intramedullary guide path through the calcaneus 20 and talus 14 leading into the tibia 16. As reamer 66 exits talus 14, the conically shaped internal surface 748 guides the tip 68 into hole 788. An axis defined by hole 788 is substantially axially aligned with a mechanical axis of tibia 16 such that as reamer 66 is extended through hole 788, it bores an intramedullary canal within tibia 16.

Reamer Stabilizer

Figure 63:
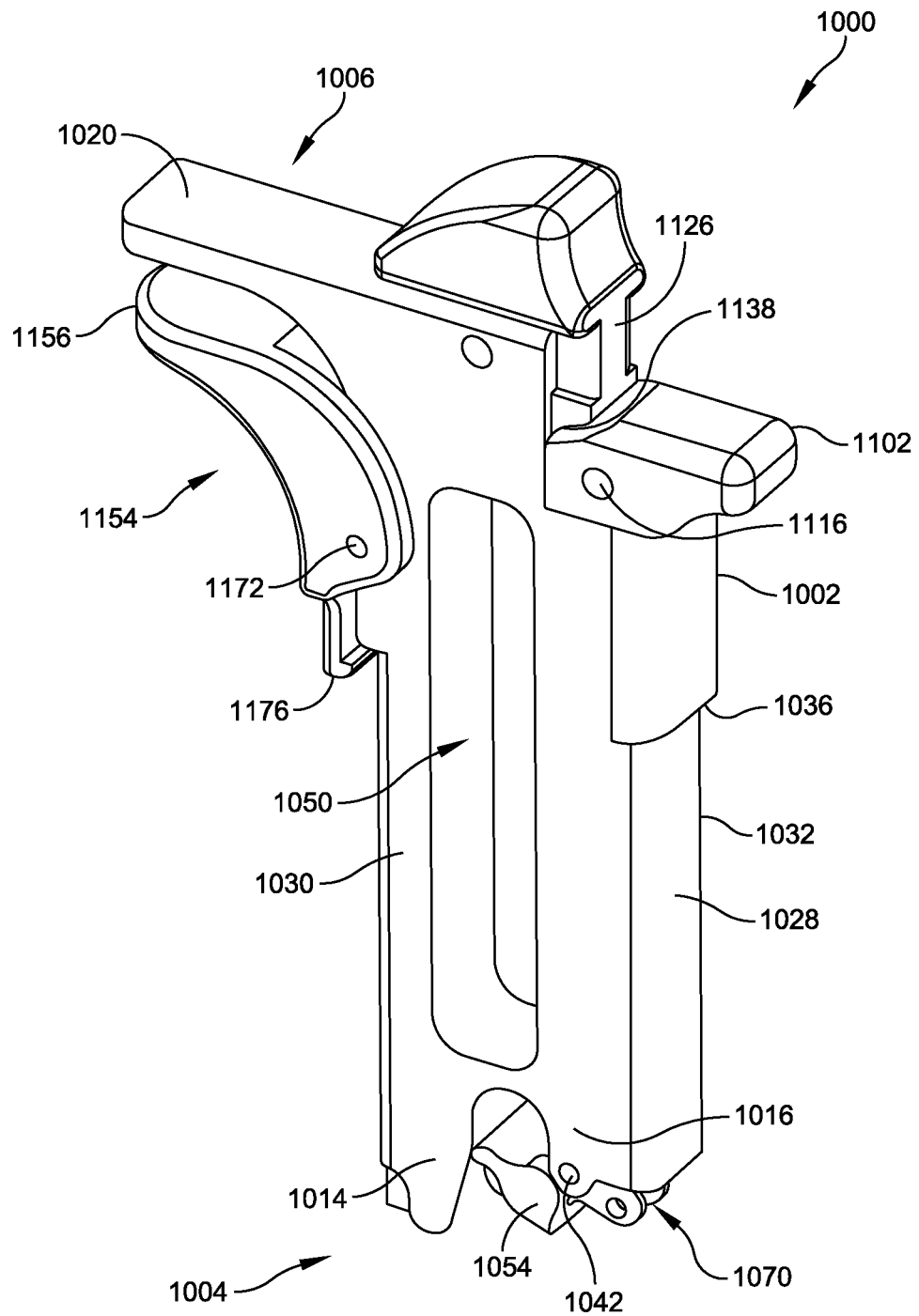
FIG. 63 is an isometric view of one example of a reamer stabilizer in accordance with some embodiments.

FIGS. 63-70 illustrate one example of a reamer stabilizer 1000 that may be used to stabilize the reamer as it is advanced into the tibia of a patient. Referring first to FIG. 63, reamer stabilizer 1000 includes an elongate body 1002 extending from a distal end 1004 to a proximal end 1006. As best seen in FIGS. 64 and 65, body 1002 defines a longitudinal channel 1008 extending along the length of body

1002. Body 1002 also defines a pair of cavities 1010, 1012 for receiving buttons and biasing members as described in greater detail below.

Distal end 1004 of body 1002 includes a pair of spaced apart prongs 1014, 1016. In some embodiments, prong 1014 has a length that is longer than a length of prong 1016. As shown in FIGS. 64 and 65, longitudinal channel 1008 extends along prong 1016. A notch 1018 is defined between prongs 1014 and 1016.

Figure 66:
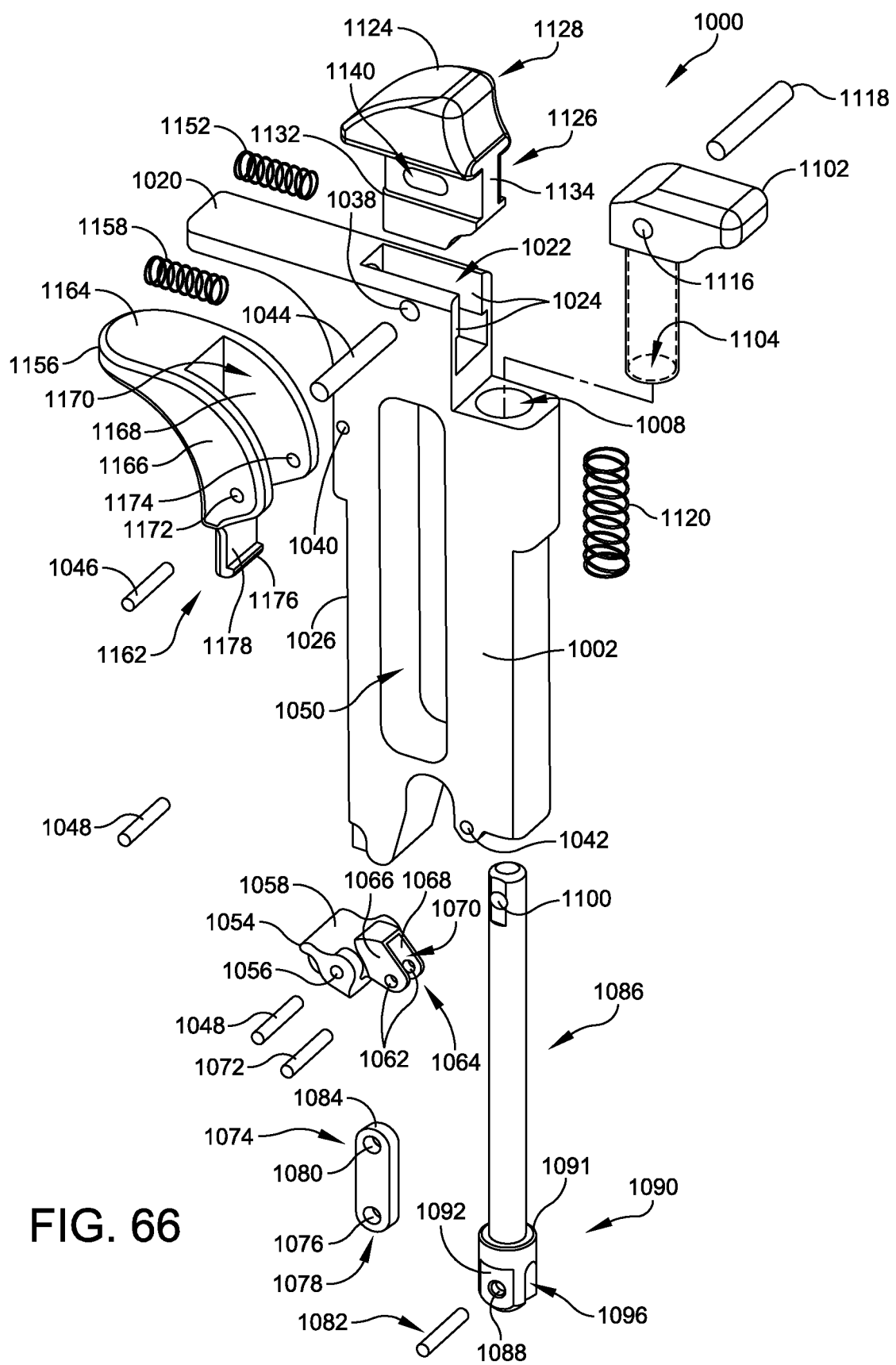
FIG. 66 is an exploded isometric view of the reamer stabilizer illustrated in FIG. 63.
Figure 68:
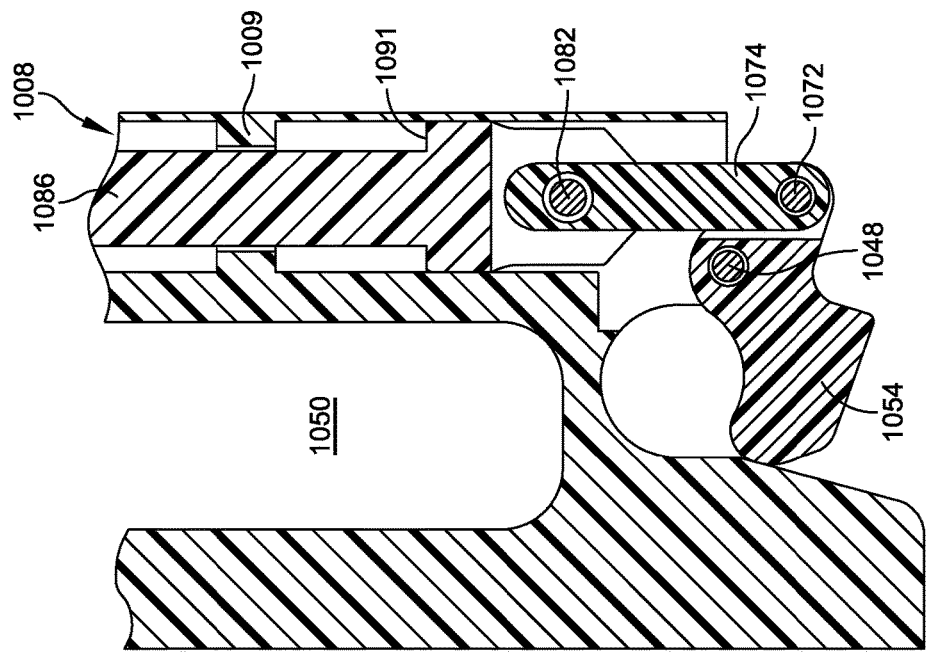
FIGS. 67 and 68 are cross-sectional detailed view of the coupling assembly of the reamer stabilizer illustrated in FIG. 63 during various stages of operation.
Figure 67:
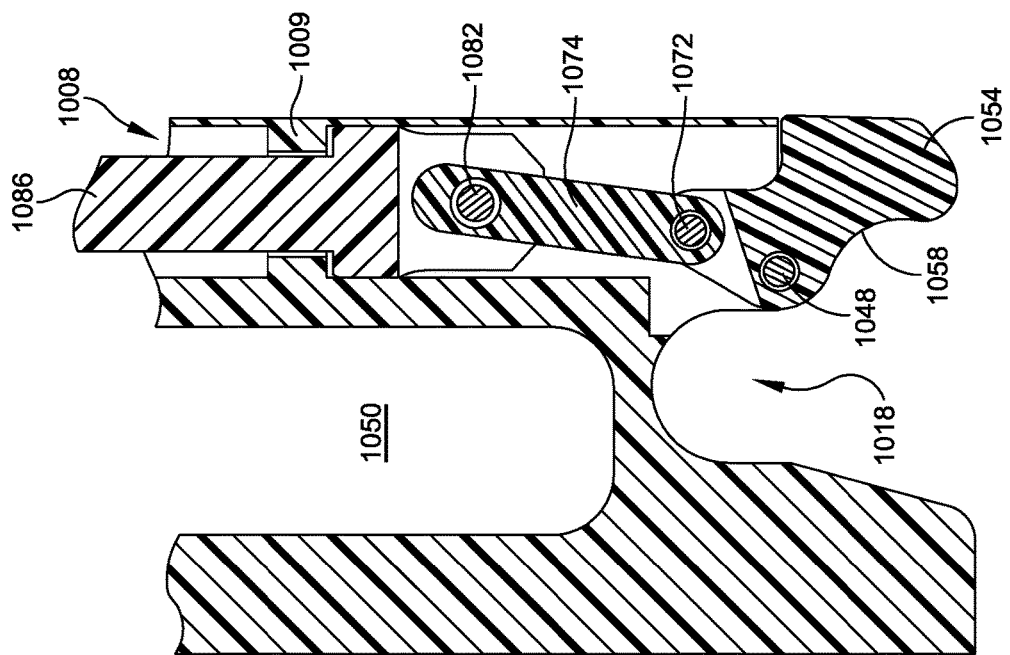

Proximal end 1004 includes a handle 1020 that extends at from body 1002 at an angle relative to the longitudinal axis defined by body 1002 as best seen in FIG. 63. Opposite handle 1020 proximal end 1006 includes a cutout region 1022 defined by a pair of perpendicular walls 1024, 1024 as illustrated in FIG. 66. Although walls 1024 are illustrated and described as perpendicular to one another, one of ordinary skill in the art will understand that cutout region 1022 may be defined by walls having other configurations.

In some embodiments, body 1002 has a rectangular cross-sectional geometry defined by four sides 1026, 1028, 1030, 1032. Opposed sides 1026, 1028 each include a respective step 1034, 1036 along their respective lengths. Steps 1034, 1036 are positioned at a same distance from notch 1018.

Opposed sides 1030, 1032 defines holes 1038, 1040, 1042 each configured to receive a respective pin 1044, 1046, 1048 in a press-fit engagement as described below. Hole 1038 is positioned near proximal end 1006. Hole 1040 is disposed adjacent to wall 1026 and step 1034. Hole 1042 is formed in prong 1016. In some embodiments, opposed sides 1030, 1032 define an opening 1050, which reduces the overall weight of reamer stabilizer 1000 and provides a surgeon or user with additional surfaces to manipulate reamer stabilizer 1000.

As best seen in FIGS. 64 and 65, a slidable guiding assembly 1052 is disposed within longitudinal channel 1008. Guiding assembly 1052 includes a reamer guide body 1054 that is pivotably coupled to stabilizer body 1002 by pin 1048, which is received within hole 1056. Reamer guide body 1054 includes a concave guiding surface 1058 disposed adjacent to hole 1056. Opposite concave guiding surface 1058 guide body 1054 includes a step 1060, which is disposed adjacent to a hole 1062, which is defined in a forked end 1064 of guide body 1054. Formed end 1064 is formed by a pair of spaced apart tabs 1066, 1068 that together define a recess 1070 therebetween.

A pin 1072 (FIGS. 66 and 67) is received in hole 1062 of reamer guide body 1054 for pivotably coupling reamer guide body 1054 to pivot rod 1074, which includes a corresponding hole 1076 at its distal end 1078. Pivot rod 1074 defines another hole 1080 at its proximal end 1084. Hole 1080 is sized and configured to receive a pin 1082 for coupling pivot rod 1074 to plunger rod 1086.

Figure 69:
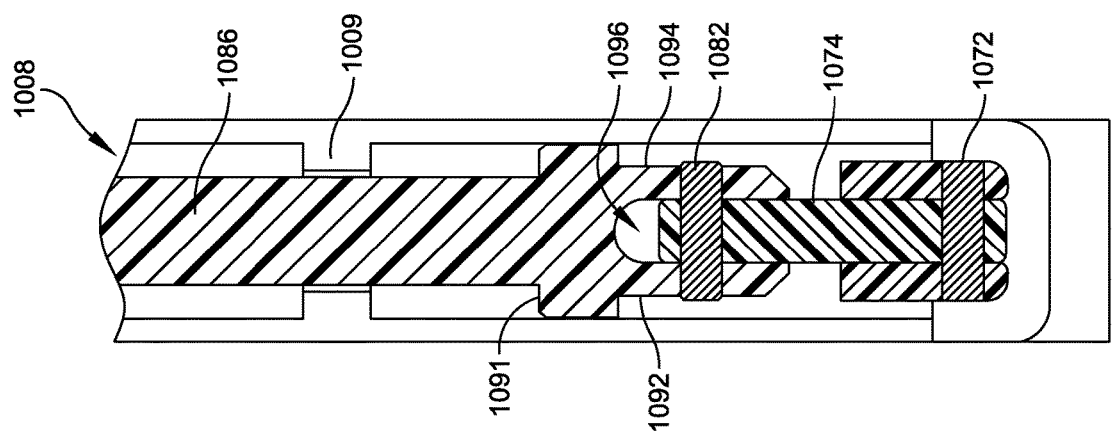
FIG. 69 is a cross-sectional detail view of the coupling between a plunger rod, pivot rod, and reamer guide body in accordance with the reamer stabilizer illustrated in FIG. 63.

As best seen in FIGS. 66-69, plunger rod 1086 defines a hole 1088 at its distal end 1090, which has a flared geometry relative to the remainder of plunger rod 1086. In some embodiments, distal end 1090 includes a pair of opposed flats 1092, 1094 and defines a slot 1096 as best seen in FIG. 69 in which pivot rod 1074 is received. Distal end 1090 also forms a shoulder 1091 configured to maintain plunger rod 1086 within longitudinal channel 1008 as described in greater detail below.

Figure 70:
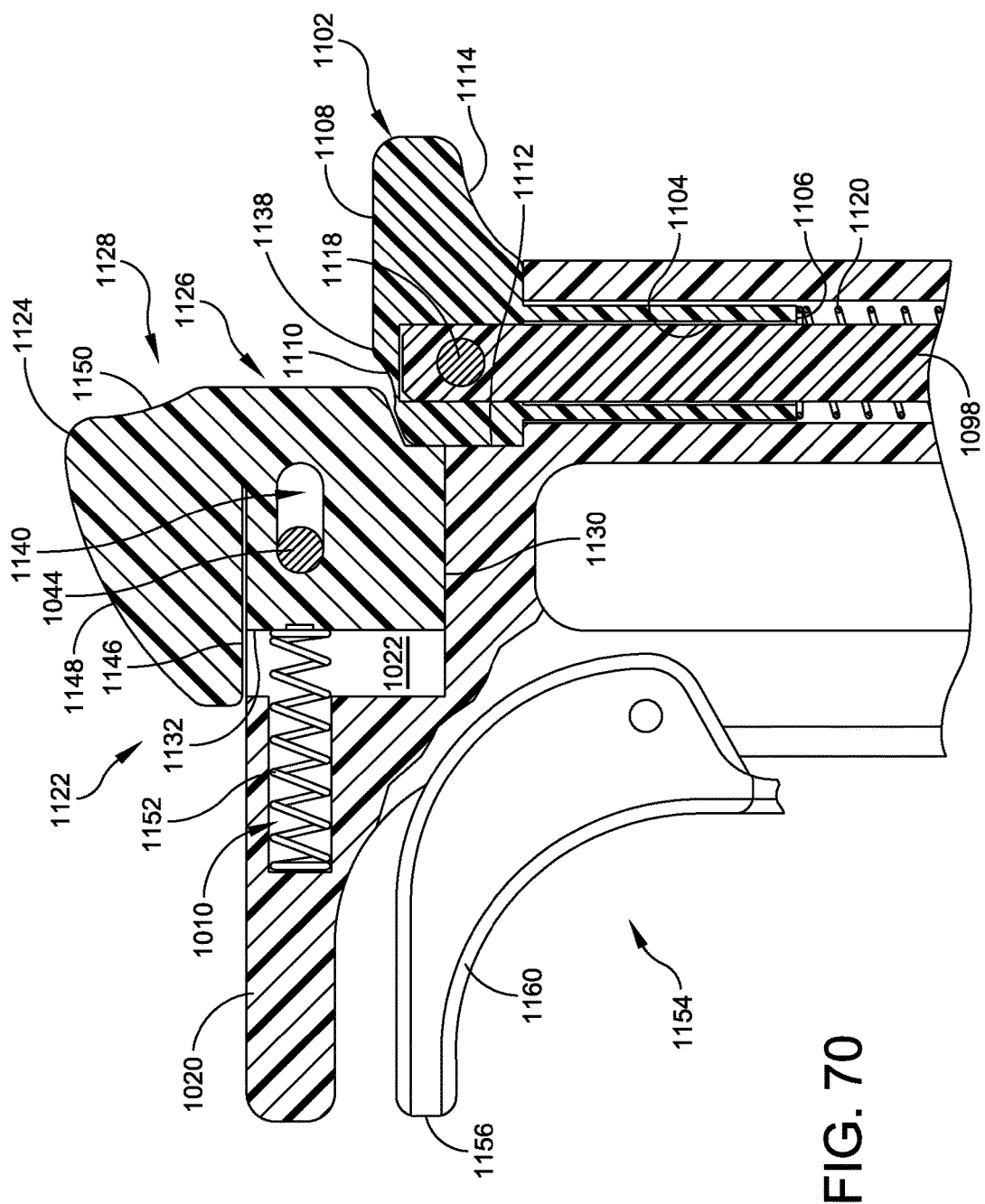
FIG. 70 is a cross-sectional detail view of the locking assembly of the reamer stabilizer illustrated in FIG. 63.

Proximal end 1098 of plunger rod 1086 defines a hole 1100 that is size and configured to receive a pin 1118 for coupling plunger rod 1086 to head 1102. Head 1102 defines a blind hole 1104 that inwardly extend from distal end 1106 and is sized and configured to receive proximal end 1098 of plunger rod 1086 therein. In some embodiments, top side 1108 of head 1102 includes an angled surface 1110 that terminates at side 1112. Head 1102 also includes an arced surface 1114 for providing an ergonomic contour to a user's finger (FIG. 70). A hole 1116 extends through head 1102 in a direction that is perpendicular to the direction in which blind hole 1104 extends and is configured to align with hole 1100 of plunger rod 1086 for coupling plunger rod 1086 to head 1102 using pin 1118. Although a cross-pin arrangement is described, one of ordinary skill in the art will understand that other coupling means may be used to couple head 1102 to plunger rod 1086 including, but not limited to, a taper fit, ultrasonic welding, a snap fit arrangement, or the use of adhesive to list but only a few possibilities.

A biasing member 1120 is configured to be disposed over plunger rod 1086 and abut the distal end 1106 of head 1102. In some embodiments, biasing member 1120 is a compression spring that applies a biasing force to head 1102 in a proximal direction as biasing member 1120 is disposed between distal end 1106 and a reduced diameter area 1009 of longitudinal channel 1008.

Turning now to FIG. 70, locking assembly 1122 is disposed at the proximal end 1006 of reamer guide body 1002 and is configured to lock guiding assembly 1052 in a position in which guiding assembly 1052 engages a reamer body 65 as described in greater detail below. Locking assembly 1122 includes a locking button 1124 slidably coupled to reamer stabilizer body 1002. Locking button 1124 includes a lower portion 1126 that is configured to be received within cavity 1022 defined by stabilizer body 1002 and an upper portion 1128 extending above stabilizer body 1002 for facilitating engagement by a surgeon or other user.

In some embodiments, lower portion 1126 has a substantially rectangular geometry comprising a bottom surface 1130, an internal side surface 1132, and an outer side surface 1134. Bottom surface 1130 is flat and configured to slide along a surface of cavity 1010. The interface between bottom surface 1130 and outer side surface 1134 includes an angled surface 1138 that is complementary to angled surface 1110 of head 1102. A slot 1140 is defined by sides 1142, 1144. Slot 1140 extends parallel to bottom surface 1130 and is sized and configured to receive pin 1044, which is received through hole 1038 defined by stabilizer body 1002.

In some embodiments, upper portion 1128 has a triangular shape although one of ordinary skill in the art will understand that upper portion 1128 can take on other geometric shapes. Upper portion 1128 includes a substantially flat bottom surface 1146 configured to slide along an upper or proximal-most surface of handle 1020. Upper sides 1148, 1150 form the other two sides of upper portion 1128. Side 1150 is curved to facilitate ergonomic engagement with a finger of a surgeon or user.

A biasing member 1152 is disposed within cavity 1010 and is configured to urge locking button 1124 away from handle 1020 and towards guiding assembly 1052. In some embodiments, such as the embodiment illustrated in FIGS. 66-70, biasing member 1152 is a compression spring that is disposed in cavity 1010 in an abutting relationship with inner side surface 1132 of lower portion 1126 of locking button 1124. Biasing member 1152 is positioned such in cavity 1010 such that biasing member 1152 is substantially collinear with slot 1140 to prevent rotation and jamming of locking button 1124 as will be understood by one of ordinary skill in the art.

Coupling assembly 1154 is coupled to side 1026 of stabilizer body 1002 and is configured to couple reamer stabilizer 1000 to other surgical devices as described in greater detail below. Coupling assembly 1154 includes a pivoting button 1156 and a biasing member 1158. As best seen in FIG. 66, pivoting button 1156 has an arcuate body 1160 extending from a lower end 1162 to an upper end 1164. A pair of ears 1166, 1168 extend from an approximate middle of body 1160 that together define depression 1170. Each ear 1166, 1168 defines a respective hole 1172, 1174 for receiving pin 1046.

Lower end 1162 includes a detent 1176 extending from inner surface 1178 adjacent to depression 1170. A recess 1180, which is illustrated in FIGS. 64 and 65, is defined within depression 1170 at a location that is disposed proximally of holes 1172, 1174 defined by ears 1166, 1168. Detent 1176 is disposed distally of step 1034. The relative locations of detent 1176 with respect to step 1034 and recess 1180 with respect to holes 1172, 1174 are provided for coupling reamer stabilizer 1000 to other surgical device as described in greater detail below. Concave outer surface 1182 provides an ergonomic surface for the finger of a surgeon or user of reamer stabilizer 1000 when the reamer stabilizer 1000 is to be decoupled from other surgical devices.

To assemble reamer stabilizer 1000, guiding assembly 1052 is assembled by placing pivot rod 1074 within slot 1096 at the distal end 1090 of plunger rod 1086. Pivot rod 1074 is coupled to plunger rod 1088 by inserting pin 1082 through holes 1080 and 1100. Reamer guide body 1054 is coupled to the distal end 1078 of pivot rod 1074 by inserting pin 1072 into holes 1062 and 1076.

Proximal end 1098 of plunger rod 1086 is inserted into longitudinal channel 1008 at the opening at defined by 1016 at the distal end 1004 of stabilizer body 1002. When shoulder 1091 defined by distal end 1090 contacts reduced diameter area 1009 of longitudinal channel 1008, proximal end 1098 of plunger rod 1086 outwardly extends from longitudinal channel 1008. Biasing member 1116 is inserted into longitudinal channel 1008 over plunger rod 1086 as is head 1102. Hole 1116 of head 1102 is aligned with hole 1100 of plunger rod 1086 and the two pieces are coupled together by inserting pin 1118 through holes 1116 and 1100. Reamer guide body 1054 is coupled to stabilizer body 1002 by inserting pin 1048 through holes 1042 and 1056.

With guiding assembly 1052 coupled to stabilizer body 1002, locking assembly 1122 is coupled to stabilizer body 1002. Locking assembly 1122 is coupled to stabilizer body 1002 by inserting biasing member 1152 into cavity 1010 defined by body 1002. Lower portion 1126 of locking button 1124 is inserted into cavity 1010 until slot 1140 defined by lower portion 1126 aligns with hole 1038 defined by body 1002. With slot 1140 aligned with hole 1038, pin 1044 is inserted into hole 1038 and slot 1140 to cross-pin locking button 1124 to body 1002.

Coupling assembly 1154 is installed by inserting biasing member 1158 into cavity 1012, and pivoting button 1156 is placed over biasing member 1158 such that holes 1172, 1174 defined by ears 1166, 1168 aligns with hole 1040 defined by body 1002. With holes 1166, 1168 aligned with hole 1040, pin 1046 is inserted into the holes 1166, 1168, and 1040 to secure pivoting button 1156 to body 1002.

Foot Holder Assembly

Figure 71:
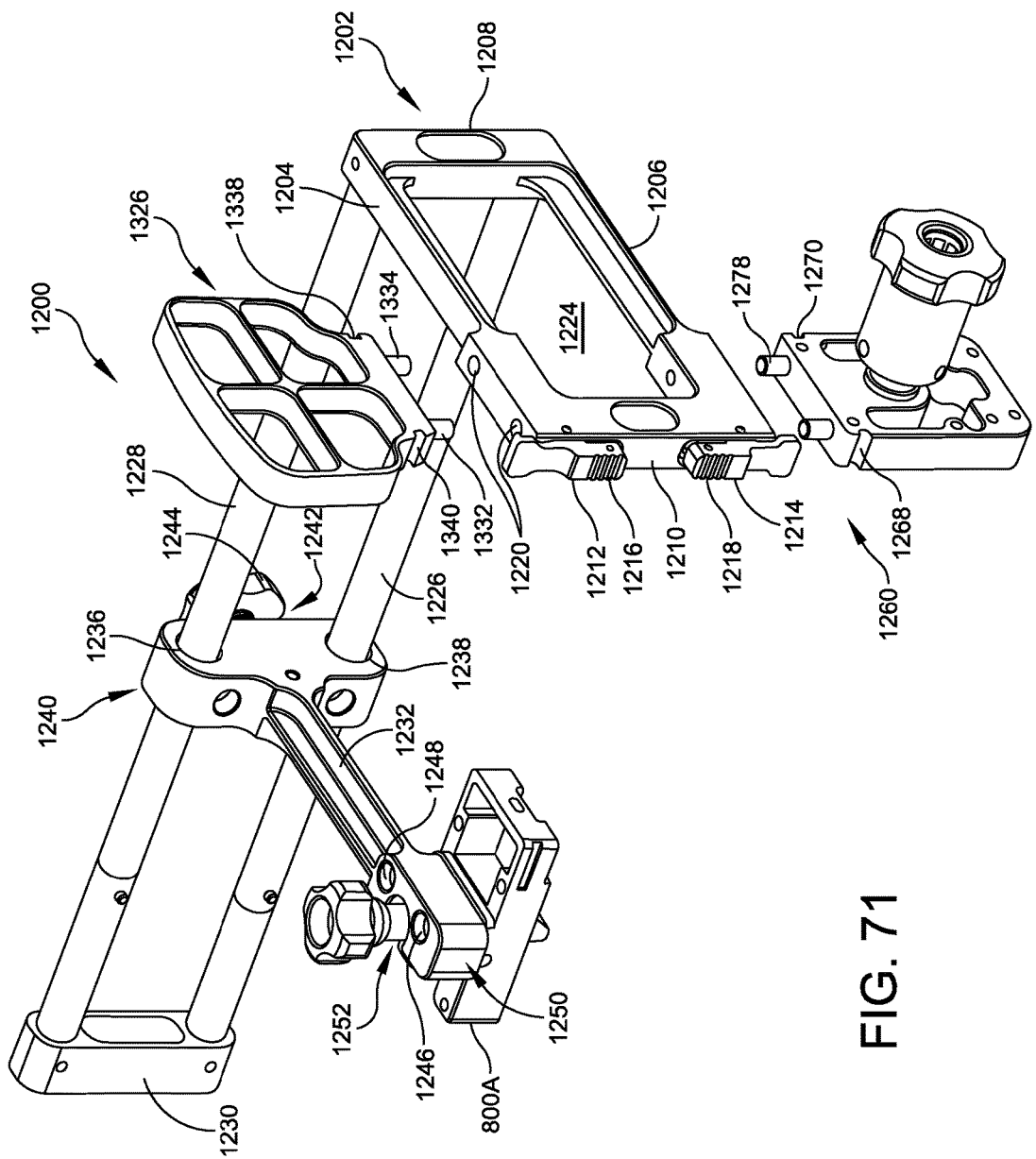
FIG. 71 is an isometric view of an embodiment of a foot holder assembly.

Reamer stabilizer 1000 is configured to be used in connection with a foot holder assembly such as foot holder assembly 1200 illustrated in FIG. 71. Foot holder assembly 1200 includes a base plate 1202 having a generally rectangular shape extending from a first side 1204 to a second side 1206 an from a third side 1208 to a fourth side 1210.

A pair of biased detents 1212, 1214 are disposed at opposite ends of side 1210 and are configured to couple foot plate 1326 and drill guide assembly 1260 to one of sides 1204, 1206 of base plate 1202 as described in greater detail below. Foot plate 1326 and drill guide assembly 1260 can advantageously be coupled to either of sides 1204, 1206 such that foot holder assembly 1200 is reversible and can be used for an operation on a patient's left and/or right foot and ankle Detents 1212, 1214 each include a respective finger-engaging surface 1216, 1218 that are manipulated by a surgeon or other user to disengage foot plate 1326 and/or drill guide assembly 1260 from base plate 1202.

Sides 1204, 1206 of base plate 1202 each define a pair of holes 1222, 1224 that are sized and configured to receive pegs 1332, 1334 of foot plate 1326 and pegs 1276, 1278 of drill guide assembly 1260 as described in greater detail below. Sides 1204, 1206, 1208, 1210 collectively define a viewing opening 1224 such that a surgeon may be able to view the bottom of a patient's foot when the foot is secured to foot holder assembly 1200.

One or more rods 1226, 1228 extend from side 1208 of base plate 1202 in a perpendicular direction with respect to the direction in which sides 1204 and 1206 extend from side 1208. In some embodiments, rods 1226, 1228 are secured to base plate 1202 using screws although one of ordinary skill in the art will understand that other securing means for securing rods 1226, 1228 to base plate 1202 can be used. A cap 1230 is coupled to the ends of rods 1226, 1228 opposite the ends to which base plate 1202 is coupled. Cap 1230 can also be coupled to rods 1226, 1228 using screws or other securement means.

A mounting member 1232 having an elongate body 1234 that defines a pair of holes 1236, 1238 at one end 1240 for slidably receiving rods 1226, 1228. A locking screw 1242 comprising a knob 1244 provides a locking mechanism for locking mounting member 1232 at a certain position along rods 1226, 1228. One or more holes 1246, 1248 are defined at the second end 1250 of mounting member 1232 and correspond to holes 736 of drill guide mount 700 and holes 822 of modified mounting plate 800A, which is described in greater detail below. Second end 1250 also defines a slot 1252 that is sized and configured to receive an internally threaded rod 948 of pivoting arrangement 950.

Figure 72:
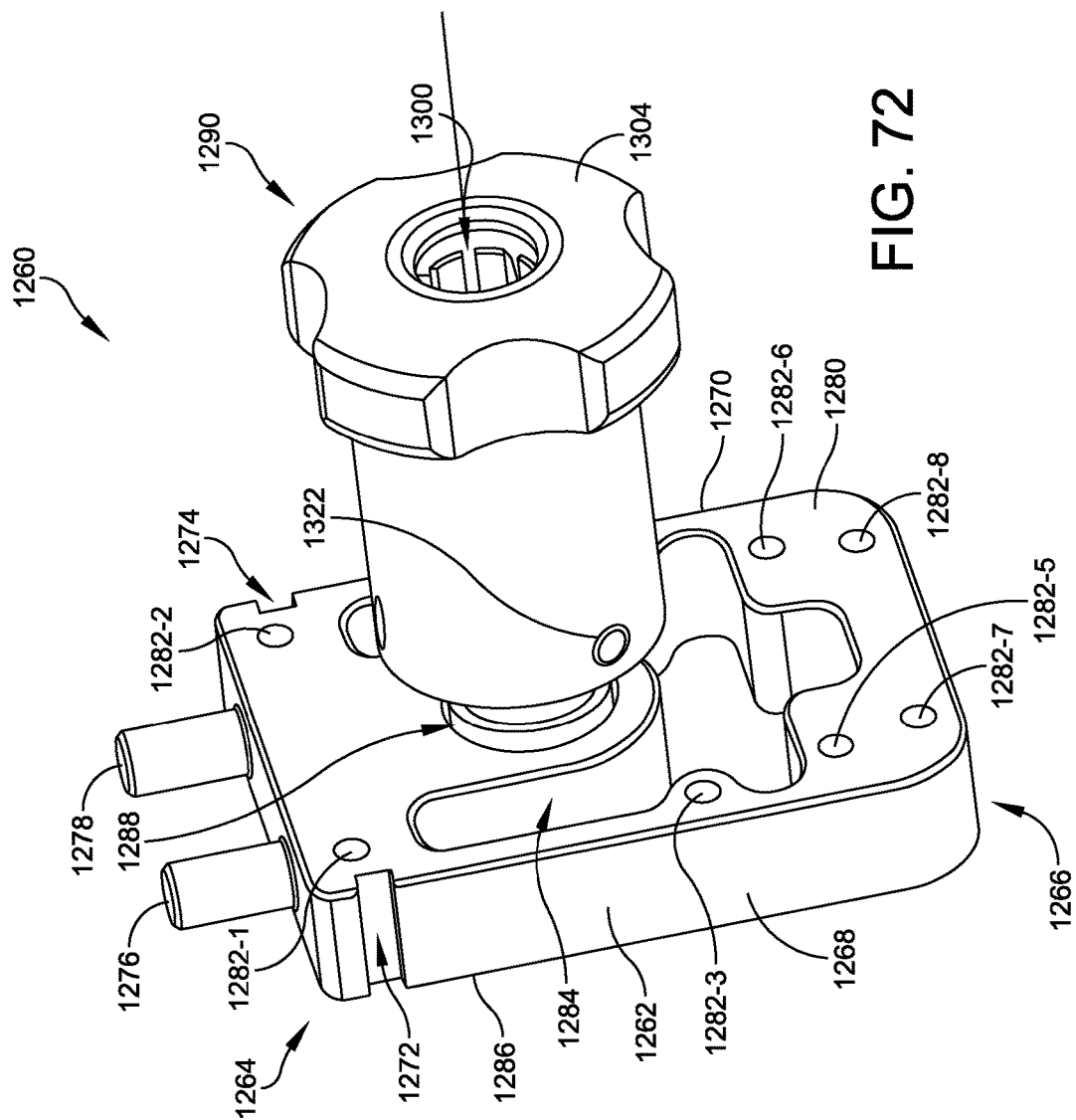
FIG. 72 is an isometric view of one example of a drill guide assembly that is configured to be releasably coupled to the foot holder assembly illustrated in FIG. 71.

Drill guide assembly 1260 is now described with reference to FIGS. 72-73. Referring first to FIG. 72, drill guide assembly 1260 includes a rectangular base 1262 extending from a coupling end 1264 to an opposite end 1266. Sides 1268, 1270 extend between ends 1264, 1266 and each define a respective recess 1272, 1274 adjacent to coupling end 1264. Pegs 1276, 1278 extend from coupling end 1264 and are sized and configured to be received within holes 1220, 1222 defined by sides 1204, 1206 of foot holder assembly 1200. Although two pegs 1276, 1278 are illustrated, one of ordinary skill in the art will understand that fewer or more pegs may be implemented.

Top side 1280 defines one or more holes 1282-1, 1282-2, 1282-3, 1282-4, 1282-5, 1282-6, 1282-7, 1282-8 ("holes 1282") for receiving k-wires. An opening 1284 is defined by top side 1280 and extends through base 1262 to patient-contact side 1286, which is disposed opposite top side 1280. Opening 1284 enables a surgeon or other professional to view the bottom of a patient's foot. A passageway 1288 also extends through base 1262 and is sized and configured to receive a locking bushing assembly 1290.

Figure 73:
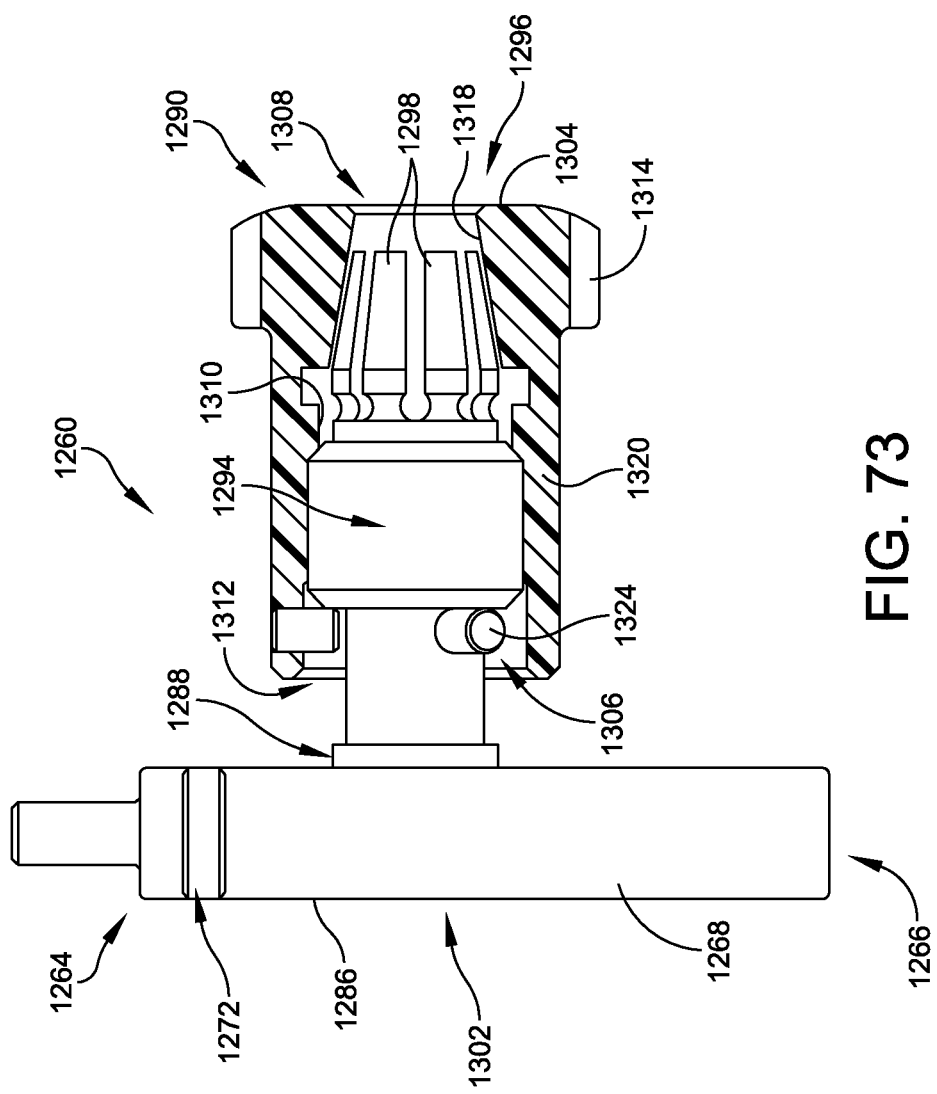
FIG. 73 is a partial cross-sectional view of the drill guide assembly illustrated in FIG. 72.

As best seen in FIG. 73, locking bushing assembly 1290 includes a central member 1292 that is coupled within passageway 1288. Central member 1292 includes a threaded flared region 1294 that is disposed adjacent to end 1296. A plurality of flexible prongs 1298 are disposed at end 1296 and have a tapered configuration that narrows from flared region 1294 to end 1296. Central member 1292 defines a bore 1300 extending from end 1296 to end 1302. Bore 1300 is sized and configured to receive a drill bushing as described in greater detail below.

A knob 1304 defines an internal space 1306 and a hole 1308 that aligns with bore 1300 of central member 1292. Inner surface 1310 adjacent to open end 1312 of knob 1304 includes threads for engaging the threads of threaded flared region 1294 of central member 1292. Opposite open end 1312, knob 1304 includes a plurality of outwardly extending gripping surfaces 1314 at end 1316. Internally, end 1316 includes a taper 1318. Side wall 1320 of knob 1304 defines one or more holes 1322 for receiving a respective pin 1324 for preventing knob 1304 from being separated from central member 1292.

Referring again to FIG. 71, foot plate 1326 has a rectangular base portion 1328 and a coupling portion 1330. Coupling portion 1330 includes a pair of pegs 1332, 1334 that are sized and configured to be received within holes 1222, 1223 defined by sides 1204, 1206 of base plate 1202. Sides 1336, 1338 each define a respective slot 1340, 1342 that are sized and configured to receive biased detents 1212, 1214 of base plate 1202 of foot holder assembly 1200.

Operation

The use of reamer stabilizer 1000, foot holder assembly 1200, drill guide assembly 1260, and foot plate 1326 is now described. As described above, a surgeon uses tibial resection guide mount 100 and tibial resection guide 132 to resect the inferior end of a patient's tibia 16 and uses talar resection guide mount 102 and talar resection guide 166 to resect the superior surface of a patient's talus 14 to create resected joint space 22 as illustrated in FIG. 15.

Figure 74:
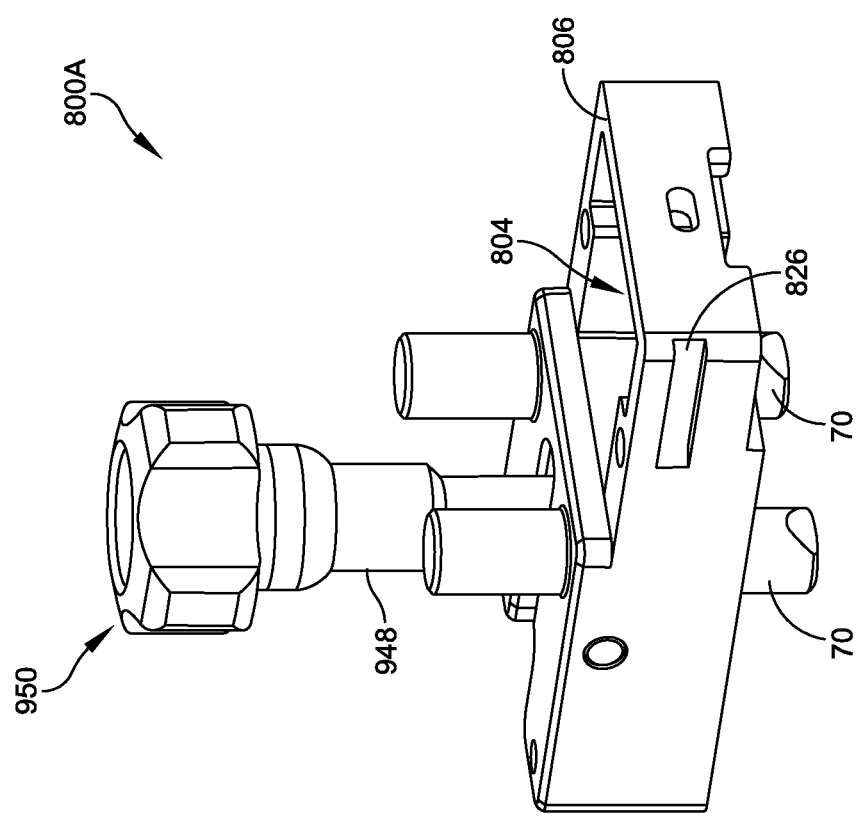
FIG. 74 is an isometric view of one example of a modified mounting member in accordance with the foot holder assembly illustrated in FIG. 71.

Tibial drill guide mount 700 is inserted into resected joint space 22, and mounting plate 800A is connected to tibial drill guide mount 700 using dowel pints in the same way mounting plate 800 is connected to tibial drill guide mount 700 as described above with reference to FIGS. 49 and 50. Cartridge-style tibial drill guide 702 is inserted into aperture 804 of mounting plate 800A and recess 718 of tibial drill guide mount 700. Tibial drill guide cartridge 702 is inserted until leading end 786 of tibial drill cartridge 702 abuts rear wall 788 of tibial drill guide mount 700 at which point the ball detent disposed within hole 772 engages hole 828 defined by mounting plate 800 and the front side 768 of tibial drill guide cartridge 702 is flush with front side 806 of mounting plate 800A, which is illustrated in FIG. 74.

Mounting member 1232 of foot holder assembly 1200 is coupled to tibial drill guide mount 700 and mounting plate 800A using dowel pins 70. For example, holes 1246, 1248 defined by second end 1250 are aligned with and receive dowel pins 70 that extend from mounting plate 800A. Pivoting arrangement 948 of mounting member 800A is pivoted from a horizontal position in which lower portion 952 is not received within slot 1252 defined by mounting member 1232 to a vertical position in which lower portion 952 is received within slot 1252. Knob 952 is rotated about its axis (clockwise or counterclockwise) such that the bottom surface 954 of knob 952 contacts mounting member 1232 to maintain engagement between mounting member 1232 and the assemblage of tibial drill guide mount 700 and mounting plate 800A.

Figure 76:
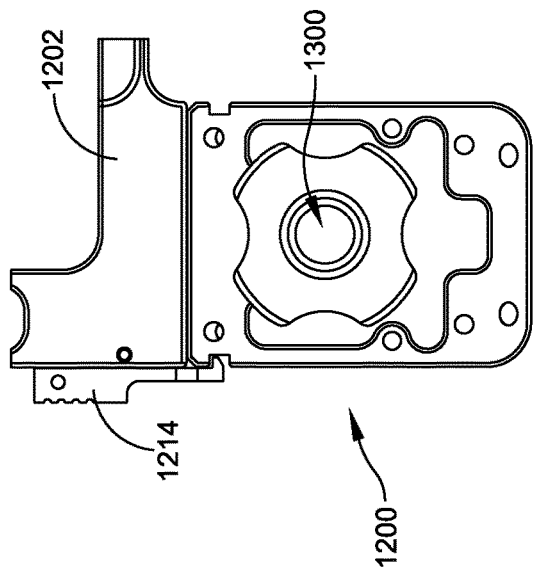
FIGS. 75 and 76 illustrate the coupling of the drill guide assembly illustrated in FIG. 72 to the foot holder assembly illustrated in FIG. 71.
Figure 75:
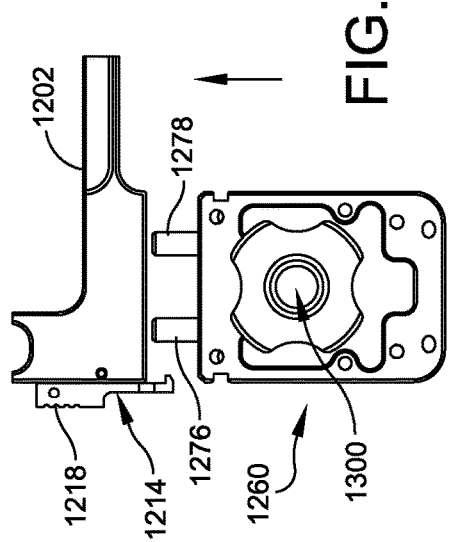

As illustrated in FIGS. 75 and 76, drill guide assembly 1260 is coupled to the appropriate side 1204, 1206 of base plate 1202 such that drill guide assembly 1260 will be disposed directly adjacent to the heel of a patient's foot. The coupling of drill guide assembly 1260 to base plate 1202 includes inserting pegs 1276, 1278 into holes 1220 defined by side 1204 or into holes 1222 defined by side 1206. As pegs 1276, 1278 are inserted into holes 1220 or 1222, biased detent 1212 or 1214 outwardly flexes in response to contacting base 1262 of drill guide assembly 1260 and is then urged into a locking engagement within one of slots 1272 or 1274 defined by sides 1268, 1270 by a biasing member when a detent 1212 or 1214 is aligned with a slot 1272 or 1274.

Foot plate 1326 is coupled to the side 1204, 1206 of base plate 1202 that is opposite the side 1204, 1206 to which drill guide assembly 1260 is coupled such that foot plate 1326 is disposed adjacent to the forefoot of the patient. The coupling of foot plate 1326 to base plate 1202 includes inserting pegs 1332, 1334 into holes 1220 defined by side 1204 or into holes 1222 defined by side 1206 of base plate 1202. As pegs 1332, 1334 are inserted into holes 1220 or 1222, biased detent 1212 or 1214 outwardly flexes in response to contacting coupling portion 1330 of foot plate 1326. Detent 1212 or 1214 is urged into a slot 1340 or 1342 defined by a side 1336 or 1338 of coupling portion 1330 when detent 1212 or 1214 is aligned with slot 1340 or 1342.

The distance between base plate 1202 and mounting member 1232 can be adjusted by unscrewing locking screw 1242 such that mounting member 1232 can be slid along rods 1226, 1228. When the desired positioning of mounting member 1232 relative to base plate 1202 has been achieved, locking screw 1242 is rotated to lock mounting member 1232 at its position along rods 1226, 1228.

Figure 77:
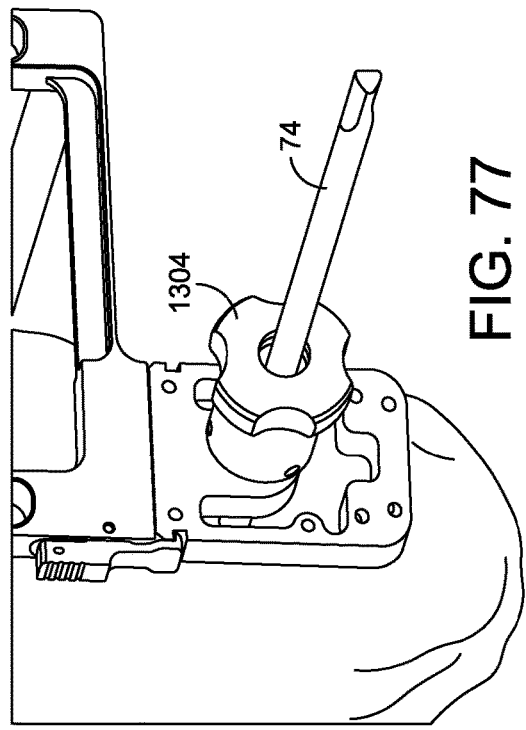
FIG. 77 illustrates a trocar being received within the drill guide assembly.

A trocar 74, which is illustrated in FIG. 77, having ink applied to its tip is inserted into bore 1300 defined by central member 1292 of locking bushing assembly 1290 and touched the skin of the patient's foot to create a mark. Drill guide assembly 1260 is removed from its engagement with base plate 1202 by pressing the biased detent 1212, 1214 that is engaged with a slot 1268, 1270 defined by base 1262 such that detent 1212, 1214 is urged out of its engagement with the slot 1268, 1270. With detent 1212, 1214 disengaged from slot 1268, 1270, base 1262 is pulled away from base 1202 until pegs 1278, 1280 are removed from holes 1220 or 1222.

With drill guide assembly 1260 removed, access to the calcaneus 20 of the patient is made by making a small incision at the marked location using a scalpel or other surgical cutting tool. Drill guide assembly 1260 is then re-coupled to base plate 1202 as described above.

A drill bushing or cannula (not shown) is inserted into bore 1300 and then locked in place by rotating knob 1304 of locking bushing assembly 1294. Rotating knob 1304 causes the threads formed on inner surface 1310 of knob 1304 to engage the threads of threaded flared region 1294. As knob 1304 is rotated in one direction, e.g., a clockwise direction, the rotation of knob 1304 relative to central member 1292 causes knob 1304 to be advanced along central member 1292 towards base 1262, which results in taper 1318 contacting flexible prongs 1298. Flexible prongs 1298 are urged inwardly towards one another as knob 1304 moves towards base 1262 thereby providing a frictional lock between locking bushing assembly 1290 and drill bushing or cannula.

With drill bushing or cannula locked to locking bushing assembly 1290, a drill is used to create a pilot hole through the calcaneus 20, talus 14, and into tibia 16. As the drill exits talus 14, the conically shaped internal surface 748 of tibial drill cartridge 702 guides the tip of the drill into tibia 14. Once the pilot hole has been drilled to a desired depth into tibia 14, the drill is backed out and tibial drill cartridge 702 is removed from tibial drill guide mount 700. Removal of cartridge 702 includes inserting a threaded dowel or rod into threaded blind hole 770 and pulling on threaded dowel or rod to remove cartridge 702 from tibial guide mount 700.

A reamer head 66 is inserted into the space vacated by cartridge 702 and is coupled to a driving rod 65 of a reamer that is received within the vacated space having been inserted through the drill bushing or cannula locked in locking bushing assembly 1290.

Figure 78:
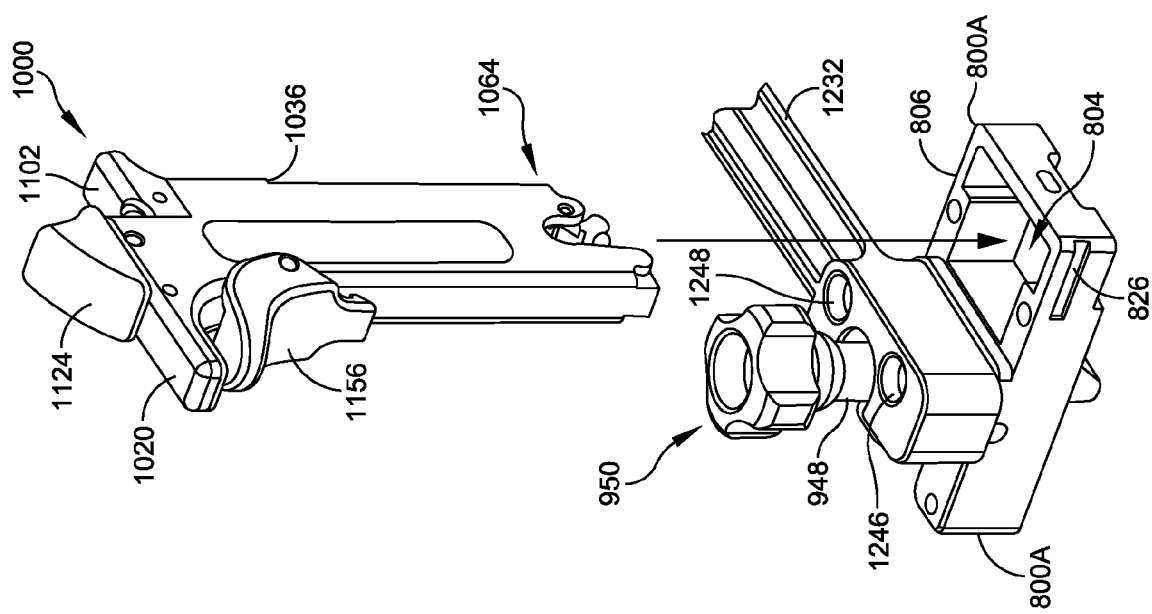
FIGS. 78 and 79 illustrate a reamer stabilizer in accordance with FIG. 63 being coupled to the foot holder assembly illustrated in FIG. 71.
Figure 79:
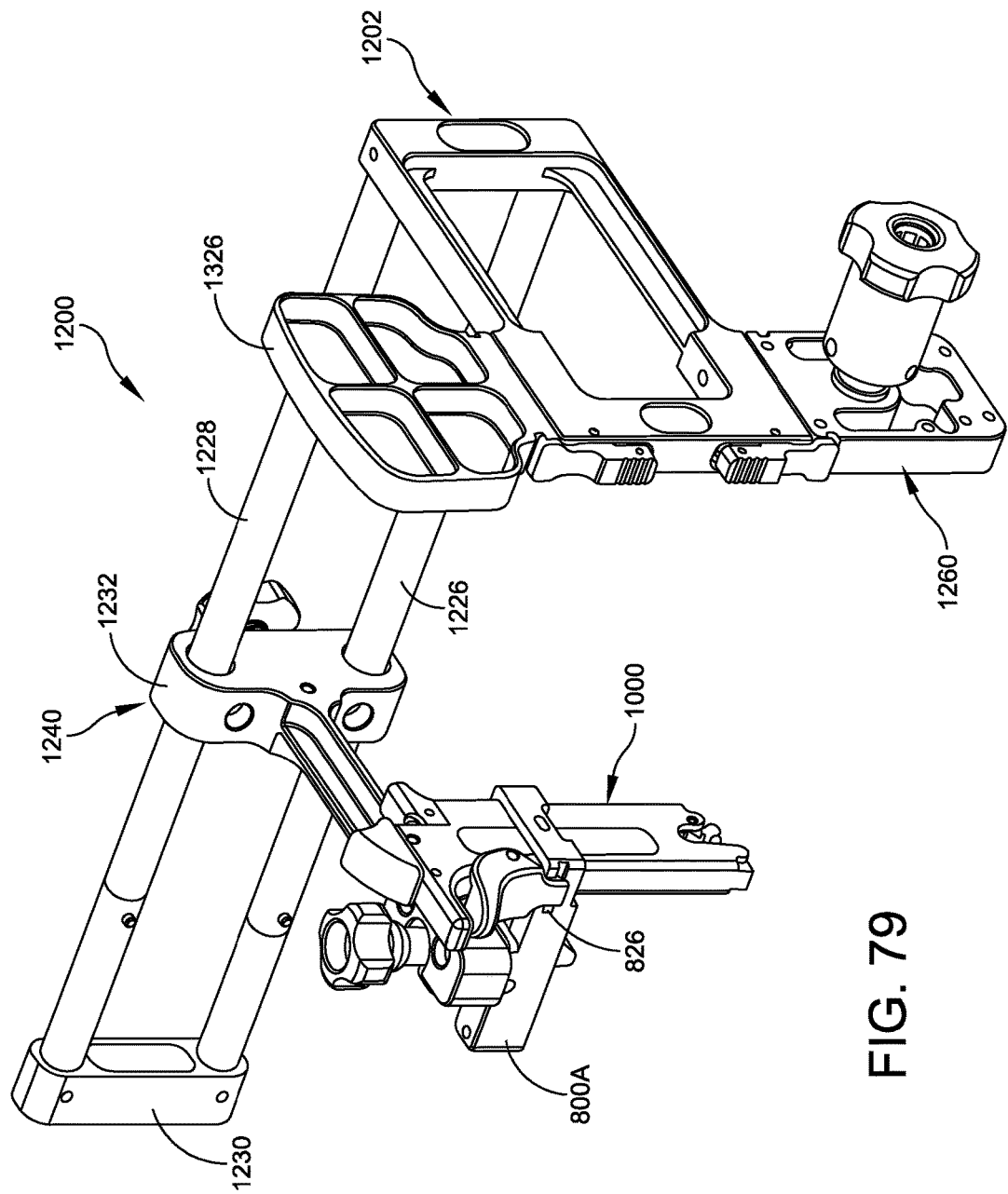

Once reamer head 66 is coupled to reamer rod 65, reamer stabilizer 1000 is secured to mounting plate 800A as described with reference to FIGS. 78 and 79. Distal end 1004 of stabilizer body 1002 is inserted into aperture 804 of mounting plate 800A and into body 704 via recess 718 defined by front side 706 of tibial drill guide mount 700. Reamer stabilizer 1000 continues to be advanced until steps 1034, 1036 contact top surface 806 in an abutting relationship. With steps 1034, 1036 contacting top surface 806, detent 1176 disposed on the inner surface 1178 of pivoting button 1156 is received within slot 826 of mounting plate 800A.

When detent 1176 is disposed within slot 826 and reamer stabilizer 1000 is coupled to mounting plate 800A, reamer driving rod 65 is received within notch 1018 defined at the distal end 1004 of stabilizer body 1002. Guiding assembly 1052 is actuated such that reamer guide body 1054 in combination with notch 1018 encloses and surrounds the reamer driving rod 65 as best seen by comparing FIGS. 64 and 65. Guiding assembly 1052 is actuated by applying a downward pressure (i.e., pressure in a distal direction) to head 1102, which urges plunger rod 1086 and pivot rod 1074 in a distal direction. The movement of plunger rod 1086 and pivot rod 1074 in the distal direction forces reamer guide body 1054 to pivot about hole 1056, which is pinned to stabilizer body 1002 by pin 1042. The distal end 1078 of pivot rod 1074 may outwardly flex with respect to hole 1080 at the proximal end 1084 as reamer guide body 1054 pivots about hole 1056. Although reamer guide body 1054 is illustrated as entirely extending across notch 1018, one of ordinary skill in the art will understand that reamer guide body 1054 will extend only partially across notch 1018 in some embodiments.

Still referring to FIGS. 64 and 65, locking assembly 1122 is configured to automatically lock guiding assembly 1052 in its engaged position with the reamer driving rod 65. Locking button 1124 is urged by biasing member 1152 towards head 1102 such that, when angled surface 1110 of head 1102 is disposed below angled surface 1138 of locking button 1124, locking button 1124 slides over the head 1102 to maintain the engagement of the reamer 65 and concave guiding surface 1058 of reamer guide body 1054. The reamer 65, 66 is advanced into the pilot intramedullary channel previously formed by the drill while being supported by reamer stabilizer 1000, which maintains the direction in which reamer 65, 66 is advanced into tibia 16 and prevents the reamer 65, 66 from wandering.

Once the intramedullary channel has been reamed to a desired depth, the reamer 65, 66 is retracted through the intramedullary channel until the reamer head 66 is received within the resected joint space 22. Reamer stabilizer 1000 is then removed from its engagement with reamer rod 65 and mounting plate 800A. To disengage reamer stabilizer 1000 from its engagement with the reamer 65, locking button 1124 is pushed in a direction away from head 1102 until locking button 1124 is received within cavity 1010 defined by stabilizer body 1002.

Biasing member 1120 of guiding assembly 1052, which is disposed in abutting contact with distal end 1106 of head 1102, causes head 1102, plunger rod 1086, and pivot rod 1074 to move in a proximal direction when locking button 1124 does not contact head 1102 or otherwise impede head 1102 from moving in the proximal direction. The proximal movement of head 1102, plunger rod 1086, and pivot rod 1074 causes reamer guide body 1054 to pivot about pin 1048 due to the cross-pinned engagement between pivot rod 1074 and reamer guide body 1054.

With guiding assembly 1054 disengaged from the reamer, reamer stabilizer 1000 is disengaged from mounting plate 800A by pressing pivoting button 1156 such that button 1156 pivots about pin 1076 and detent 1176 is removed from its engagement with slot 826. Reamer stabilizer 1000 is then pulled from aperture 804. The reamer head 66 is then removed from resected joint space 22.

Knob 952 is rotated in a direction opposite to the direction in which knob 952 was rotated to tighten pivoting arrangement to mounting member 800A such that the bottom surface 954 loosens its frictional engagement with mounting member 1232. Pivoting arrangement 948 is pivoted back to a horizontal position, and locking screw 1242 of mounting member 1232 is loosened by rotating knob 1244 in a direction that is opposite the direction in which knob 1244 was rotated to tighten locking screw 1242. Mounting member 1232 slides along rods 1226, 1228 as base plate 1202 is moved away from the patient's foot.

With the drill bushing or cannula still disposed within the calcaneus 20 and talus 14, drill guide assembly 1260 is decoupled from its engagement with base plate 1202 in the same manner as described above. Foot holder assembly 1200 is then removed such that drill guide assembly 1260, tibial drill guide mount 700, and mounting plate 800A are still engaged with the patient's foot. K-wires 62 used to maintain the position of tibial drill guide mount 700 and mounting plate 800A are removed, and then tibial drill guide mount 700 and mounting plate 800A are removed.

Figure 80:
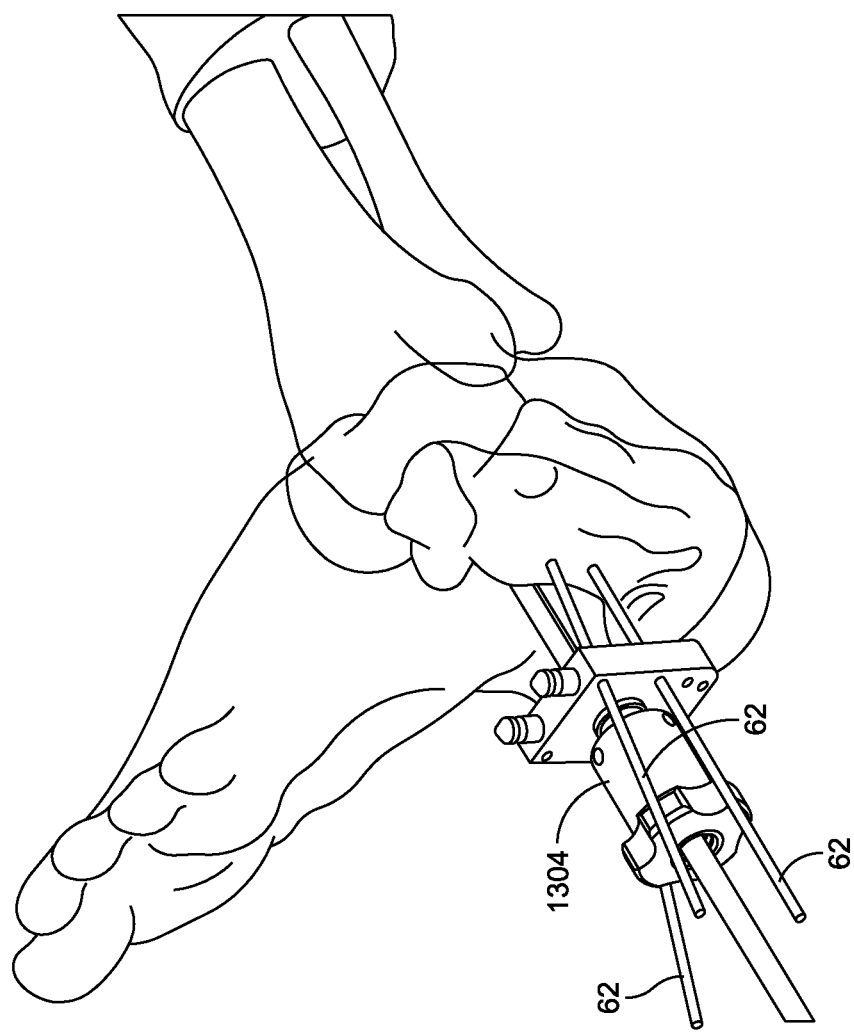
FIG. 80 illustrates the drill guide assembly coupled to the foot of a patient during an operation.
Figure 83:
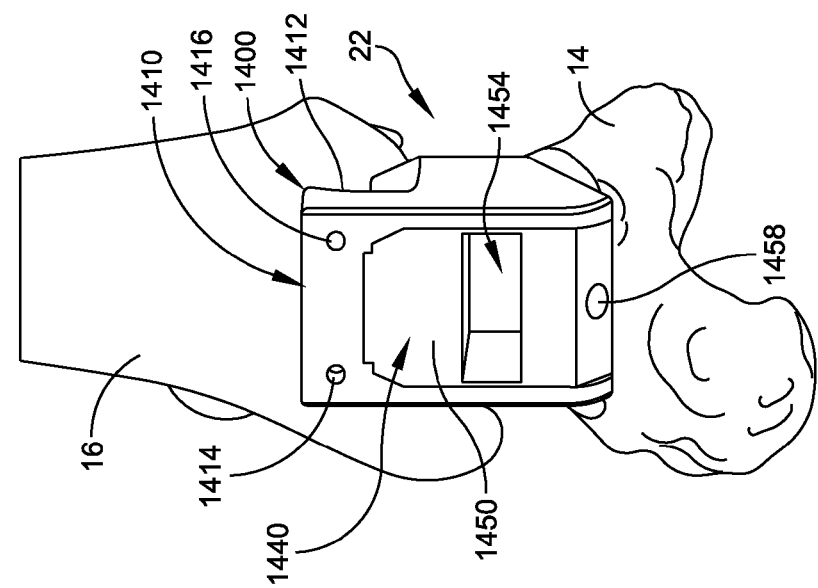
FIG. 83 illustrates the insert illustrated in FIG. 82 disposed within the anterior reaming guide mount, which is received within a resected joint space.

With drill bushing or cannula still disposed within the calcaneus 20 and talus 14, k-wires 62 are inserted through one or more holes 1282 to secure drill guide assembly 1260 to the foot of the patient as illustrated in FIG. 80. Once drill guide assembly 1260 is secured, a tool for driving components of a modular ankle prosthesis into the intramedullary canal formed by the reamer is inserted through drill guide or cannula held by drill guide assembly 1260. The remainder of the installation prosthesis is described in U.S. Pat. No. 7,534,246 issued to Reiley et al.

Anterior Approaches

The disclosed systems and methods described above can also be adapted to enable an intramedullary cavity to be formed in the tibia of a patient via an anterior approach once resected joint space 22 has been formed using tibial resection guide mount 100 and tibial resection guide 132 to resect the inferior end of a patient's tibial and uses talar resection guide mount 102 and talar resection guide 166 to resect the superior surface of a patient's talus 14 to create resected joint space 22 as illustrated in FIG. 15. The anterior approach of forming an intramedullary channel in a patient's tibia avoids drilling through the calcaneus and talus of the patient.

Referring now to FIGS. 81-89, a custom anterior reaming guide mount 1400 is illustrated as being disposed within resected joint space 22. Reaming guide mount 1400 is formed from a resilient polymer material of the type that is suitable for use in connection with stereo lithography, selective laser sintering, or like manufacturing equipment.

Reaming guide mount 1400 includes a body 1402 having an inferior surface 1404 configured to mate against the flat formed on the superior surface of the resected talus. The superior surface 1406 includes a pair of opposed angled surfaces 1408 that are configured to correspond to the cuts made using tibial resection guide 166.

A mating portion 1410 extends from superior surface 1406 and includes a conformal bone engaging surface 1412, which is complementary to a surface of the patient's tibia 16. Mating portion 1410 defines holes 1414, 1416 that are sized and configured to receive k-wires 62 for securing reaming guide mount 1400 to talus 16. Superior surface 1406 also defines an opening 1418 through which a reamer head 66 can be received.

Body 1402 also includes a rear wall 1420 and a pair of opposed side walls 1422, 1424 that define a cavity 1426 with superior wall 1428 and inferior wall 1430. In some embodiments, the respective interfaces between superior wall 1428 and side walls 1422, 1424 include chamfers 1432, 1434 or other geometric features used for properly locating insert 1440.

Figure 82:
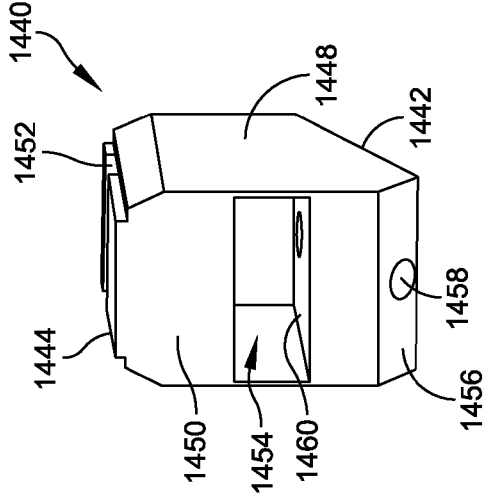
FIG. 82 is an isometric view of one example of an insert for use with the anterior reaming guide mount illustrated in FIG. 81.
Figure 81:
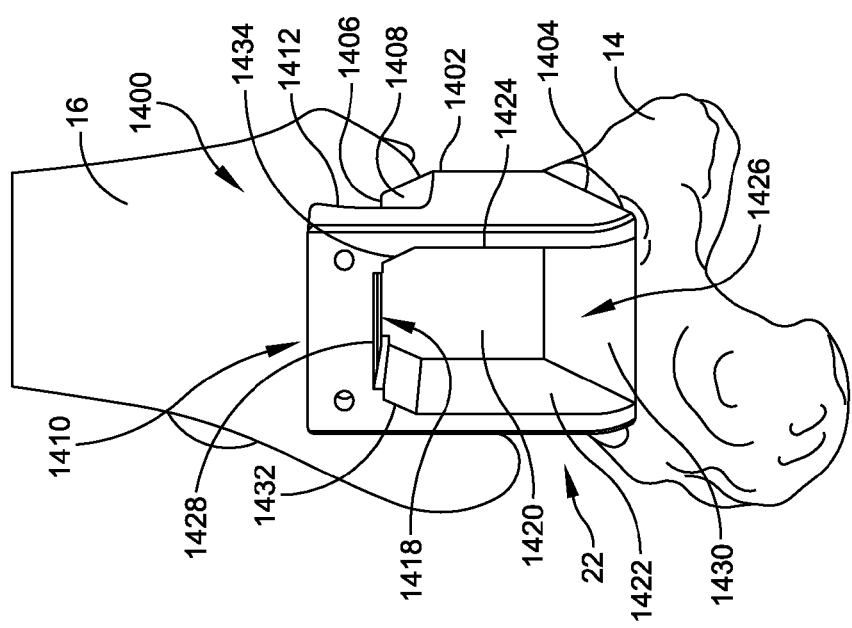
FIG. 81 illustrates one example of an anterior reaming guide mount disposed within a resected joint space in accordance with some embodiments.

As best seen in FIGS. 82,84, and 85, insert 1440 has an overall shape that is complementary to the internal geometry of cavity 1426 defined by reaming guide mount 1400 and can be fabricated from a more durable material than reaming guide mount 1400 such as, for example, a metal material. In particular, insert 1440 includes an inferior surface 1442, a superior surface 1444, side surfaces 1446, 1448, and a front surface 1450. Superior surface 1444 defines an opening 1452 (FIG. 85) through which a reamer head 66 can be received as described in greater detail below.

Front surface 1450 also defines an opening 1454 that is sized such that a reamer head 66 can be received within opening 1454. Openings 1452 and 1454 communicate with each other such that the reamer head inserted within opening 1454 can be received within opening 1452 via internal communication between the openings 1452, 1454. In some embodiments, opening 1454 is smaller than the size of a reamer head 66, but provides a surgeon access a reamer head 66 disposed within opening 1454 such that reamer head 66 can be coupled to a reamer driving rod 65.

An angled front face 1456 is disposed between front face 1450 and inferior surface 1442. Angled front face 1456 defines a passageway 1458 that extends from angled front face 1456 to bottom surface 1460 of internal chamber 1562. Passageway 1562 is sized and configured to receive a flexible reamer.

In operation, reaming guide mount 1400 is inserted into resected joint space 22. Angled surfaces 1408, 1410 of superior surface 1406 and conformal bone engaging surface 1414 precisely locate reaming guide mount 1400 within the resected joint space 22.

A reamer head 66 is inserted into opening 1452 defined by superior surface 1452 of insert 1440. Insert 1440 is inserted into cavity 1428 until opening 1452 defined by superior surface 1444 of insert 1440 aligns with opening 1420 defined by superior surface 1420 of reaming guide mount 1400. A reamer rod 65 is inserted into passageway 1458 defined by angled front face 1456 and coupled to reamer head 66 disposed within opening 1452. A surgeon may insert one or more tools in opening 1454 to secure reamer head 66 to reamer rod 65. Reamer head 66 can then be advanced into the patient's tibia 16.

Figure 89:
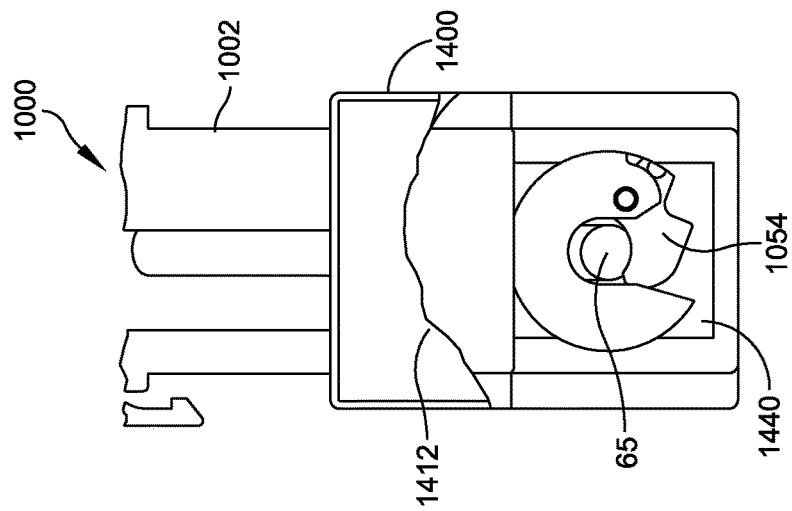
FIGS. 87-89 illustrate the reamer stabilizer, anterior reaming guide mount, and insert during various stages of an operation.
Figure 88:
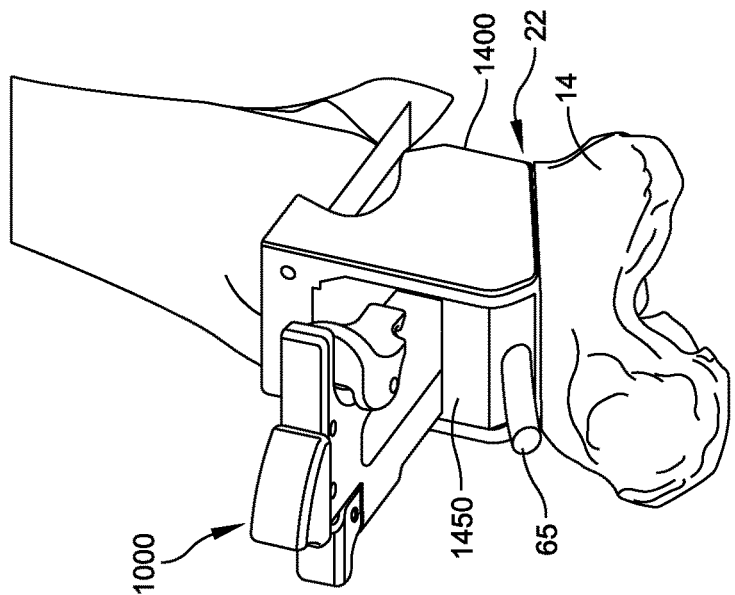
Figure 87:
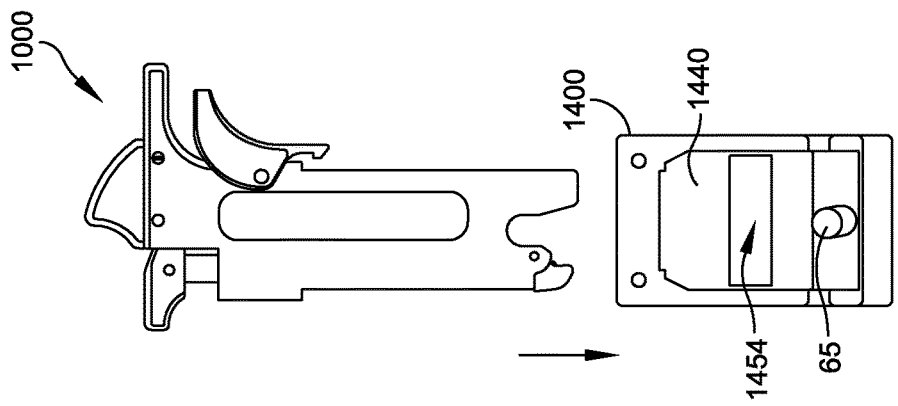

In some embodiments, reamer stabilizer 1000 is used to in connection with reaming guide mount 1400 and insert 1440. For example and as illustrated in FIGS. 87-89, with a reamer head 66 and reamer body 65 assembled together within the construct of reaming guide mount 1400 and insert 1440, which are disposed within resected joint space 22, reamer stabilizer 1000 is coupled to stabilizer driving rod 65. To couple reamer stabilizer 1000 to stabilizer driving rod 65, distal end 1004 of stabilizer body 1002 is inserted into opening 1454 defined by front surface 1450 of insert 1440 until driving rod 65 is received within notch 1018 defined at the distal end 1004 of stabilizer body 1002.

Guiding assembly 1052 is actuated such that reamer guide body 1054 and notch 1018 encloses and surrounds the reamer driving rod 65 as best seen in FIG. 89. Guiding assembly 1052 is actuated by applying a downward pressure (i.e., pressure in a distal direction) to head 1102, which urges plunger rod 1086 and pivot rod 1074 in a distal direction. The movement of plunger rod 1086 and pivot rod 1074 in the distal direction forces reamer guide body 1054 to pivot about hole 1056, which is pinned to stabilizer body 1002 by pin 1042. The distal end 1078 of pivot rod 1074 may outwardly flex with respect to hole 1080 at the proximal end 1084 as reamer guide body 1054 pivots about hole 1056.

Locking assembly 1122 is configured to automatically lock guiding assembly 1052 in its engaged position with the reamer driving rod 65. As described above, locking button 1124 is urged by biasing member 1152 towards in the direction towards head 1102 such that, when angled surface 1110 of head 1102 is disposed below angled surface 1138 of locking button 1124, locking button 1124 slides over the head 1102 to maintain the engagement of the reamer rod 65 and concave guiding surface 1058 of reamer guide body 1054.

The reamer 65, 66 is advanced into tibia 16 to form a reamed intramedullary channel while being supported by reamer stabilizer 1000, which maintains the direction in which reamer 65, 66 is advanced into tibia 16 and prevents the reamer 65, 66 from wandering within tibia 16.

Once the intramedullary channel has been reamed to a desired depth, the reamer 65, 66 is retracted through the intramedullary channel until the reamer head 66 is received within opening 1420 defined by superior surface 1406 of reaming guide mount 1400 and/or within opening 1452 defined by superior surface 1444 defined by insert 1440. Reamer stabilizer 1000 is then removed from its engagement with reamer rod 65.

To disengage reamer stabilizer 1000 from its engagement with the reamer rod 65, locking button 1124 is pushed in a direction away from head 1102 until locking button 1124 is received within cavity 1010 defined by stabilizer body 1002. Biasing member 1120 of guiding assembly 1052, which is disposed in abutting contact with distal end 1106 of head 1102, causes head 1102, plunger rod 1086, and pivot rod 1074 to move in a proximal direction when locking button 1124 does not contact head 1102 or otherwise impede head 1102 from moving in the proximal direction. The proximal movement of head 1102, plunger rod 1086, and pivot rod 1074 causes reamer guide body 1054 to pivot about pin 1048 due to the cross-pinned engagement between pivot rod 1074 and reamer guide body 1054. With guiding assembly 1054 disengaged from the reamer, reamer stabilizer 1000 is pulled out of opening 1454 defined by front surface 1450 of insert 1440.

Figure 92:
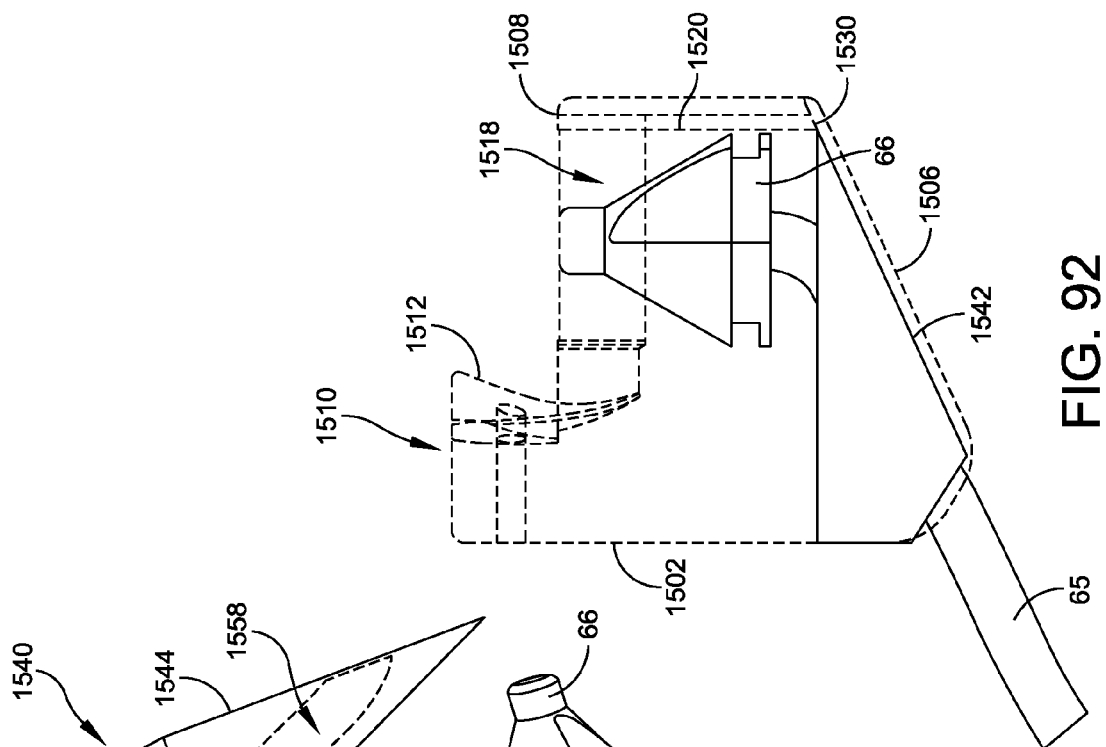
FIG. 92 is a side view of the insert disposed within the anterior reaming guide mount in accordance with FIG. 90.
Figure 90:
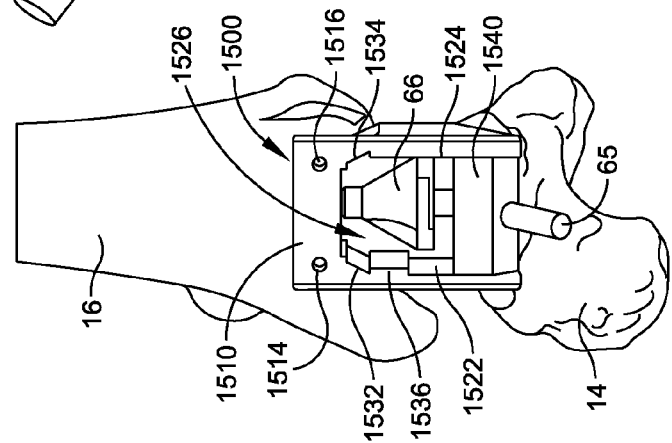
FIG. 90 illustrates another example of an anterior reaming guide mount and insert disposed within a resected joint space during an operation.

As will be understood by one of ordinary skill in the art, the size and shape of reaming guide mount and insert may be varied. For example, FIGS. 90-94 illustrate another embodiment of reaming guide mount 1500 and insert 1540. As shown in FIGS. 90 and 92, body 1502 of reaming guide mount 1500 has an inferior surface 1504 configured to mate against the flat formed on the superior surface of the resected talus. The superior surface 1506 includes a pair of opposed angled surfaces 1508 that are configured to correspond to the cuts made using tibial resection guide 166.

Mating portion 1510 extends from superior surface 1506 and includes a conformal bone engaging surface 1512 (FIG. 92), which is complementary to a surface of the patient's tibia 16. Holes 1514, 1516 are defined by mating portion 1512 and are sized and configured to receive k-wires 62 for securing reaming guide mount 1500 to talus 16. Superior surface 1508 also defines an opening 1518 through which a reamer head 66 can be received.

Body 1502 also includes a rear wall 1520 (FIG. 92) and a pair of opposed side walls 1524, 1526 that define a cavity 1526 with superior wall 1528 and inferior wall 1530 (FIGS. 90 and 92). The respective interfaces between superior wall 1528 and side walls 1524, 1526 include chamfers 1432, 1434 or other geometric features used for properly locating insert 1540. An inwardly projecting structure 1538 extends from side wall 1524.

Figure 91:
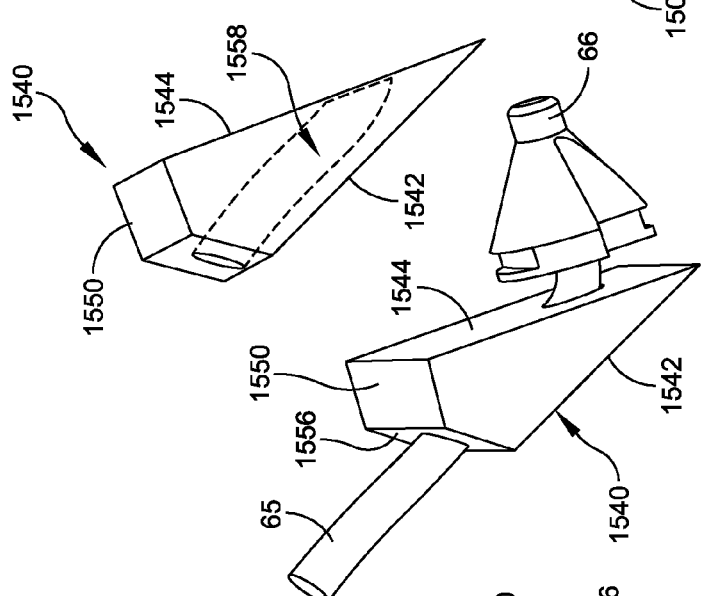
FIG. 91 are isometric side view of the insert illustrated in FIG. 90.

As best seen in FIG. 91, insert 1540 has a triangular wedge shape such that it is able to be received between inwardly projecting structure 1538 and inferior wall 1530 of reaming guide mount 1500. Insert 1540 includes an inferior surface 1542, a superior surface 1544, side surfaces 1546, 1548 (FIG. 94), and a front surface 1550. Angled front face 1556 is disposed between front face 1550 and inferior surface 1542 and defines a passageway 1558 that extends from angled front face 1556 to superior surface 1544. Passageway 1558 is sized and configured to receive a flexible reamer rod 65.

Figure 94:
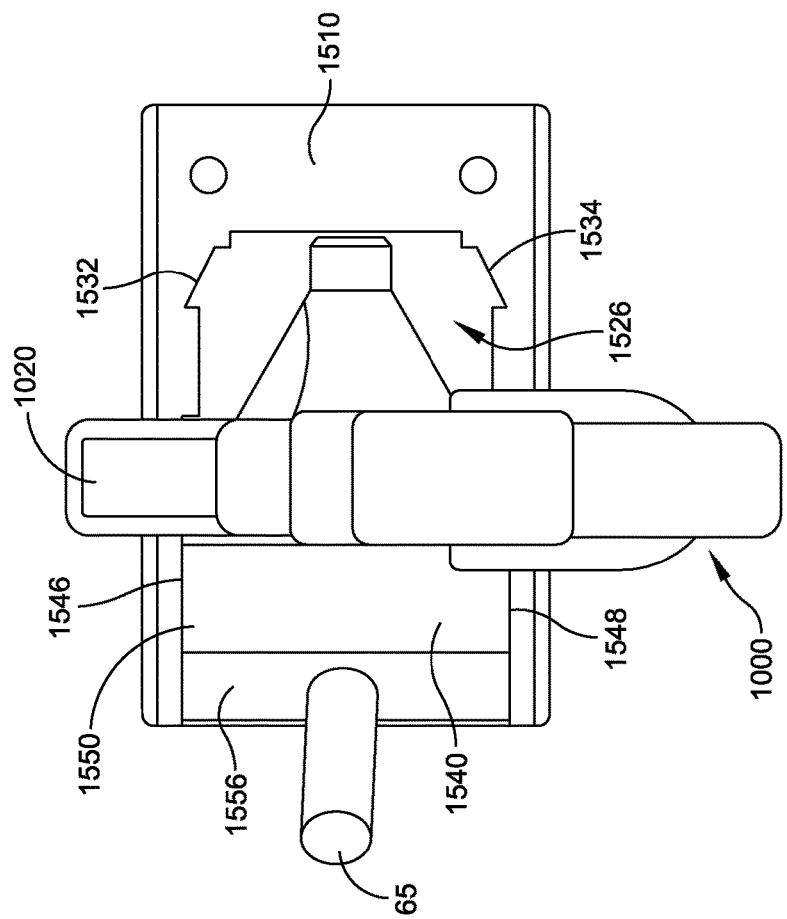
FIGS. 93 and 94 illustrate the reamer stabilizer in use with the anterior reaming guide mount and insert illustrated in FIG. 90.
Figure 93:
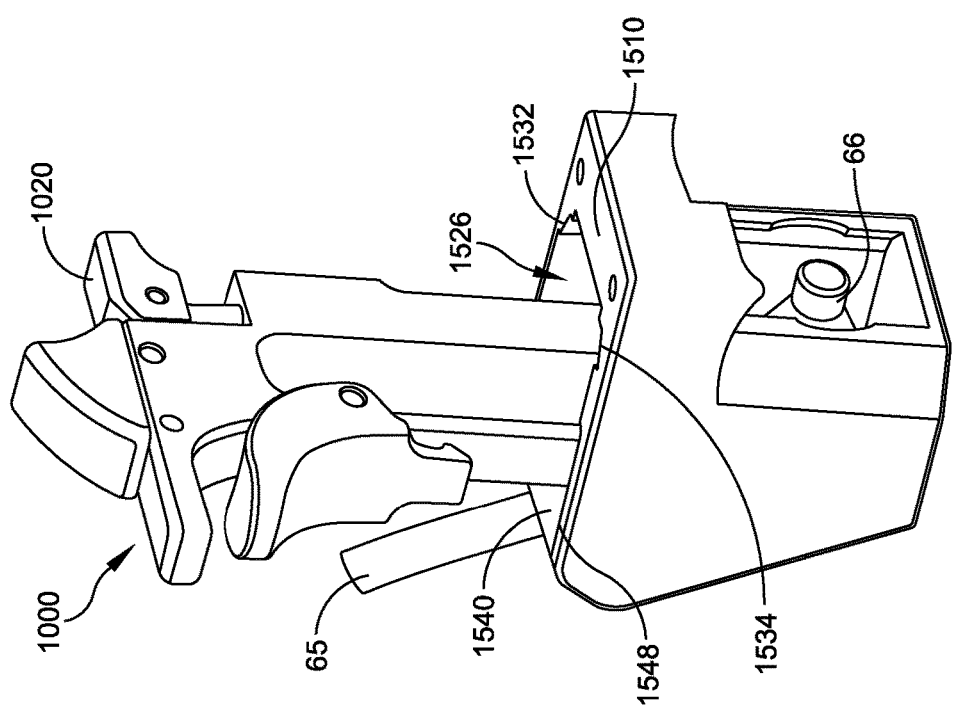
Figure 97:
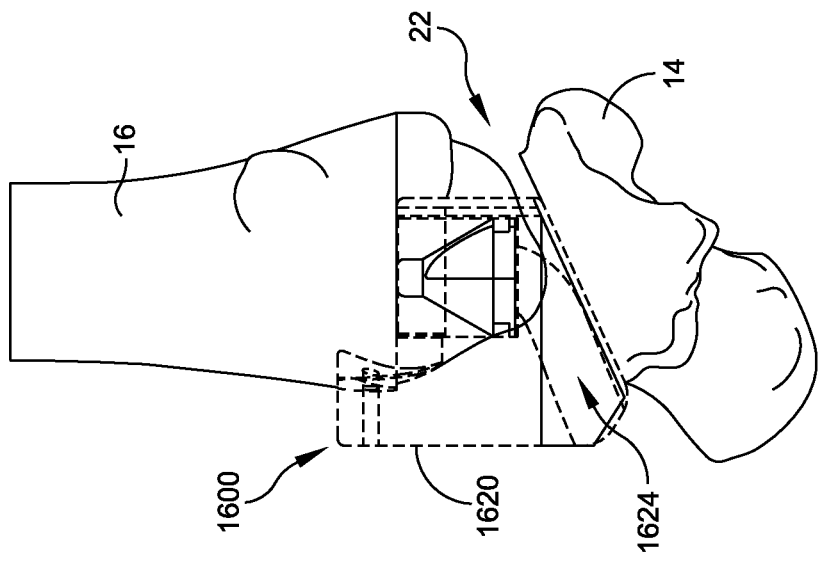
Figure 96:
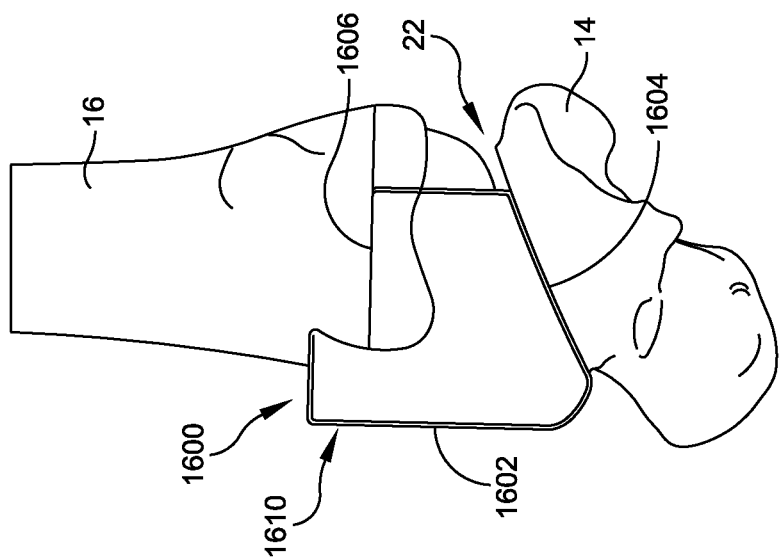
Figure 95:
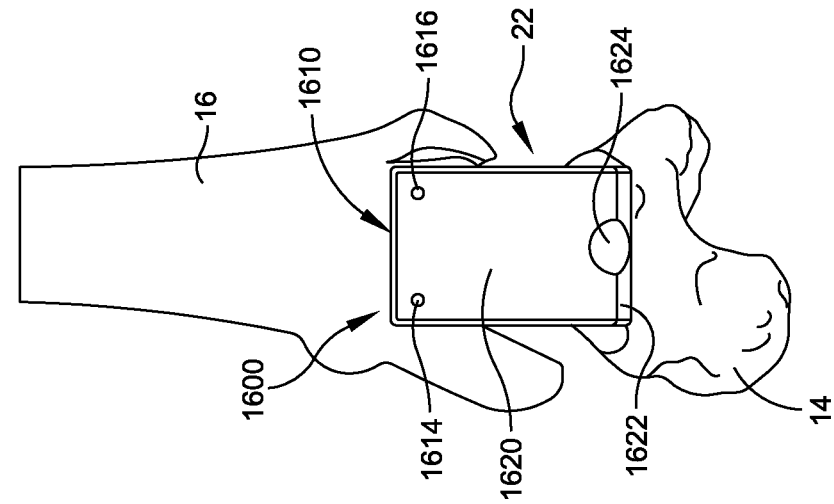

As shown in FIGS. 93 and 94, reamer stabilizer 1000 is received within cavity 1526 adjacent to insert 1540 such that reamer stabilizer 1000 abuts both inwardly projecting structure 1536 and insert 1540. Reamer stabilizer 1000 stabilizes reamer 65, 66 as reamer 65, 66 is advanced into the tibia 16 of a patient as described above.

Another embodiment of an anterior reaming guide mount is illustrated in FIGS. 95-100. Reaming guide mount 1600 includes a body 1062 having an inferior surface 1604 (FIG. 96) configured to mate against the flat formed on the superior surface of the resected talus 14. The superior surface 1606 includes a pair of opposed angled surfaces 1608 (FIGS. 99 and 100) that are configured to correspond to the cuts made using tibial resection guide 166.

Mating portion 1610 extends from superior surface 1606 and includes a conformal bone engaging surface 1614, which is complementary to a surface of the patient's tibia 16. Holes 1614, 1616 are defined by mating portion 1612 and are sized and configured to receive k-wires 62 for securing reaming guide mount 1600 to talus 16. Superior surface 1606 also defines an opening 1618 through which a reamer head 66 can be received.

Body 1602 also includes a front surface 1622 and an angled front surface 1624 that defines a passageway 1626 that communicates with opening 1620. Passageway 1626 is configured to receive a flexible reamer driving rod 65 that is to be coupled to a reamer head 66 disposed within opening 66.

The disclosed systems and methods advantageously utilize custom manufactured surgical instruments, guides, and/or fixtures that are based upon a patient's anatomy to reduce the use of fluoroscopy during a surgical procedure. In some instances, the use of fluoroscopy during a surgical procedure may be eliminated altogether. The custom instruments, guides, and/or fixtures are created by imaging a patient's anatomy with a computer tomography scanner ("CT"), a magnetic resonance imaging machine ("MRI"), or like medical imaging technology prior to surgery and utilizing these images to create patient-specific instruments, guides, and/or fixtures.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. A system, comprising:
   a first surgical device having a hollow body that extends from a first side to a second side and includes a third side and a fourth side, the third and fourth sides extending between the first side and the second side and being disposed opposite one another, at least a portion of the hollow body being sized and configured to be received within a resected space between a first bone and a second bone, the first surgical device including an engagement structure extending from the third side and having a conformal engagement surface configured to engage one of the first bone and the second bone; and
   a second surgical device configured to be at least partially received within the hollow body of the first surgical device via an opening defined by the first side of the first surgical device, the second surgical device including
      an elongate body extending from a first end to a second end, the first end defining a notch sized and configured to receive a third surgical device, and
      a coupling assembly supported by the elongate body, the coupling assembly including a reamer guide body configured to move between a first position and a second position in which the reamer guide body extends at least partially across the notch.

2. The system of claim 1, wherein the second surgical device includes a locking assembly supported by the elongate body, the locking assembly configured to releasably engage the coupling assembly to maintain the reamer guide body in the second position.

3. The system of claim 1, wherein the coupling assembly is sized and configured to be received within the hollow body of the first surgical device.

4. The system of claim 1, wherein the third and fourth sides of the first surgical device each define a respective aperture sized and configured to receive a third surgical device therein.

5. The system of claim 1, wherein the coupling assembly includes first and second rods disposed within a longitudinal channel defined by the elongate body, the first rod coupled to a head extending outwardly from the longitudinal channel, and the second rod pivotally coupled to the first rod and to an end of the reamer guide.

6. The system of claim 5, wherein the coupling assembly includes a biasing member disposed within the longitudinal channel, the biasing member configured to bias the head toward the second end.

7. The system of claim 1, wherein the locking assembly includes
   a button slidably positioned within a cavity defined at the proximal end of the elongate body, and
   a biasing member configured to urge the button in a direction towards the coupling assembly.

8. The system of claim 1, wherein the elongate body includes a step along at least one side.

9. The system of claim 1, wherein the reamer guide body includes
   an arcuate surface configured to support a reamer, the reamer guide body disposed adjacent to a first hole configured to receive a first pin for pivotably coupling the reamer guide body to the distal end of the elongate body, and a second hole is defined adjacent to the first hole, the second hole configured to receive a second pin for pivotably coupling the reamer guide body to a pivoting rod of the coupling assembly.

10. A system, comprising:

a first surgical device having a hollow body that extends from a first side to a second side and includes a third side and a fourth side, the third and fourth sides extending between the first side and the second side and being disposed opposite one another, at least a portion of the hollow body being sized and configured to be received within a resected space between a first bone and a second bone, the first surgical device including an engagement structure extending from the third side and having a conformal engagement surface configured to engage one of the first bone and the second bone; and a second surgical device configured to be at least partially received within the hollow body of the first surgical device via an opening defined by the first side of the first surgical device, the second surgical device including an elongate body extending from a first end to a second end, the first end defining a notch sized and configured to receive a third surgical device, a coupling assembly supported by the elongate body, the coupling assembly including a reamer guide body configured to move between a first position and a second position in which the reamer guide body extends at least partially across the notch, and a locking assembly supported by the elongate body, the locking assembly configured to releasably engage the coupling assembly to maintain the reamer guide body in the second position.

11. The system of claim 10, wherein the coupling assembly is sized and configured to be received within the hollow body of the first surgical device.

12. The system of claim 10, wherein at least one of the third and fourth sides of the first surgical device defines an respective aperture sized and configured to receive a third surgical device therein.

13. The system of claim 10, wherein the coupling assembly includes first and second rods disposed within a longitudinal channel defined by the elongate body, the first rod coupled to a head extending outwardly from the longitudinal channel, and the second rod pivotally coupled to the first rod and to an end of the reamer guide.

\* \* \* \* \*